(12) United States Patent
Argento et al.

(10) Patent No.: US 12,167,960 B2
(45) Date of Patent: *Dec. 17, 2024

(54) MULTI-PIECE ACCOMMODATING INTRAOCULAR LENSES AND METHODS FOR MAKING AND USING SAME

(71) Applicant: Shifamed Holdings, LLC, Campbell, CA (US)

(72) Inventors: Claudio Argento, Felton, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 494 days.

This patent is subject to a terminal disclaimer.

(21) Appl. No.: 17/367,107

(22) Filed: Jul. 2, 2021

(65) Prior Publication Data

US 2022/0160496 A1  May 26, 2022

Related U.S. Application Data

(60) Continuation of application No. 16/426,211, filed on May 30, 2019, now Pat. No. 11,065,109, which is a
(Continued)

(51) Int. Cl.
*A61F 2/16* (2006.01)

(52) U.S. Cl.
CPC .......... *A61F 2/1635* (2013.01); *A61F 2/1648* (2013.01); *A61F 2/1629* (2013.01); *A61F 2002/1682* (2015.04); *A61F 2002/169* (2015.04)

(58) Field of Classification Search
None
See application file for complete search history.

(56) References Cited

U.S. PATENT DOCUMENTS

| | | |
|---|---|---|
| 4,440,918 A | 4/1984 | Rice et al. |
| 4,663,409 A | 5/1987 | Friends et al. |
| (Continued) | | |

FOREIGN PATENT DOCUMENTS

| | | |
|---|---|---|
| AU | 2006200142 A1 | 7/2006 |
| AU | 2015361227 | 4/2017 |
| (Continued) | | |

OTHER PUBLICATIONS

Klank et al. "CO2-laser micromachining and back-end processing for rapid production of PMMA-based microfluidic systems" Lab Chip 2002 2 242-246.
(Continued)

*Primary Examiner* — Leslie A Lopez
(74) *Attorney, Agent, or Firm* — Perkins Coie LLP

(57) ABSTRACT

An accommodating intraocular lens (AIOL) for implantation within a capsular bag of a patient's eye comprises first and second components coupled together to define an inner fluid chamber and an outer fluid reservoir. The inner region of the AIOL provides optical power with one or more of the shaped fluid within the inner fluid chamber or the shape of the first or second components. The fluid reservoir comprises a bellows region with fold(s) extending circumferentially around an optical axis of the eye. The bellows engages the lens capsule, and a compliant fold region between the inner and outer bellows portions allows the profile of the AIOL to deflect when the eye accommodates for near vision. Fluid transfers between the inner fluid chamber and the outer fluid reservoir to provide optical power changes. A third lens component coupled to the first or second component provides additional optical power.

20 Claims, 20 Drawing Sheets

Related U.S. Application Data division of application No. 15/890,619, filed on Feb. 7, 2018, now Pat. No. 10,350,056, which is a continuation of application No. PCT/US2017/068226, filed on Dec. 22, 2017.

(60) Provisional application No. 62/549,333, filed on Aug. 23, 2017, provisional application No. 62/544,681, filed on Aug. 11, 2017, provisional application No. 62/438,969, filed on Dec. 23, 2016.

(56) References Cited

U.S. PATENT DOCUMENTS

| | | |
|---|---|---|
| 4,709,996 A | 12/1987 | Michelson et al. |
| 4,731,078 A | 3/1988 | Stoy et al. |
| 4,731,080 A | 3/1988 | Galin |
| 4,842,601 A | 6/1989 | Smith et al. |
| 4,892,543 A | 1/1990 | Turley |
| 4,932,966 A | 6/1990 | McMaster et al. |
| 4,932,971 A | 6/1990 | Kelman |
| 5,074,942 A | 12/1991 | Orlosky et al. |
| 5,211,662 A | 5/1993 | Barrett et al. |
| 5,217,491 A | 6/1993 | Vanderbilt |
| 5,366,502 A | 11/1994 | Patel |
| 5,405,386 A | 4/1995 | Rheinish et al. |
| 5,423,929 A | 6/1995 | Grisoni et al. |
| 5,489,302 A | 2/1996 | Skottun |
| 5,556,929 A | 9/1996 | Yokoyama et al. |
| 5,612,391 A | 3/1997 | Chabrecek et al. |
| 5,620,720 A | 4/1997 | Glick et al. |
| 5,807,944 A | 9/1998 | Hirt et al. |
| 5,891,931 A | 4/1999 | Leboeuf et al. |
| 5,914,355 A | 6/1999 | Kuenzler |
| 5,944,753 A | 8/1999 | Galin et al. |
| 5,945,465 A | 8/1999 | Ozark et al. |
| 5,945,498 A | 8/1999 | Lohmann et al. |
| 6,140,438 A | 10/2000 | Kawaguchi et al. |
| 6,197,059 B1 | 3/2001 | Cumming |
| 6,346,594 B1 | 2/2002 | Watanabe et al. |
| 6,447,920 B1 | 9/2002 | Chabrecek et al. |
| 6,465,056 B1 | 10/2002 | Chabrecek et al. |
| 6,521,352 B1 | 2/2003 | Lohmann et al. |
| 6,537,316 B1 | 3/2003 | Chambers |
| 6,558,420 B2 | 5/2003 | Green et al. |
| 6,582,754 B1 | 6/2003 | Pasic et al. |
| 6,586,038 B1 | 7/2003 | Chabrecek et al. |
| 6,630,243 B2 | 10/2003 | Ozark et al. |
| 6,660,035 B1 | 12/2003 | Yaross et al. |
| 6,685,741 B2 | 2/2004 | Landreville et al. |
| 6,695,881 B2 | 2/2004 | Peng et al. |
| 6,713,583 B2 | 3/2004 | Liao et al. |
| 6,730,123 B1 | 5/2004 | Klopotek et al. |
| 6,734,321 B2 | 5/2004 | Chabrecek et al. |
| 6,747,090 B2 | 6/2004 | Haitjema et al. |
| 6,761,737 B2 | 7/2004 | Ting et al. |
| 6,764,511 B2 | 7/2004 | Ting et al. |
| 6,767,363 B1 | 7/2004 | Green et al. |
| 6,767,979 B1 | 7/2004 | Muir et al. |
| 6,786,934 B2 | 9/2004 | Ting et al. |
| 6,797,004 B1 | 9/2004 | Brady et al. |
| 6,818,017 B1 | 11/2004 | Shu et al. |
| 6,818,158 B2 | 11/2004 | Pham et al. |
| 6,835,410 B2 | 12/2004 | Chabrecek et al. |
| 6,846,326 B2 | 1/2005 | Nguyen et al. |
| 6,858,040 B2 | 2/2005 | Ting et al. |
| 6,884,261 B2 | 4/2005 | Zadno-Azizi et al. |
| 6,893,595 B1 | 5/2005 | Muir et al. |
| 6,893,685 B2 | 5/2005 | Pasic et al. |
| 6,899,732 B2 | 5/2005 | Zadno-Azizi et al. |
| 6,935,743 B2 | 8/2005 | Shadduck |
| 6,969,403 B2 | 11/2005 | Yang et al. |
| 7,041,134 B2 | 5/2006 | Ting et al. |
| 7,087,080 B2 | 8/2006 | Ting et al. |
| 7,097,660 B2 | 8/2006 | Portney |
| 7,118,596 B2 | 10/2006 | Ting et al. |
| 7,198,640 B2 | 4/2007 | Nguyen |
| 7,217,288 B2 | 5/2007 | Esch et al. |
| 7,217,778 B2 | 5/2007 | Flipsen et al. |
| 7,226,478 B2 | 6/2007 | Ting et al. |
| 7,300,464 B2 | 11/2007 | Tran |
| 7,416,562 B2 | 8/2008 | Gross et al. |
| 7,438,723 B2 | 10/2008 | Esch |
| 7,452,378 B2 | 11/2008 | Ting et al. |
| 7,468,397 B2 | 12/2008 | Schorzman et al. |
| 7,479,530 B2 | 1/2009 | Chan et al. |
| 7,557,231 B2 | 7/2009 | Schorzman et al. |
| 7,588,334 B2 | 9/2009 | Matsushita et al. |
| 7,591,849 B2 | 9/2009 | Richardson et al. |
| 7,601,766 B2 | 10/2009 | Schorzman et al. |
| 7,637,947 B2 | 12/2009 | Scholl et al. |
| 7,714,090 B2 | 5/2010 | Iwamoto et al. |
| 7,744,603 B2 | 6/2010 | Zadno-Azizi et al. |
| 7,744,646 B2 | 6/2010 | Zadno-Azizi et al. |
| 7,781,558 B2 | 8/2010 | Schorzman et al. |
| 7,806,929 B2 | 10/2010 | Brown et al. |
| 7,806,930 B2 | 10/2010 | Brown et al. |
| 7,842,087 B2 | 11/2010 | Ben |
| 7,883,540 B2 | 2/2011 | Niwa et al. |
| 7,906,563 B2 | 3/2011 | Huang et al. |
| 7,942,929 B2 | 5/2011 | Linhardt et al. |
| 8,003,710 B2 | 8/2011 | Medina et al. |
| 8,025,823 B2 | 9/2011 | Figueroa et al. |
| 8,034,107 B2 | 10/2011 | Stenger et al. |
| 8,048,155 B2 | 11/2011 | Shadduck et al. |
| 8,071,703 B2 | 12/2011 | Zhou et al. |
| 8,105,623 B2 | 1/2012 | Schorzman et al. |
| 8,158,712 B2 | 4/2012 | Your |
| 8,187,325 B2 | 5/2012 | Zadno-Azizi et al. |
| 8,211,955 B2 | 7/2012 | Chang et al. |
| 8,222,360 B2 | 7/2012 | Liao |
| 8,251,509 B2 | 8/2012 | Zickler et al. |
| 8,283,429 B2 | 10/2012 | Zhou et al. |
| 8,328,869 B2 | 12/2012 | Burns et al. |
| 8,357,771 B2 | 1/2013 | Medina et al. |
| 8,361,145 B2 | 1/2013 | Scholl et al. |
| 8,377,123 B2 | 2/2013 | Zadno et al. |
| 8,414,646 B2 | 4/2013 | Gifford et al. |
| 8,420,711 B2 | 4/2013 | Awasthi et al. |
| 8,425,595 B2 | 4/2013 | Evans et al. |
| 8,425,599 B2 | 4/2013 | Shadduck et al. |
| 8,425,926 B2 | 4/2013 | Qiu et al. |
| 8,430,928 B2 | 4/2013 | Liao |
| 8,454,688 B2 | 6/2013 | Evans et al. |
| 8,486,142 B2 | 7/2013 | Bumbalough et al. |
| 8,500,806 B1 | 8/2013 | Phillips et al. |
| 8,585,758 B2 | 11/2013 | Woods |
| 8,603,166 B2 | 12/2013 | Park |
| 8,609,745 B2 | 12/2013 | Medina et al. |
| 8,663,510 B2 | 3/2014 | Graney et al. |
| 8,680,172 B2 | 3/2014 | Liao |
| 8,728,158 B2 | 5/2014 | Whitsett |
| 8,759,414 B2 | 6/2014 | Winter et al. |
| 8,784,485 B2 | 7/2014 | Evans et al. |
| 8,827,447 B2 | 9/2014 | Awasthi et al. |
| 8,834,566 B1 | 9/2014 | Jones |
| 8,835,525 B2 | 9/2014 | Chang et al. |
| 8,851,670 B2 | 10/2014 | Zickler et al. |
| 8,863,749 B2 | 10/2014 | Gooding et al. |
| 8,877,227 B2 | 11/2014 | Ravi |
| 8,899,745 B2 | 12/2014 | Domschke |
| 8,900,298 B2 | 12/2014 | Chazan et al. |
| 8,956,409 B2 | 2/2015 | Ben Nun |
| 8,968,399 B2 | 3/2015 | Ghabra |
| 8,992,609 B2 | 3/2015 | Shadduck |
| 8,993,651 B2 | 3/2015 | Chang et al. |
| 9,005,492 B2 | 4/2015 | Chang et al. |
| 9,005,700 B2 | 4/2015 | Qiu et al. |
| 9,006,359 B2 | 4/2015 | Schultz et al. |
| 9,011,532 B2 | 4/2015 | Catlin et al. |
| 9,023,915 B2 | 5/2015 | Hu et al. |
| 9,034,035 B2 | 5/2015 | Assia et al. |
| 9,039,174 B2 | 5/2015 | Awasthi et al. |
| 9,044,302 B2 | 6/2015 | Gooding et al. |
| 9,052,439 B2 | 6/2015 | Samuel et al. |

(56) References Cited

U.S. PATENT DOCUMENTS

| | | |
|---|---|---|
| 9,052,440 B2 | 6/2015 | Chang et al. |
| 9,095,424 B2 | 8/2015 | Atkinson et al. |
| 9,097,840 B2 | 8/2015 | Chang et al. |
| 9,125,736 B2 | 9/2015 | Atkinson et al. |
| 9,186,244 B2 | 11/2015 | Rao et al. |
| 9,198,572 B2 | 12/2015 | Zickler et al. |
| 9,198,752 B2 | 12/2015 | Woods |
| 9,254,189 B2 | 2/2016 | Azar et al. |
| 9,265,604 B2 | 2/2016 | Woods |
| 9,277,988 B1 | 3/2016 | Chu |
| 9,280,000 B2 | 3/2016 | Simonov et al. |
| 9,289,287 B2 | 3/2016 | Atkinson et al. |
| 9,326,848 B2 | 5/2016 | Woods |
| 9,364,316 B1 | 6/2016 | Kahook et al. |
| 9,387,069 B2 | 7/2016 | Atkinson et al. |
| 9,398,949 B2 | 7/2016 | Werblin |
| 9,421,088 B1 | 8/2016 | Schieber et al. |
| 9,427,312 B2 | 8/2016 | Tai et al. |
| 9,456,895 B2 | 10/2016 | Shadduck et al. |
| 9,486,311 B2 | 11/2016 | Vaughan et al. |
| 9,498,326 B2 | 11/2016 | Tsai et al. |
| 9,603,703 B2 | 3/2017 | Bumbalough |
| 9,622,855 B2 | 4/2017 | Portney et al. |
| 9,636,213 B2 | 5/2017 | Brady |
| 9,655,775 B2 | 5/2017 | Boukhny et al. |
| 9,681,946 B2 | 6/2017 | Kahook et al. |
| 9,693,858 B2 | 7/2017 | Hildebrand et al. |
| 9,744,027 B2 | 8/2017 | Jansen |
| 9,795,473 B2 | 10/2017 | Smiley et al. |
| 9,814,568 B2 | 11/2017 | Ben Nun |
| 9,907,881 B2 | 3/2018 | Terrisse |
| 10,195,018 B2 | 2/2019 | Salahieh et al. |
| 10,350,057 B2 | 7/2019 | Argento et al. |
| 10,526,353 B2 | 1/2020 | Silvestrini |
| 10,548,718 B2 | 2/2020 | Salahieh et al. |
| 10,709,549 B2 | 7/2020 | Argento et al. |
| 10,736,734 B2 | 8/2020 | Salahieh et al. |
| 11,141,263 B2 | 10/2021 | Argento et al. |
| 11,464,625 B2 | 10/2022 | Link et al. |
| 11,540,916 B2 | 1/2023 | Salahieh et al. |
| 11,583,390 B2 | 2/2023 | Salahieh et al. |
| 2001/0037001 A1 | 11/2001 | Muller et al. |
| 2001/0056165 A1 | 12/2001 | Mentak et al. |
| 2002/0055776 A1 | 5/2002 | Juan, Jr. et al. |
| 2002/0072795 A1 | 6/2002 | Green et al. |
| 2002/0086160 A1 | 7/2002 | Qiu et al. |
| 2002/0102415 A1 | 8/2002 | Valint, Jr. et al. |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0138141 A1 | 9/2002 | Zadno-Azizi et al. |
| 2002/0173847 A1 | 11/2002 | Pham et al. |
| 2002/0182316 A1 | 12/2002 | Gilliard et al. |
| 2002/0197414 A1 | 12/2002 | Chabrecek et al. |
| 2003/0008063 A1 | 1/2003 | Chabrecek et al. |
| 2003/0060878 A1 | 3/2003 | Shadduck |
| 2003/0074060 A1 | 4/2003 | Zadno-Azizi et al. |
| 2003/0074061 A1 | 4/2003 | Pham et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0100666 A1 | 5/2003 | DeGroot et al. |
| 2003/0158560 A1 | 8/2003 | Portney |
| 2003/0162929 A1 | 8/2003 | Verbruggen et al. |
| 2003/0224185 A1 | 12/2003 | Valint, Jr. et al. |
| 2004/0082993 A1 | 4/2004 | Woods |
| 2004/0111152 A1 | 6/2004 | Kelman et al. |
| 2004/0166232 A1 | 8/2004 | Kunzler et al. |
| 2004/0169816 A1 | 9/2004 | Esch |
| 2004/0184158 A1 | 9/2004 | Shadduck |
| 2004/0230300 A1 | 11/2004 | Bandhauer et al. |
| 2005/0013842 A1 | 1/2005 | Qiu et al. |
| 2005/0049700 A1 | 3/2005 | Zadno-Azizi et al. |
| 2005/0055092 A1 | 3/2005 | Nguyen et al. |
| 2005/0119740 A1 | 6/2005 | Esch et al. |
| 2005/0149183 A1 | 7/2005 | Shadduck et al. |
| 2005/0153055 A1 | 7/2005 | Ammon et al. |
| 2005/0165410 A1 | 7/2005 | Zadno-Azizi et al. |
| 2005/0228120 A1 | 10/2005 | Hughes et al. |
| 2005/0228401 A1 | 10/2005 | Zadno-Azizi et al. |
| 2006/0069432 A1 | 3/2006 | Tran |
| 2006/0085013 A1 | 4/2006 | Dusek et al. |
| 2006/0100701 A1* | 5/2006 | Esch .................. A61F 2/1635 623/6.37 |
| 2006/0100703 A1 | 5/2006 | Evans et al. |
| 2006/0116765 A1 | 6/2006 | Blake et al. |
| 2006/0178741 A1 | 8/2006 | Zadno-Azizi et al. |
| 2006/0241752 A1 | 10/2006 | Israel |
| 2006/0259139 A1 | 11/2006 | Zadno-Azizi et al. |
| 2006/0271187 A1 | 11/2006 | Zadno-Azizi et al. |
| 2007/0005135 A1 | 1/2007 | Makker et al. |
| 2007/0027540 A1 | 2/2007 | Zadno-Azizi et al. |
| 2007/0050025 A1 | 3/2007 | Nguyen et al. |
| 2007/0078515 A1 | 4/2007 | Brady |
| 2007/0088433 A1 | 4/2007 | Esch et al. |
| 2007/0092830 A1 | 4/2007 | Lai et al. |
| 2007/0106377 A1 | 5/2007 | Smith et al. |
| 2007/0108643 A1 | 5/2007 | Zadno-Azizi et al. |
| 2007/0122540 A1 | 5/2007 | Salamone et al. |
| 2007/0201138 A1 | 8/2007 | Lo et al. |
| 2007/0203317 A1 | 8/2007 | Verbruggen et al. |
| 2007/0213817 A1 | 9/2007 | Esch et al. |
| 2007/0232755 A1 | 10/2007 | Matsushita et al. |
| 2007/0269488 A1 | 11/2007 | Ravi et al. |
| 2008/0001318 A1 | 1/2008 | Schorzman et al. |
| 2008/0003259 A1 | 1/2008 | Salamone et al. |
| 2008/0003261 A1 | 1/2008 | Schorzman et al. |
| 2008/0015689 A1 | 1/2008 | Esch et al. |
| 2008/0027461 A1 | 1/2008 | Vaquero et al. |
| 2008/0046074 A1 | 2/2008 | Smith et al. |
| 2008/0076897 A1 | 3/2008 | Kunzler et al. |
| 2008/0139769 A1 | 6/2008 | Iwamoto et al. |
| 2008/0143958 A1 | 6/2008 | Medina et al. |
| 2008/0181931 A1 | 7/2008 | Qiu et al. |
| 2008/0234457 A1 | 9/2008 | Zhou et al. |
| 2008/0300680 A1 | 12/2008 | Joshua et al. |
| 2008/0306587 A1* | 12/2008 | Your .................. A61L 27/16 522/182 |
| 2008/0306588 A1* | 12/2008 | Smiley .................. A61F 2/1629 623/6.13 |
| 2008/0314767 A1 | 12/2008 | Lai et al. |
| 2009/0043384 A1 | 2/2009 | Niwa et al. |
| 2009/0076603 A1 | 3/2009 | Avery et al. |
| 2009/0118739 A1 | 5/2009 | Kappelhof et al. |
| 2009/0143499 A1 | 6/2009 | Chang et al. |
| 2009/0168012 A1 | 7/2009 | Linhardt et al. |
| 2009/0170976 A1 | 7/2009 | Huang et al. |
| 2009/0171459 A1 | 7/2009 | Linhardt et al. |
| 2009/0204210 A1 | 8/2009 | Pynson |
| 2009/0232871 A1 | 9/2009 | Hitz et al. |
| 2009/0247661 A1 | 10/2009 | Müller-Lierheim et al. |
| 2009/0292355 A1 | 11/2009 | Boyd et al. |
| 2010/0016964 A1 | 1/2010 | Werblin |
| 2010/0119744 A1 | 5/2010 | Yokoyama et al. |
| 2010/0120938 A1 | 5/2010 | Phelan et al. |
| 2010/0120939 A1 | 5/2010 | Phelan et al. |
| 2010/0121444 A1 | 5/2010 | Ben Nun et al. |
| 2010/0160482 A1 | 6/2010 | Nachbaur et al. |
| 2010/0179653 A1 | 7/2010 | Argento et al. |
| 2010/0211170 A1 | 8/2010 | Liao et al. |
| 2010/0228346 A1 | 9/2010 | Esch et al. |
| 2010/0239633 A1 | 9/2010 | Strome et al. |
| 2010/0256651 A1 | 10/2010 | Jani et al. |
| 2010/0324674 A1 | 12/2010 | Brown et al. |
| 2011/0009519 A1 | 1/2011 | Awasthi et al. |
| 2011/0046332 A1 | 2/2011 | Breiner et al. |
| 2011/0112636 A1 | 5/2011 | Ben Nun |
| 2011/0118379 A1 | 5/2011 | Tighe et al. |
| 2011/0118834 A1 | 5/2011 | Lo et al. |

(56) References Cited

U.S. PATENT DOCUMENTS

| | | |
|---|---|---|
| 2011/0133350 A1 | 6/2011 | Qiu et al. |
| 2011/0140292 A1 | 6/2011 | Chang et al. |
| 2011/0144228 A1 | 6/2011 | Ravi et al. |
| 2011/0264209 A1 | 10/2011 | Wiechmann et al. |
| 2011/0269869 A1 | 11/2011 | Medina et al. |
| 2011/0282442 A1 | 11/2011 | Scholl et al. |
| 2011/0295368 A1 | 12/2011 | Betser et al. |
| 2012/0010321 A1 | 1/2012 | Chang et al. |
| 2012/0023869 A1 | 2/2012 | Samuel et al. |
| 2012/0033183 A1 | 2/2012 | Dai et al. |
| 2012/0041097 A1 | 2/2012 | Zhou et al. |
| 2012/0046743 A1 | 2/2012 | Pinchuk et al. |
| 2012/0063000 A1 | 3/2012 | Batchko et al. |
| 2012/0078363 A1 | 3/2012 | Lu |
| 2012/0078364 A1 | 3/2012 | Stenger |
| 2012/0088843 A1 | 4/2012 | Chang et al. |
| 2012/0088844 A1 | 4/2012 | Kuyu et al. |
| 2012/0088861 A1 | 4/2012 | Huang et al. |
| 2012/0115979 A1 | 5/2012 | Chang et al. |
| 2012/0147323 A1 | 6/2012 | Domschke et al. |
| 2012/0238857 A1 | 9/2012 | Wong et al. |
| 2012/0245684 A1 | 9/2012 | Liao et al. |
| 2012/0314183 A1 | 12/2012 | Nakamura et al. |
| 2012/0330415 A1 | 12/2012 | Callahan et al. |
| 2013/0013060 A1 | 1/2013 | Zadno-Azizi et al. |
| 2013/0053954 A1 | 2/2013 | Rao et al. |
| 2013/0095235 A1 | 4/2013 | Bothe et al. |
| 2013/0106007 A1 | 5/2013 | Medina et al. |
| 2013/0110234 A1 | 5/2013 | DeVita et al. |
| 2013/0116781 A1 | 5/2013 | Ben Nun et al. |
| 2013/0150961 A1 | 6/2013 | Evans et al. |
| 2013/0176628 A1 | 7/2013 | Batchko et al. |
| 2013/0197125 A1 | 8/2013 | Awasthi et al. |
| 2013/0224309 A1 | 8/2013 | Qiu et al. |
| 2013/0228943 A1 | 9/2013 | Qiu et al. |
| 2013/0245756 A1 | 9/2013 | Liao et al. |
| 2013/0289294 A1 | 10/2013 | Awasthi et al. |
| 2013/0304203 A1 | 11/2013 | Beer |
| 2013/0317607 A1 | 11/2013 | DeBoer et al. |
| 2014/0055750 A1 | 2/2014 | Dai et al. |
| 2014/0171539 A1 | 6/2014 | Chang et al. |
| 2014/0171542 A1 | 6/2014 | Chang |
| 2014/0178595 A1 | 6/2014 | Bothe et al. |
| 2014/0180403 A1 | 6/2014 | Silvestrini et al. |
| 2014/0180404 A1 | 6/2014 | Tran |
| 2014/0180406 A1 | 6/2014 | Simpson |
| 2014/0180407 A1 | 6/2014 | Sohn et al. |
| 2014/0228949 A1 | 8/2014 | Argento et al. |
| 2014/0277437 A1 | 9/2014 | Currie |
| 2014/0277439 A1 | 9/2014 | Hu et al. |
| 2014/0309735 A1 | 10/2014 | Sohn et al. |
| 2014/0316521 A1 | 10/2014 | McLeod et al. |
| 2014/0350124 A1 | 11/2014 | Chang et al. |
| 2014/0379079 A1 | 12/2014 | Ben Nun |
| 2015/0088149 A1 | 3/2015 | Auld |
| 2015/0092155 A1 | 4/2015 | Chang et al. |
| 2015/0105760 A1 | 4/2015 | Silvestrini et al. |
| 2015/0152228 A1 | 6/2015 | Chang et al. |
| 2015/0164321 A1 | 6/2015 | Weibel et al. |
| 2015/0173892 A1 | 6/2015 | Borja et al. |
| 2015/0177417 A1 | 6/2015 | Goshima et al. |
| 2015/0351901 A1 | 12/2015 | Chicevic et al. |
| 2016/0000558 A1 | 1/2016 | Honigsbaum et al. |
| 2016/0008126 A1 | 1/2016 | Vaughan et al. |
| 2016/0030161 A1 | 2/2016 | Rao et al. |
| 2016/0058553 A1* | 3/2016 | Salahieh ............... A61F 2/1629 623/6.13 |
| 2016/0074154 A1 | 3/2016 | Woods |
| 2016/0100938 A1 | 4/2016 | Hendrik et al. |
| 2016/0128826 A1 | 5/2016 | Rao et al. |
| 2016/0151150 A1 | 6/2016 | Sato |
| 2016/0184091 A1 | 6/2016 | Burns et al. |
| 2016/0184092 A1 | 6/2016 | Flaherty et al. |
| 2016/0250020 A1 | 9/2016 | Schieber et al. |
| 2016/0256265 A1 | 9/2016 | Borja et al. |
| 2016/0256316 A1 | 9/2016 | Van Noy et al. |
| 2016/0262875 A1 | 9/2016 | Smiley et al. |
| 2016/0278914 A1 | 9/2016 | Sato et al. |
| 2016/0296320 A1 | 10/2016 | Humayun et al. |
| 2016/0296662 A1 | 10/2016 | Miroslav et al. |
| 2016/0317286 A1 | 11/2016 | Rao et al. |
| 2016/0317287 A1 | 11/2016 | Rao et al. |
| 2016/0331587 A1 | 11/2016 | Ueno et al. |
| 2016/0361157 A1 | 12/2016 | Honigsbaum |
| 2017/0000602 A1 | 1/2017 | Sohn et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0119521 A1 | 5/2017 | Kahook et al. |
| 2017/0181850 A1* | 6/2017 | de Juan, Jr. ........... A61F 2/1635 |
| 2017/0258581 A1 | 9/2017 | Borja et al. |
| 2017/0348094 A1 | 12/2017 | Sohn et al. |
| 2018/0085213 A1 | 3/2018 | Hadba et al. |
| 2018/0110613 A1 | 4/2018 | Wortz et al. |
| 2018/0161152 A1 | 6/2018 | Argento et al. |
| 2018/0177589 A1 | 6/2018 | Argento et al. |
| 2019/0159890 A1 | 5/2019 | Salahieh et al. |
| 2019/0274823 A1 | 9/2019 | Argento et al. |
| 2019/0290422 A1 | 9/2019 | Ben Nun |
| 2019/0374334 A1 | 12/2019 | Brady et al. |
| 2020/0121447 A1 | 4/2020 | Argento et al. |
| 2020/0146813 A1 | 5/2020 | Argento et al. |
| 2020/0306031 A1 | 10/2020 | Salahieh et al. |
| 2020/0397566 A1 | 12/2020 | Salahieh et al. |
| 2021/0030529 A1 | 2/2021 | Adams et al. |
| 2021/0378815 A9 | 12/2021 | Salahieh et al. |
| 2022/0192818 A1 | 6/2022 | Raquet et al. |
| 2022/0273423 A1 | 9/2022 | Argento et al. |
| 2022/0296362 A1 | 9/2022 | Salahieh et al. |
| 2022/0338975 A1* | 10/2022 | Brady ................... A61F 2/1635 |
| 2022/0401213 A1 | 12/2022 | Argento et al. |
| 2023/0063391 A1 | 3/2023 | Scholl et al. |
| 2023/0200976 A1 | 6/2023 | Salahieh et al. |
| 2023/0263620 A1 | 8/2023 | Salahieh et al. |
| 2024/0050222 A1 | 2/2024 | Salahieh et al. |

FOREIGN PATENT DOCUMENTS

| | | |
|---|---|---|
| AU | 2010203427 | 5/2017 |
| AU | 2012335677 | 6/2017 |
| AU | 2015258287 | 12/2017 |
| CA | 2615825 | 1/2007 |
| CA | 2973684 | 7/2016 |
| CA | 2974639 | 8/2016 |
| CA | 2987311 | 12/2016 |
| CA | 2752046 | 4/2017 |
| CA | 2829143 | 4/2017 |
| CN | 1285722 | 2/2001 |
| CN | 1795090 | 6/2006 |
| CN | 101351169 | 6/2007 |
| CN | 101031257 | 9/2007 |
| CN | 101641060 | 11/2007 |
| CN | 101277659 | 10/2008 |
| CN | 101360468 | 2/2009 |
| CN | 101547663 | 9/2009 |
| CN | 101069106 | 2/2010 |
| CN | 102271623 | 7/2010 |
| CN | 103946251 | 7/2014 |
| CN | 104725553 | 6/2015 |
| CN | 108472129 | 8/2018 |
| CN | 107205815 | 8/2020 |
| EP | 0604369 A1 | 6/1994 |
| EP | 0734269 A1 | 10/1996 |
| EP | 0784652 A1 | 7/1997 |
| EP | 0800511 A1 | 10/1997 |
| EP | 0820601 A1 | 1/1998 |
| EP | 0826158 A1 | 3/1998 |
| EP | 0898972 A2 | 3/1999 |
| EP | 0907668 A1 | 4/1999 |
| EP | 0930357 A1 | 7/1999 |
| EP | 0604369 B1 | 8/1999 |
| EP | 0826158 B1 | 9/1999 |
| EP | 0947856 A2 | 10/1999 |
| EP | 0820601 B1 | 12/1999 |

(56) References Cited

FOREIGN PATENT DOCUMENTS

| | | |
|---|---|---|
| EP | 0800511 B1 | 1/2000 |
| EP | 0989138 A2 | 3/2000 |
| EP | 1084428 A1 | 3/2001 |
| EP | 1088246 A1 | 4/2001 |
| EP | 1090313 A1 | 4/2001 |
| EP | 1095711 A2 | 5/2001 |
| EP | 1095965 A1 | 5/2001 |
| EP | 1095966 A2 | 5/2001 |
| EP | 1109853 A1 | 6/2001 |
| EP | 0907668 B1 | 9/2001 |
| EP | 1141054 A1 | 10/2001 |
| EP | 1187873 A1 | 3/2002 |
| EP | 1200019 A1 | 5/2002 |
| EP | 1227773 A1 | 8/2002 |
| EP | 1230041 A2 | 8/2002 |
| EP | 1266246 A1 | 12/2002 |
| EP | 0898972 B1 | 4/2003 |
| EP | 1341485 A1 | 9/2003 |
| EP | 1364663 A1 | 11/2003 |
| EP | 1095711 B1 | 1/2004 |
| EP | 1141054 B1 | 2/2004 |
| EP | 1395302 A1 | 3/2004 |
| EP | 1410074 A1 | 4/2004 |
| EP | 1266246 B1 | 6/2004 |
| EP | 1109853 B1 | 9/2004 |
| EP | 1187873 B1 | 9/2004 |
| EP | 1084428 B2 | 11/2004 |
| EP | 1472305 A1 | 11/2004 |
| EP | 1230041 B1 | 12/2004 |
| EP | 0989138 B1 | 2/2005 |
| EP | 1095965 B1 | 2/2005 |
| EP | 1395302 B1 | 2/2005 |
| EP | 1507811 A1 | 2/2005 |
| EP | 1524953 A2 | 4/2005 |
| EP | 1200019 B1 | 9/2005 |
| EP | 1095966 B1 | 1/2006 |
| EP | 1660153 A2 | 5/2006 |
| EP | 1353611 B1 | 9/2006 |
| EP | 1696975 A1 | 9/2006 |
| EP | 1341485 B1 | 11/2006 |
| EP | 1723933 A2 | 11/2006 |
| EP | 1723934 A2 | 11/2006 |
| EP | 1750157 A1 | 2/2007 |
| EP | 1088246 B1 | 11/2007 |
| EP | 1857477 A1 | 11/2007 |
| EP | 1227773 B1 | 1/2008 |
| EP | 1888660 A2 | 2/2008 |
| EP | 1890650 A2 | 2/2008 |
| EP | 1902737 A1 | 3/2008 |
| EP | 1723933 B1 | 11/2008 |
| EP | 2035050 A2 | 3/2009 |
| EP | 2035480 A1 | 3/2009 |
| EP | 2035486 A1 | 3/2009 |
| EP | 1723934 B1 | 6/2009 |
| EP | 2066732 A2 | 6/2009 |
| EP | 2077292 A1 | 7/2009 |
| EP | 2092376 A1 | 8/2009 |
| EP | 1648534 B1 | 9/2009 |
| EP | 2094193 A2 | 9/2009 |
| EP | 2109784 A1 | 10/2009 |
| EP | 2120789 A2 | 11/2009 |
| EP | 2126614 A2 | 12/2009 |
| EP | 2035480 B1 | 2/2010 |
| EP | 2170708 A2 | 4/2010 |
| EP | 2178463 | 4/2010 |
| EP | 2185589 A2 | 5/2010 |
| EP | 2231207 A1 | 9/2010 |
| EP | 1750157 B1 | 10/2010 |
| EP | 2235094 A1 | 10/2010 |
| EP | 2276513 A2 | 1/2011 |
| EP | 2292672 A2 | 3/2011 |
| EP | 2356170 A1 | 8/2011 |
| EP | 2356497 A2 | 8/2011 |
| EP | 2109784 B1 | 10/2011 |
| EP | 2396355 A2 | 12/2011 |
| EP | 2035486 B1 | 4/2012 |
| EP | 2452212 A2 | 5/2012 |
| EP | 1857477 B1 | 6/2012 |
| EP | 1410074 B1 | 10/2012 |
| EP | 2092376 B1 | 10/2012 |
| EP | 2510051 A1 | 10/2012 |
| EP | 2513711 A1 | 10/2012 |
| EP | 2514791 A1 | 10/2012 |
| EP | 2356170 B1 | 12/2012 |
| EP | 2538266 A1 | 12/2012 |
| EP | 2563275 A1 | 3/2013 |
| EP | 2597113 A1 | 5/2013 |
| EP | 2598936 A1 | 6/2013 |
| EP | 2077292 B1 | 8/2013 |
| EP | 2625216 A1 | 8/2013 |
| EP | 2625217 A1 | 8/2013 |
| EP | 2625218 A1 | 8/2013 |
| EP | 2652532 A1 | 10/2013 |
| EP | 1830898 B1 | 3/2014 |
| EP | 2766750 A1 | 8/2014 |
| EP | 2452212 B1 | 3/2015 |
| EP | 2934383 A1 | 10/2015 |
| EP | 2200536 B1 | 1/2016 |
| EP | 2976042 A1 | 1/2016 |
| EP | 2979662 | 2/2016 |
| EP | 3185818 | 3/2016 |
| EP | 2129331 B1 | 4/2016 |
| EP | 3003217 A1 | 4/2016 |
| EP | 3025678 A1 | 6/2016 |
| EP | 2259750 B1 | 7/2016 |
| EP | 2934383 A4 | 7/2016 |
| EP | 3062741 A1 | 9/2016 |
| EP | 3072476 A1 | 9/2016 |
| EP | 1999188 B1 | 11/2016 |
| EP | 2685935 B1 | 11/2016 |
| EP | 2094193 | 1/2017 |
| EP | 2683287 | 2/2017 |
| EP | 3062742 | 2/2017 |
| EP | 3157466 | 4/2017 |
| EP | 3160404 | 5/2017 |
| EP | 3160683 | 5/2017 |
| EP | 3049023 | 6/2017 |
| EP | 3174500 | 6/2017 |
| EP | 3181094 | 6/2017 |
| EP | 2539351 | 7/2017 |
| ES | 2283058 T3 | 10/2007 |
| FR | 2653325 A1 | 4/1991 |
| JP | 59-501897 | 11/1984 |
| JP | 01-223970 | 9/1989 |
| JP | 2004502510 | 1/2004 |
| JP | 2006506196 | 6/2004 |
| JP | 2006518222 | 7/2004 |
| JP | 2002372688 | 12/2006 |
| JP | 2007-506516 | 7/2007 |
| JP | 2007-517616 | 7/2007 |
| JP | 2006516002 | 7/2008 |
| JP | 2010514507 | 7/2008 |
| JP | 2010-517639 | 5/2010 |
| JP | 2012-532685 | 12/2012 |
| JP | 2016-534816 | 11/2016 |
| WO | 9007545 A2 | 7/1990 |
| WO | 9007575 A1 | 7/1990 |
| WO | 9516475 A1 | 6/1995 |
| WO | 9611235 A1 | 4/1996 |
| WO | 9620919 A1 | 7/1996 |
| WO | 9631791 A1 | 10/1996 |
| WO | 9636890 A1 | 11/1996 |
| WO | 9749740 A1 | 12/1997 |
| WO | 9917684 A1 | 4/1999 |
| WO | 9929818 A1 | 6/1999 |
| WO | 9957581 A1 | 11/1999 |
| WO | 9960428 A1 | 11/1999 |
| WO | WO1999059668 | 11/1999 |
| WO | 9963366 A1 | 12/1999 |
| WO | 2000004078 A1 | 1/2000 |
| WO | 2000026980 A1 | 6/2000 |
| WO | 2000071613 A1 | 11/2000 |
| WO | 2001008607 A1 | 2/2001 |
| WO | 2001030512 A2 | 5/2001 |

(56) References Cited

FOREIGN PATENT DOCUMENTS

| | | |
|---|---|---|
| WO | 2001034067 A1 | 5/2001 |
| WO | 2001071392 A1 | 9/2001 |
| WO | 2002047583 A1 | 6/2002 |
| WO | WO2002074202 | 9/2002 |
| WO | 2002094331 A1 | 11/2002 |
| WO | 2003009014 A1 | 1/2003 |
| WO | 2003066707 A1 | 8/2003 |
| WO | 2003097711 A1 | 11/2003 |
| WO | 2004010905 A2 | 2/2004 |
| WO | 2004046768 A2 | 6/2004 |
| WO | 2004052242 A1 | 6/2004 |
| WO | 2004053536 A2 | 6/2004 |
| WO | 2004054471 A2 | 7/2004 |
| WO | 2004058318 A1 | 7/2004 |
| WO | 2004072689 A2 | 8/2004 |
| WO | 2005023331 A2 | 3/2005 |
| WO | 2005065734 A1 | 7/2005 |
| WO | 2006047383 A2 | 5/2006 |
| WO | 2006103674 A2 | 10/2006 |
| WO | 2006126095 A2 | 11/2006 |
| WO | 2007005778 A2 | 1/2007 |
| WO | WO2007005692 | 1/2007 |
| WO | 2007047529 A2 | 4/2007 |
| WO | 2007047530 A2 | 4/2007 |
| WO | 2007050394 A2 | 5/2007 |
| WO | 2007064594 A2 | 6/2007 |
| WO | 2008005644 A1 | 1/2008 |
| WO | 2008005652 A1 | 1/2008 |
| WO | 2008005752 A2 | 1/2008 |
| WO | 2008024766 A2 | 2/2008 |
| WO | 2008039655 A2 | 4/2008 |
| WO | 2008076729 A1 | 6/2008 |
| WO | 2008077040 A2 | 6/2008 |
| WO | 2008082957 A2 | 7/2008 |
| WO | 2008094876 A1 | 8/2008 |
| WO | 2008103798 A2 | 8/2008 |
| WO | 2008107882 A2 | 9/2008 |
| WO | 2008116132 A2 | 9/2008 |
| WO | 2008151088 A2 | 12/2008 |
| WO | 2009002703 A2 | 12/2008 |
| WO | WO2009002789 | 12/2008 |
| WO | 2009015161 A2 | 1/2009 |
| WO | 2009015226 A2 | 1/2009 |
| WO | 2009015234 A2 | 1/2009 |
| WO | 2009015240 A2 | 1/2009 |
| WO | 2009085755 A1 | 7/2009 |
| WO | 2009085756 A1 | 7/2009 |
| WO | 2009127844 A2 | 10/2009 |
| WO | 2010056686 A1 | 5/2010 |
| WO | 2010056687 A2 | 5/2010 |
| WO | 2010081093 A2 | 7/2010 |
| WO | 2010093823 A2 | 8/2010 |
| WO | 2011005937 A2 | 1/2011 |
| WO | 2011026068 A2 | 3/2011 |
| WO | 2011071790 A1 | 6/2011 |
| WO | 2011075377 A1 | 6/2011 |
| WO | 2011106435 A2 | 9/2011 |
| WO | 2012006616 A2 | 1/2012 |
| WO | 2012015639 A1 | 2/2012 |
| WO | 2012047961 A1 | 4/2012 |
| WO | 2012047964 A1 | 4/2012 |
| WO | 2012047969 A1 | 4/2012 |
| WO | 2012082704 A1 | 6/2012 |
| WO | 2012129407 A2 | 9/2012 |
| WO | WO2012129419 | 9/2012 |
| WO | 2013055746 A1 | 4/2013 |
| WO | WO2013059195 | 4/2013 |
| WO | 2013070924 A1 | 5/2013 |
| WO | 2013158942 A1 | 10/2013 |
| WO | 2013166068 A1 | 11/2013 |
| WO | 2014093751 A2 | 6/2014 |
| WO | 2014093764 A1 | 6/2014 |
| WO | 2014095690 A1 | 6/2014 |
| WO | 2014099630 A1 | 6/2014 |
| WO | 2014143926 A1 | 9/2014 |
| WO | 2014149462 A1 | 9/2014 |
| WO | 2014152017 A1 | 9/2014 |
| WO | WO2014134302 | 9/2014 |
| WO | WO2014152017 | 9/2014 |
| WO | 2015038620 A2 | 3/2015 |
| WO | 2015048279 A1 | 4/2015 |
| WO | 2015066502 A1 | 5/2015 |
| WO | 2015066532 | 5/2015 |
| WO | WO2015066502 | 5/2015 |
| WO | 2015148673 A1 | 10/2015 |
| WO | 2016018932 | 2/2016 |
| WO | 2016018932 A1 | 2/2016 |
| WO | 2016033217 A1 | 3/2016 |
| WO | 2016038470 A2 | 3/2016 |
| WO | 2016061233 A1 | 4/2016 |
| WO | 2016122805 A1 | 8/2016 |
| WO | 2016133558 | 8/2016 |
| WO | 2016140708 A1 | 9/2016 |
| WO | 2016195095 A1 | 12/2016 |
| WO | 2016201351 A1 | 12/2016 |
| WO | 2017079449 | 5/2017 |
| WO | 2017079733 | 5/2017 |
| WO | 2017087358 | 5/2017 |
| WO | WO2017084551 | 5/2017 |
| WO | 2017208230 | 12/2017 |
| WO | 2017223544 | 12/2017 |
| WO | WO2017221196 | 12/2017 |
| WO | 2018119408 | 6/2018 |
| WO | 2018222579 | 12/2018 |
| WO | 2018227014 | 12/2018 |
| WO | WO2019050690 | 3/2019 |
| WO | WO2020219456 | 10/2020 |
| WO | WO2021007535 | 1/2021 |
| WO | 2021158882 | 8/2021 |
| WO | WO2022220861 | 10/2022 |
| WO | WO2022226269 | 10/2022 |
| WO | WO2023084382 | 5/2023 |
| WO | WO2023141552 | 7/2023 |

OTHER PUBLICATIONS

Tsao et al. "Bonding of thermoplastic polymer microfluidics. Microfluid Nanofuild," 2009 6:1-16.

Umbrecht et al. "Solvent assisted bonding of polymethylmethacrylate: characterization using the response surface methodology" Jan. 2008, pp. 1325-1328.

Liang et al. "Bionic intraocular lens with variable focus and integrated structure" Optical Engineering 2015 vol. 54 No. 10 Article No. 105106 Internal pp. 1-7.

International Search Report and Written Opinion for PCT Application No. PCT/US2017/068226, filed Dec. 22, 2017, Applicant: Shifamed Holdings, LLC, Date of Mailing: Apr. 17, 2018, 15 pages.

English translation of First Chinese Office Action mailed Sep. 10, 2020 for Chinese Patent Application No. 201780087361.6, Applicant: Shifamed Holdings, LLC, filing date: Dec. 23, 2017, 11 pages.

International Search Report and Written Opinion for PCT Application No. PCT/US2022/025887, filed Apr. 22, 2022, Applicant: Shifamed Holdings, LLC, Date of Mailing: Aug. 11, 2022, 9 pages.

International Search Report and Written Opinion for PCT Application No. PCT/US2022/049046, filed Nov. 4, 2022, Applicant: Shifamed Holdings, LLC, Date of Mailing: Mar. 24, 2023, 13 pages.

\* cited by examiner

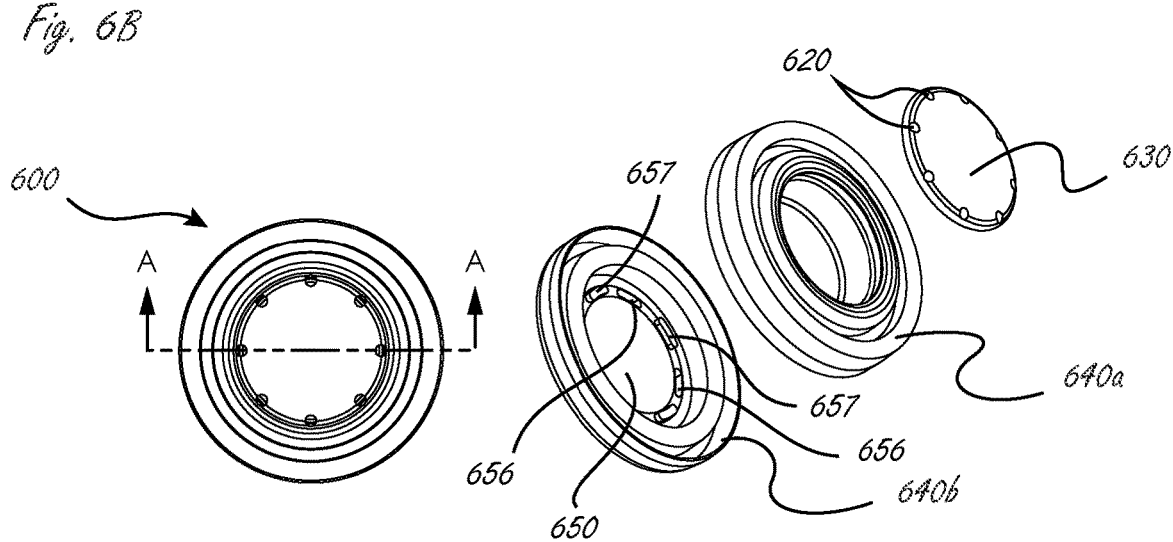
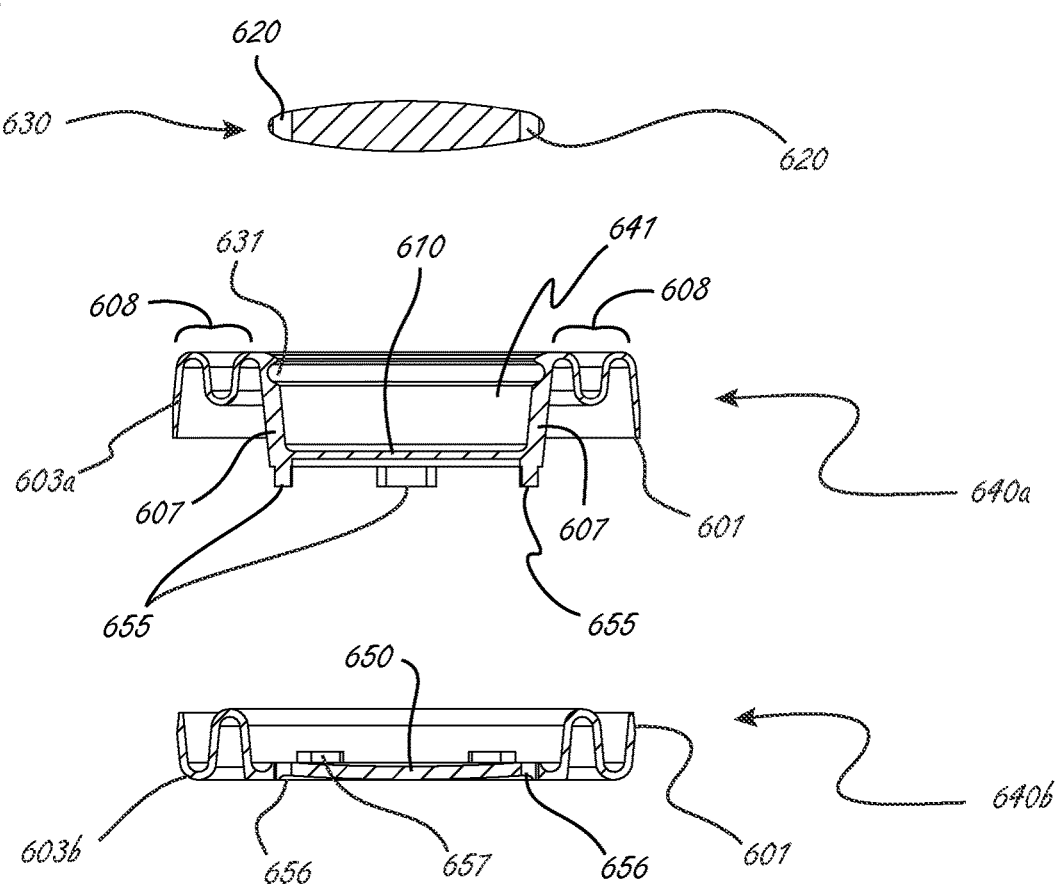

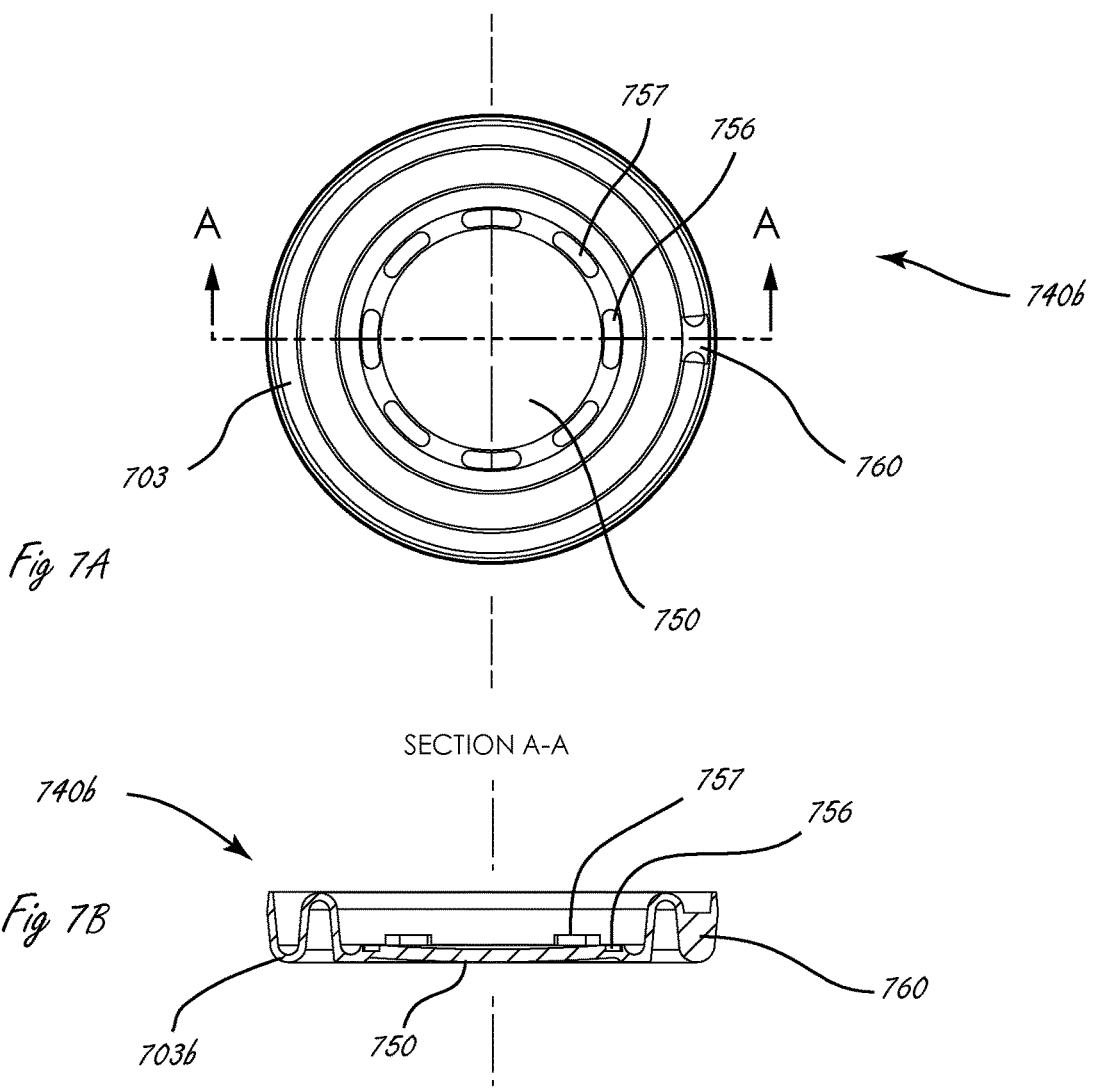
Fig 7A
SECTION A-A
Fig 7B
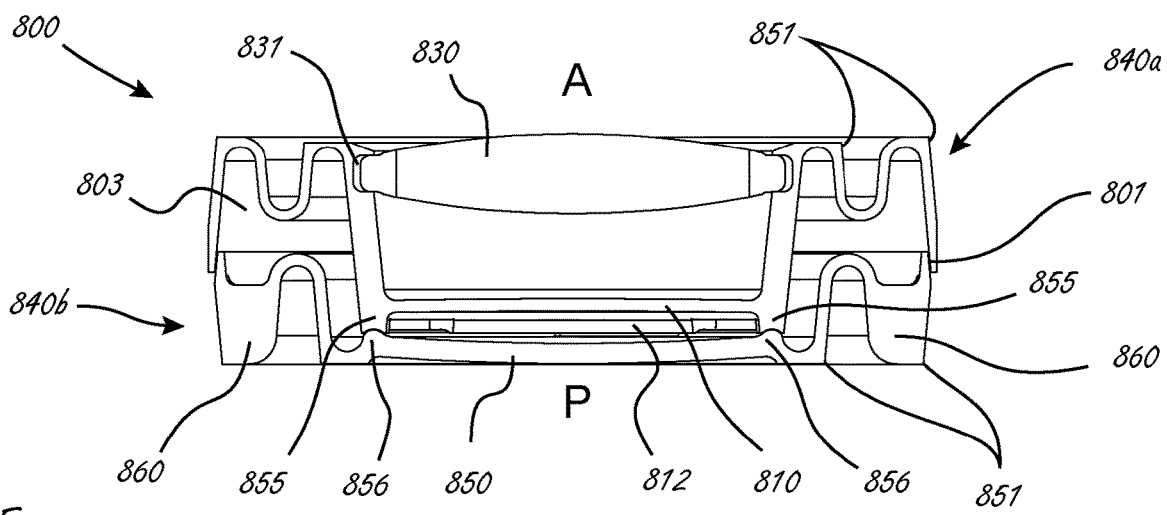
Fig. 8

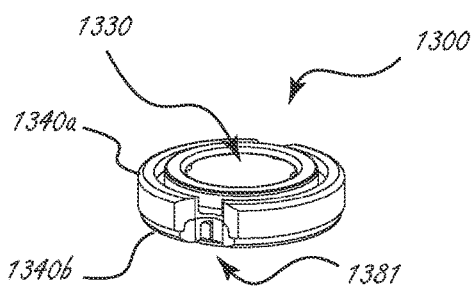
Fig. 13A
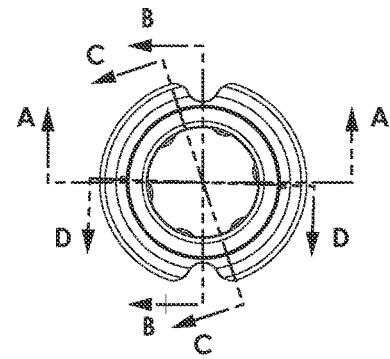
Fig. 13B
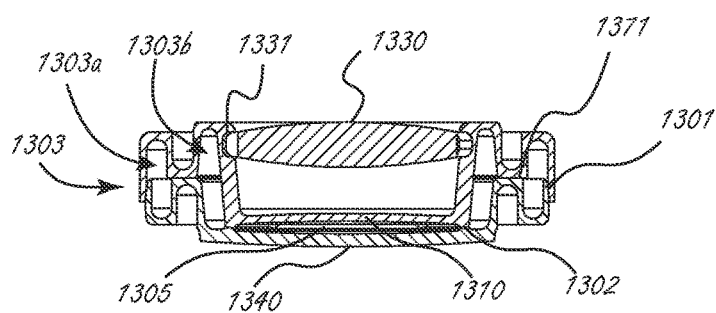
Fig. 13C  SECTION A-A
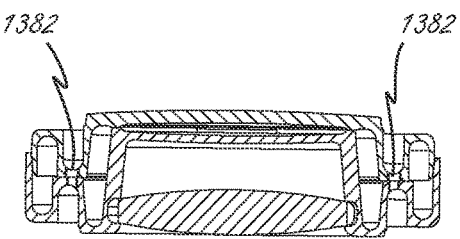
SECTION D-D
Fig. 13D
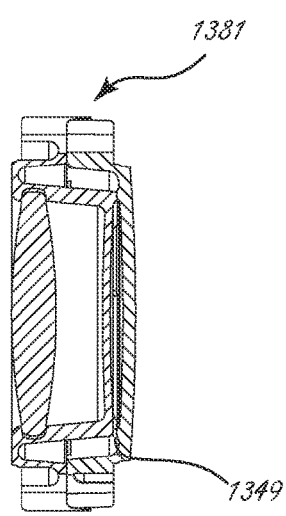
SECTION B-B
Fig. 13E
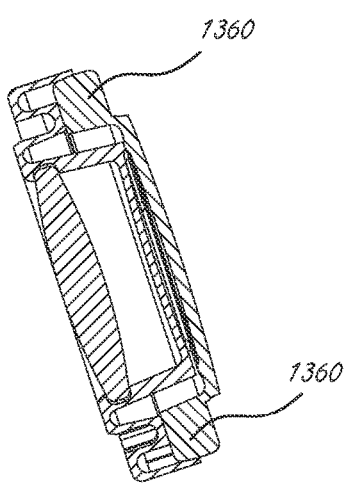
SECTION C-C
Fig. 13F

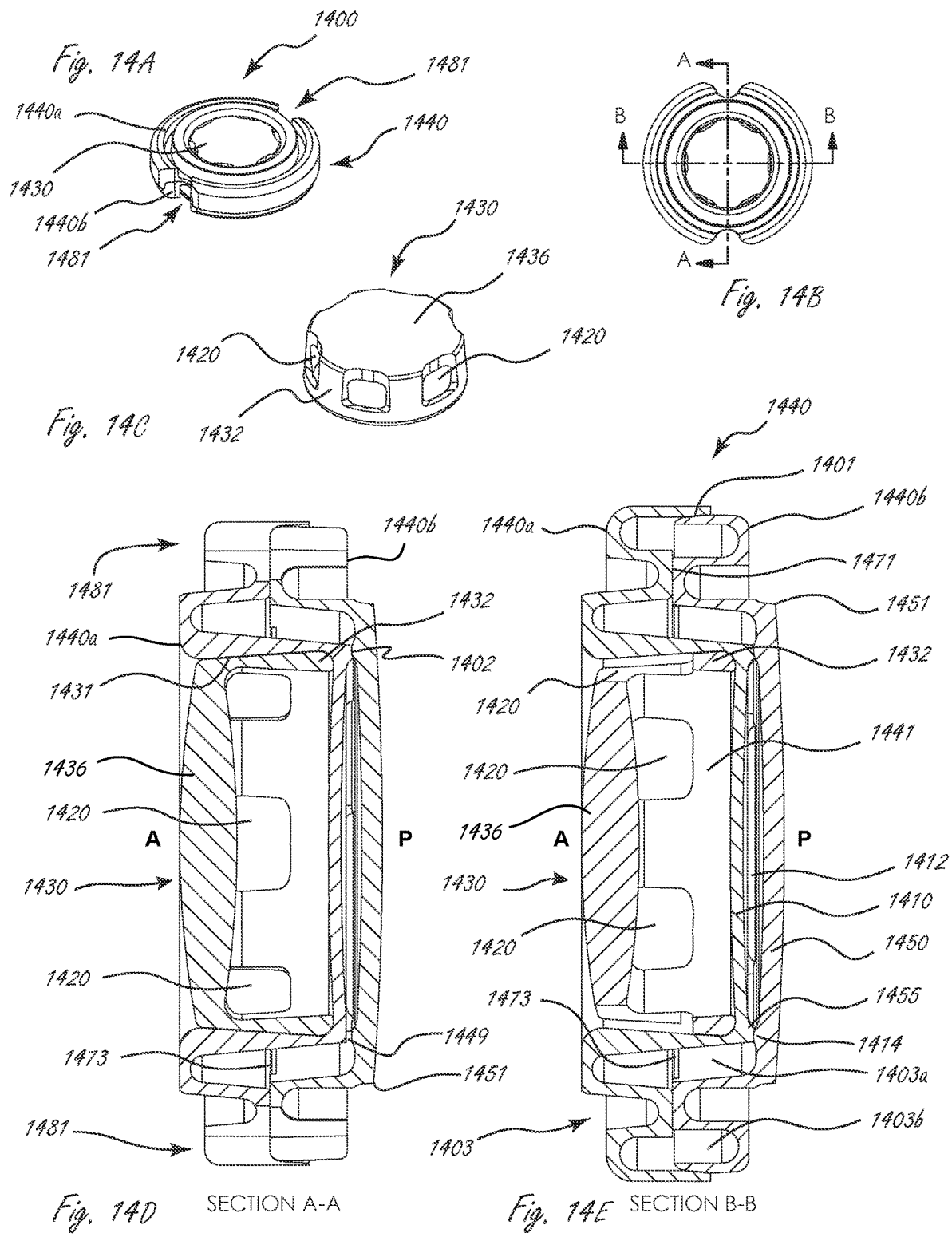

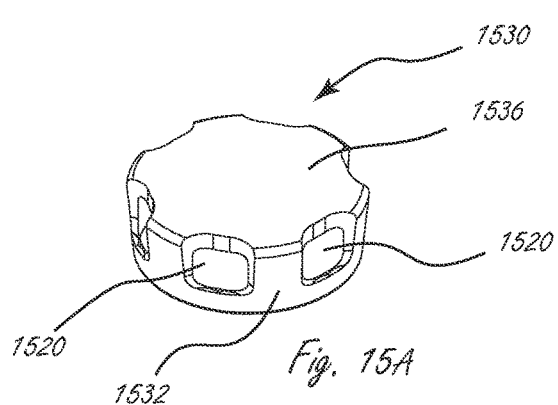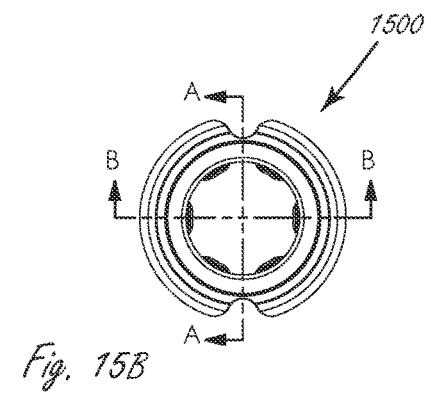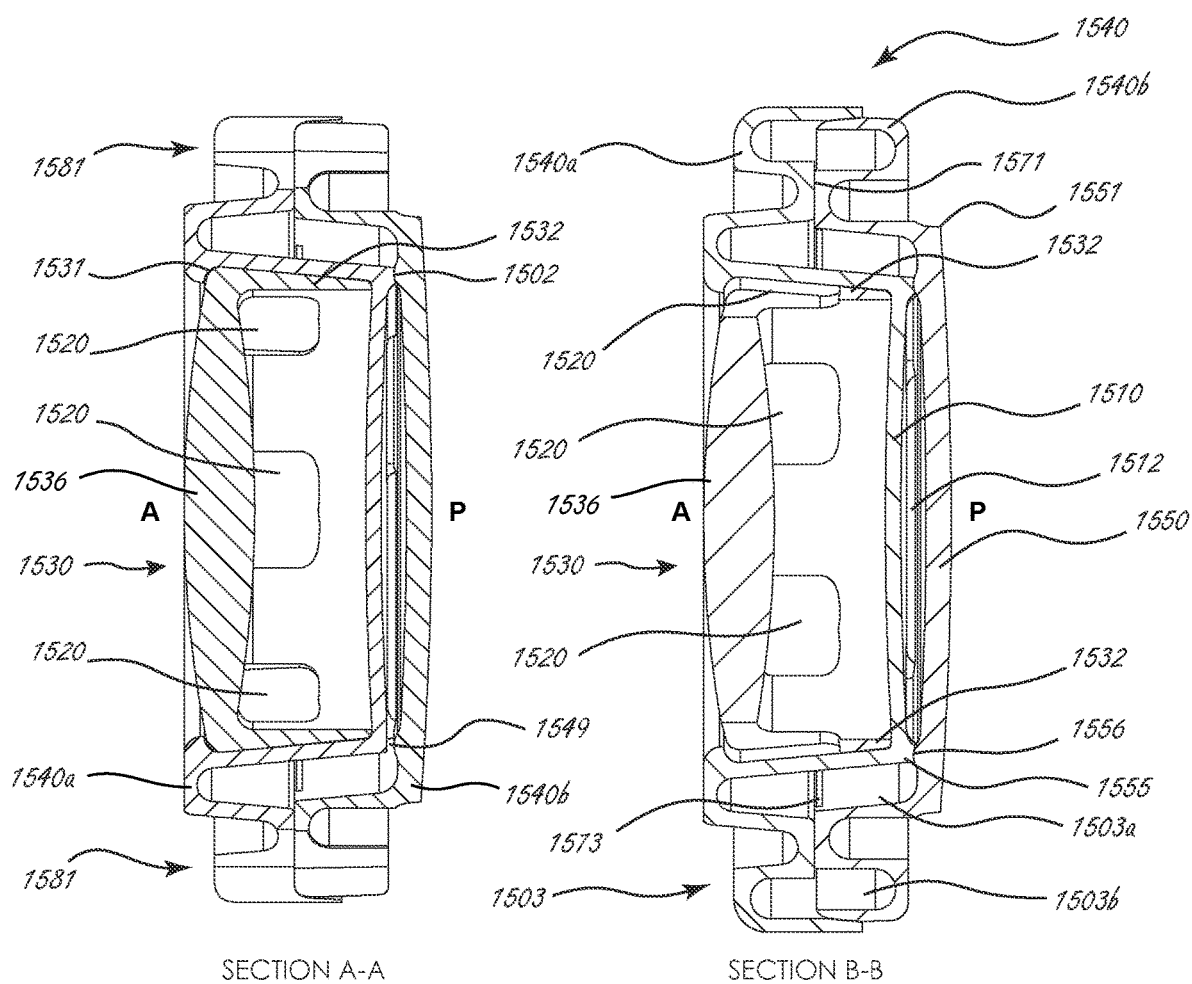
Fig. 15A  Fig. 15B
SECTION A-A  SECTION B-B
Fig. 15C  Fig. 15D

SECTION A-A

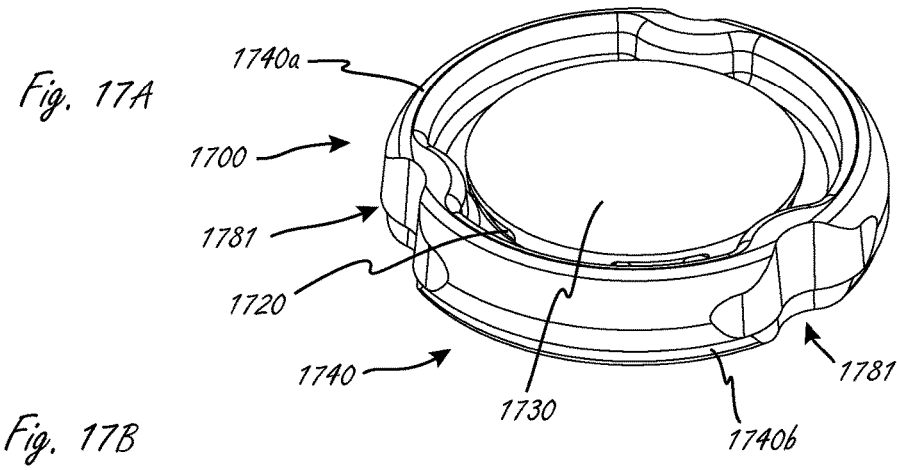
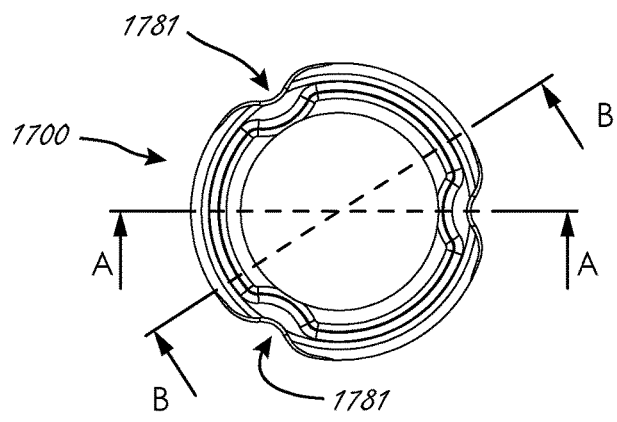
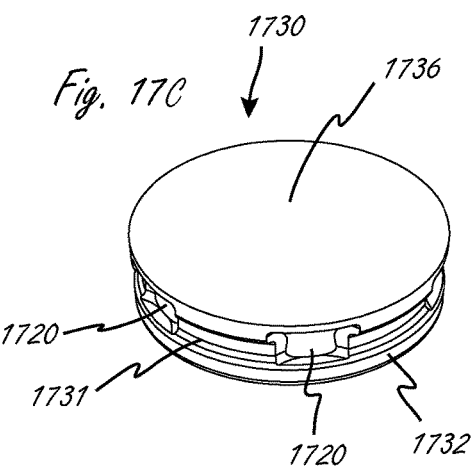
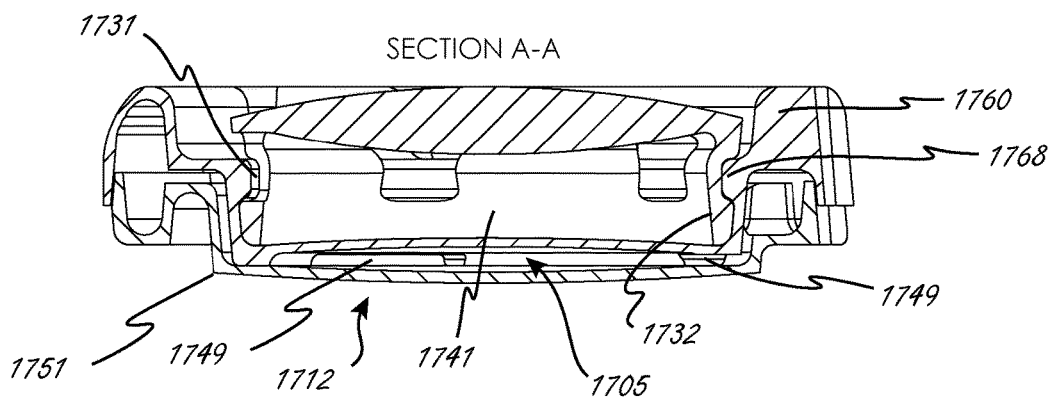

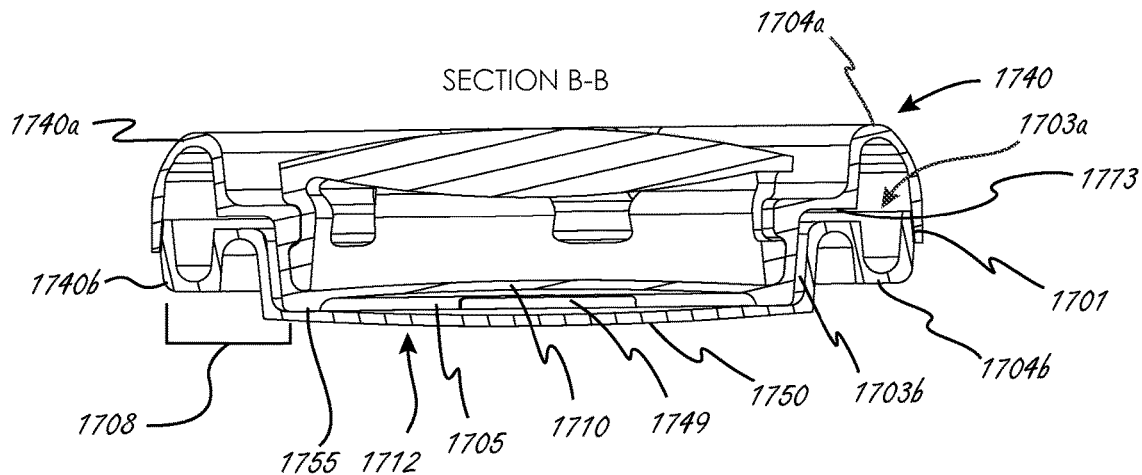
Fig. 17E
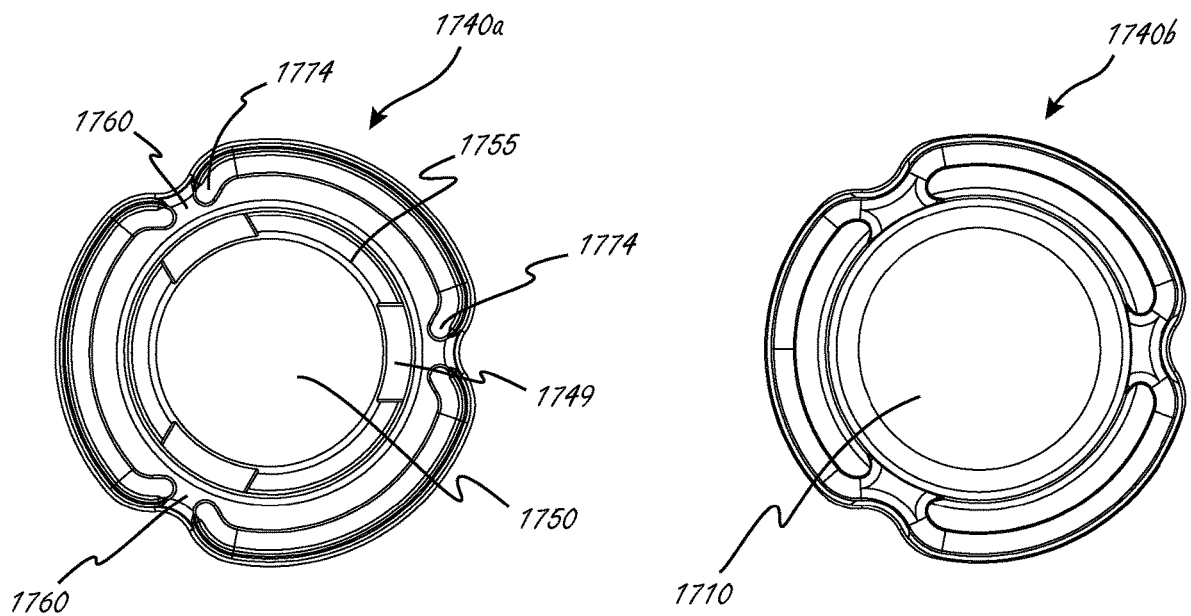
Fig. 17F
Fig. 17G

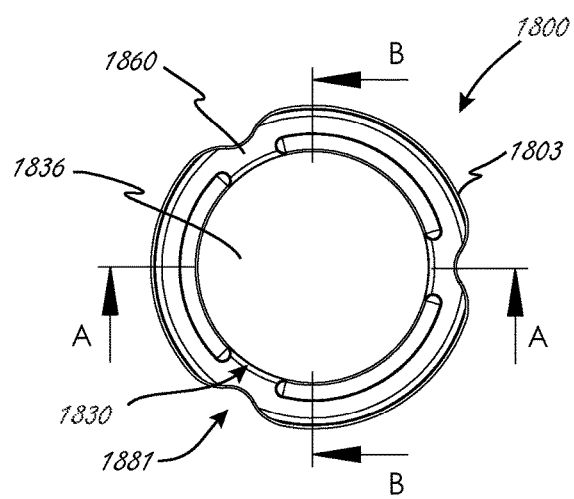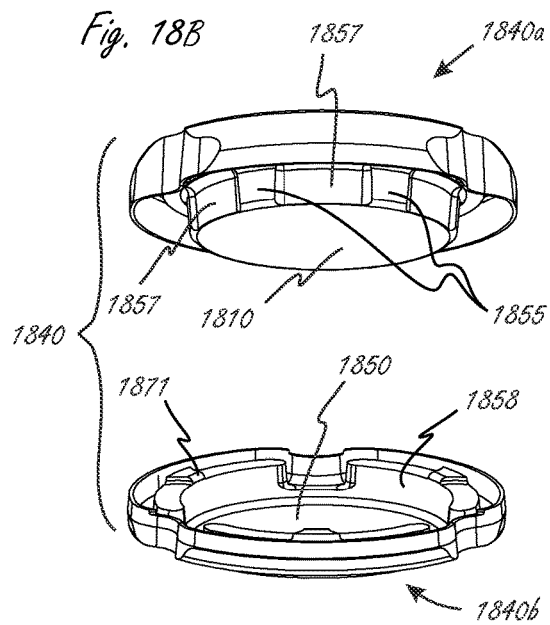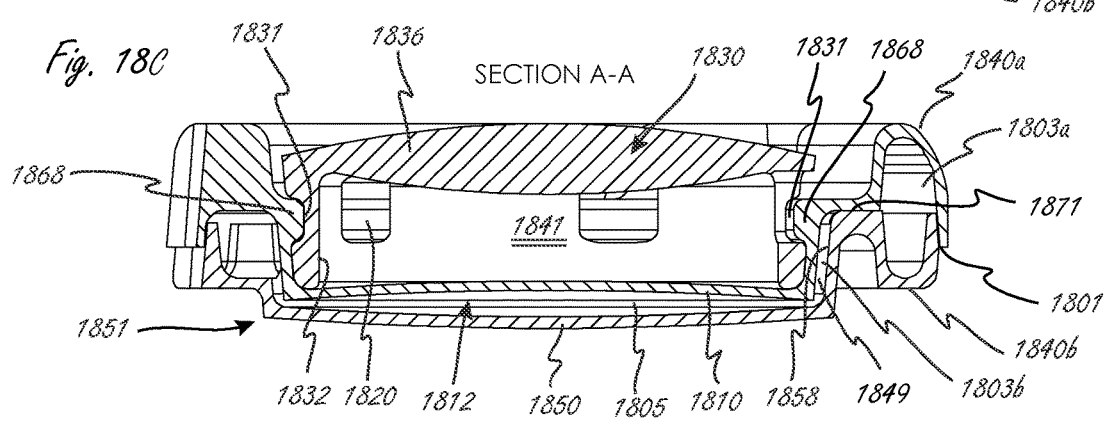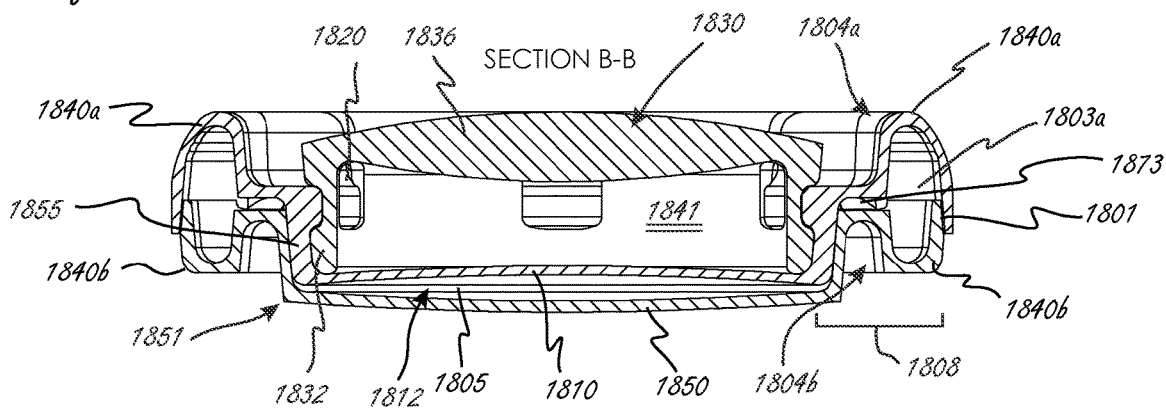

MULTI-PIECE ACCOMMODATING INTRAOCULAR LENSES AND METHODS FOR MAKING AND USING SAME

CROSS-REFERENCE TO RELATED APPLICATION(S)

This application is a continuation of U.S. patent application Ser. No. 16/426,211, filed May 30, 2019, entitled "MULTI-PIECE ACCOMMODATING INTRAOCULAR LENSES AND METHODS FOR MAKING AND USING SAME," which is a divisional of U.S. patent application Ser. No. 15/890,619, filed Feb. 7, 2018, now issued as U.S. Pat. No. 10,350,056, entitled "MULTI-PIECE ACCOMMODATING INTRAOCULAR LENSES AND METHODS FOR MAKING AND USING SAME," which is a continuation of International Patent Application No. PCT/US2017/068226, filed Dec. 22, 2017, which claims priority to U.S. Provisional Application No. 62/438,969, filed on Dec. 23, 2016, entitled "MULTI-PIECE ACCOMMODATING IOL," U.S. Provisional Application No. 62/544,681, filed on Aug. 11, 2017, entitled "MULTI-PIECE ACCOMMODATING IOL," and U.S. Provisional Application No. 62/549,333, filed on Aug. 23, 2017, entitled "MULTI-PIECE ACCOMMODATING IOL," the contents of which are hereby incorporated by reference in their entireties.

BACKGROUND

The present disclosure relates to medical devices and methods. In particular, the present disclosure relates to accommodating intraocular lenses (hereinafter "AIOLs" or "AIOL" for singular).

Cataracts can affect a large percentage of the worldwide adult population with clouding of the native crystalline lens and resulting loss of vision. Patients with cataracts can be treated by native lens removal and surgical implantation of a synthetic intraocular lens (IOL).

Worldwide, there are millions of IOL implantation procedures performed annually. In the US, there are 3.5 million cataract procedures performed, while worldwide there are over 20 million annual procedures performed.

Although IOL implantation procedures can be effective at restoring vision, conventional IOLs have several drawbacks. For example, many prior IOLs are not able to change focus as a natural lens would (known as accommodation). Other drawbacks of conventional IOLs include refractive errors that occur after implantation and require glasses for correcting distance vision, or in other cases the IOLs can be effective in providing good far vision but patients need glasses for intermediate and near vision.

Several multi-focal IOLs have been developed to address these drawbacks, but they too can have drawbacks. For example, although multi-focal IOLs generally perform well for reading and distance vision, in at least some instances such multi-focal IOLs may cause significant glare, halos, and visual artifacts.

AIOLs have been proposed to provide accommodative optical power in response to the distance at which a patient views an object. However, such AIOLs are generally still in development and have different drawbacks. For example, prior AIOLs can provide insufficient accommodation after implantation or produce suboptimal refractive correction of the eye. The amount of accommodation of the prior AIOLs can also decrease after implantation in at least some instances. The prior AIOLs can also be too large to be inserted through a small incision of the eye and may require the incision to be somewhat larger than would be ideal. Also, at least some of the prior AIOLs can be unstable when placed in the eye, which can lead to incorrect accommodation and other errors.

Improved implantable intraocular lenses that accommodate with the natural mechanisms of controlling focusing of the eye that overcome at least some of the above deficiencies would be desirable. Ideally, such improved AIOLs would provide increased amounts of accommodation when implanted, provide refractive stability, introduce few if any perceptible visual artifacts, and allow the optical power of the eye to change from far vision to near vision in response to the distance of the object viewed by the patient.

SUMMARY

Embodiments of the present disclosure provide improved AIOLs and methods for making and using AIOLs. In many embodiments, the AIOLs include an accommodating structure comprising an inner fluid chamber and an outer fluid reservoir disposed continuously circumferentially about the inner fluid chamber. The accommodating structure of the AIOLs can have an inner region, which is defined at least in part by the inner fluid chamber, that defines an optical structure having first and second optical components which provide optical power. The outer fluid reservoir may comprise a bellows fluidically coupled to the inner fluid chamber. The AIOLs provide optical power accommodation in one or more ways. For example, the bellows can have a compliant fold region that deflects when the eye accommodates for near vision and thereby transfers fluid between the outer fluid reservoir and the inner fluid chamber to change the profile of the inner region and cause optical power changes. At the periphery of the inner fluid chamber, a plurality of protrusions, such as posts or bumps, may (1) provide a predetermined amount of separation between the first and second optical components and (2) define one or more fluid channels between the inner fluid chamber and the outer fluid reservoir. Although the bellows can be configured in many ways, in many embodiments the bellows extend continuously and circumferentially around an optical axis of the AIOL, and one or more folds of opposing sides of the bellows can extend toward each other in a direction similar to the optical axis. The folds of the bellows may extend continuously and circumferentially substantially around the optical axis, such as three hundred and sixty (360) degrees around the optical axis.

Aspects of the present disclosure provide an AIOL for placement within a lens capsule of a subject. The AIOL may comprise a first component having the first optical component and a first bellows region, and a second component having the second optical component and a second bellows region. The second component is coupled to the first component. The inner fluid chamber can be formed between the first and second optical components. The outer fluid reservoir can be formed between the first bellows region and the second bellows region, and the outer fluid reservoir is in fluid communication with the inner fluid chamber. In operation, fluid transfers between the inner fluid chamber and the outer fluid reservoir in response to shape changes of the lens capsule thereby changing the shape of one or both of the first and second optical components for providing optical power changes to the AIOL.

Several embodiments of AIOLs also include a fixed lens coupled to the accommodating structure. The fixed lens can provide a base power to the AIOL, and in several embodiments the accommodating structure may not have a base power when in a relaxed condition (i.e., when no pressure is applied to the outer fluid reservoir). However, in some embodiments both the fixed lens and the accommodating structure may have the same or different base powers. The fixed lens may be coupled to the posterior side or the anterior side of the accommodating structure. In operation, the fixed lens can be selected to provide a desired base power of the AIOL, and the accommodating structure can then provide an adjustable power to the AIOL in response to the natural mechanisms of controlling focusing of the eye.

In several embodiments of the AIOLs, the fixed lens is coupled to the accommodating structure to be positioned anteriorly with respect to the first and second optical components that provide the accommodative optical power. In such embodiments, the fixed lens is spaced anteriorly apart from the first optical component to allow the first optical component to move anteriorly as fluid is driven from the outer fluid reservoir into the inner fluid chamber. Moreover, since the fixed lens is anterior of the first and second optical components, the fixed lens can be coupled to the accommodating structure after the accommodating structure has been implanted in the native eye capsule. The fixed lens can accordingly be selected to provide the desired refractive requirements for a specific patient after the accommodating structure has been implanted. This feature is useful because the optical properties of the accommodating structure may change after implantation, and it is the anterior orientation of the fixed lens that allows the appropriate fixed lens to be selected post-implantation based on the actual implanted optical properties of the accommodating structure.

Several embodiment of fixed lenses include additional features. For example, the fixed lens can include passages (e.g., holes or cutouts) that allow aqueous fluid to pass through the fixed lens, indexing features for accurately positioning toric or other asymmetrical lenses, engagement features and/or skirts. The engagement features are configured to provide secure attachment of the fixed lens to the accommodating structure, while also being detachable (e.g., a snap-fit or other type of interference fit). In several embodiments, the fixed lens has an optical portion that provides the optical properties to the fixed lens and a skirt extending posteriorly with respect to the optical portion. The skirt spaces the fixed lens apart from the first optical component by a desired distance. The skirt can also enhance to optical performance of the accommodating structure. For example, the skirt constrains the perimeter of the first optical component to prevent distortion that would otherwise occur as fluid moves to/from the inner fluid chamber. The skirt also defines the radius of the deformable area of the first optical component such that a given amount fluid causes greater accommodation than without the skirt. Additionally, the skirt provides an inner wall that buttresses the outer fluid reservoir such that more fluid is pumped from the outer fluid reservoir into the inner fluid chamber in response to the natural focusing mechanism of the eye than without the skirt.

Several embodiments of the present technology are directed to a kit having an accommodating structure and a first fixed lens that has no optical base power. The accommodating structure can be implanted into the native eye capsule, and then the first fixed lens can be coupled to the accommodating structure. The optical properties of the implanted accommodating structure can then be assessed in situ with the first fixed lens in place to determine the desired optical properties of the fixed lens. If the optical properties of the assembled accommodating structure and first fixed lens without a base power are appropriate, then the system can remain implanted without additional changes. However, if a different base power or some other optical property are desired (e.g., toric or other asymmetrical optics), then the first fixed lens without a base power can be replaced with a second fixed lens having the desired optical properties based on the optical properties of the implanted accommodating portion with a fixed lens attached. The kit can accordingly further include one or more second fixed lenses having various based powers or other optical properties.

In many embodiments, the first component is glued to the second component at a joint. Additionally, bumps or other spacers can be located on an inner surface of one or more of the first component or the second component to provide a gap between the first optical component and the second optical component. The first component can be glued to the second component at a joint extending circumferentially around the first component and the second component.

The first bellows region can extend continuously circumferentially around the first optical structure, and the second bellows region can extend continuously circumferentially around the second optical structure.

The first bellows region may comprise one or more folds extending continuously circumferentially around an optical axis of the first optical component, and the second bellows region may comprise one or more folds extending continuously circumferentially around an optical axis of the second optical component.

The first bellows region may comprise one or more first folds extending inwardly and continuously circumferentially around the first optical component, and the second bellows region may comprise one or more second folds extending inwardly and continuously circumferentially around the second optical component. Each of the first folds may extend toward a corresponding one of the second folds.

The first component may comprise a first annularly-shaped stiff coupling structure extending circumferentially between the first optical component and the first bellows region to inhibit radial movement of the first optical component with radial movement of the first bellows region. The second component may comprise a second annularly-shaped stiff coupling structure extending circumferentially between the second optical component and the second bellows region to inhibit radial movement of the second optical component with radial movement of the second bellows region. The first annularly-shaped structure may comprise a first radial thickness greater than a first thickness of the first bellows region, and the second annularly-shaped structure may comprise a second radial thickness greater than a second thickness of the second bellows region.

The first component may comprise an anterior component, and the second component may comprise a posterior component. The first component may comprise a first planar member, and the second component may comprise a second planar member. One or more of the first and second components may comprise a shell, such as a non-planar shell. One of the first or second components may comprise a planar member, and the other of the first or second components may comprise a plano-convex member shaped to provide an optical power.

The fluid within the inner fluid chamber may shape the inner fluid chamber so as to provide an optical power. For example, the shape of the volume of fluid in the inner fluid chamber may provide the optical power of the accommodating structure. Optical power changes to the AIOL may comprise a change to the optical power provided by the shape of the fluid within the inner fluid chamber. The change to the optical power provided by the shape of the fluid within the inner fluid chamber may comprise a change to a shape of the inner fluid chamber. Optical power changes to the AIOL may comprise a change to a separation distance between the first optical component and the second optical component. For example, the separation distance can be the distance between the centers of the first and second optical components measured along the optical axis.

Protrusions peripheral to edges of the first and second optical components and radially inward from the bellows regions may overlap and may be bonded with one another.

The outer fluid reservoir may comprise a bellows having a compliant fold region between inner and outer bellows regions. For example, the outer fluid reservoir can have a fold that defines the fold region, which in turn separates the inner bellows region from the outer bellows region. The compliant fold region may be thinner than the inner and outer bellows regions. The inner fluid chamber may be deflectable in response to deflection of the compliant fold region of the outer fluid reservoir. The compliant fold region may be thinner than the inner and outer bellows regions, which are located radially inward and radially outward with respect to the compliant fold region, respectively.

The AIOL may further comprise a plurality of protrusions, such as one or more of bumps and posts, coupled to one or more of the first and second components. The protrusions can separate portions of the first and second components from one another. For example, the plurality of protrusions may be disposed along outer edges of the inner portions of the first and second optical components to separate the first and second optical components from each other. The plurality of protrusions may define a plurality of fluid channels between the inner fluid chamber and the outer fluid reservoir, wherein each fluid channel is defined between two adjacent protrusions.

The protrusions can be located between the bellows and the optical components to connect the first component to the second component. The protrusions can be located on one or more stiff coupling structures of one or more of the first component and the second component to (a) provide the gap between the first optical component and the second optical component and (b) define a plurality of channels between the chamber and the reservoir to fluidically couple the reservoir to the chamber.

In many embodiments, the outer fluid reservoir comprises a compliant fold region between inner and outer bellows regions. The compliant fold region can be thinner than the inner and outer bellows regions.

In many embodiments, protrusions are coupled to the first or second components, and the protrusions separate the first and second optical components from one another. The protrusions can be disposed between the bellows and the inner region, and the space between protrusions can define fluid channels between the inner fluid chamber and the outer fluid reservoir. For example, each fluid channel is defined between two adjacent posts.

One or more of the first or second components may comprise a polymeric material such as a PMMA copolymer. The polymeric material may be water permeable. The polymeric material may be hydrophilic and/or a combination of both hydrophilic and hydrophobic materials. For example, when the polymeric material is both hydrophilic and hydrophobic components, the resulting polymeric material is predominantly hydrophilic. Water within the lens capsule of the subject may transfer into or out of one or more of the inner fluid chamber or the outer fluid reservoir through the polymeric material to achieve an osmotic equilibrium when the AIOL is placed within the lens capsule. The polymeric material may be non-permeable to compounds having a molecular weight of greater than 40 kDa, for example. AIOLs in accordance with the present technology may further comprise the fluid within the inner fluid chamber. The fluid may comprise one or more of a solution, an oil, a silicone oil, a solution of dextran, a solution of high molecular weight dextran, or a solution of another high molecular weight compound.

In many embodiments, the first and second components are sufficiently flexible to be folded into a reduced cross-section delivery configuration. The reduced cross-section delivery configuration may comprise one or more of folds or rolls of the intraocular lens around a delivery axis transverse to an optical axis of the accommodating intraocular lens. AIOL systems and/or kits in accordance with the present technology may comprise a delivery tube or aperture, and the reduced cross-section delivery configuration may comprise the intraocular lens advanced into the delivery tube or aperture.

In many embodiments, the outer fluid reservoir comprises a haptic structure to engage the lens capsule.

In many embodiments, the fluid within the inner fluid chamber has an index of refraction greater than an index of refraction of an aqueous humor of the eye of about 1.336.

In many embodiments, the first or second optical components provide no optical power without a fluid in the inner fluid chamber. In many embodiments, the fluid within the inner fluid chamber provides optical power.

In many embodiments, the first and second components are bonded to one another.

In many embodiments, both of the first and second components comprise the same polymer material, and the first and second components are bonded with a prepolymer of the polymer material.

In many embodiments one or more of the first component or the second component is directly fabricated, such as by three-dimensional (3D) printing.

In many embodiments, the first component and the second component are directly fabricated together and comprise a single piece.

In many embodiments, the first component and the second component are molded separately and bonded together.

In many embodiments, the first component and the second component are lathed separately and bonded together.

In many embodiments, the first component and the second component are bonded together at protrusions extending between the first component and the second component.

In many embodiments, the first component comprises a first fabricated part and the second component comprises a second fabricated part.

Aspects of the present disclosure provide a method of providing accommodation to an eye of a subject. A varying compressive force from the lens capsule may be received by the outer fluid reservoir of the accommodating intraocular lens placed within a lens capsule of the eye. A fluid may be urged between the outer fluid reservoir and the inner fluid chamber of the AIOL in response to received varying compressive force. The outer fluid reservoir can be a bellows comprising a fold extending continuously circumferentially around an optical axis of the intraocular lens. One or more of a size or shape of the inner fluid chamber may be changed in response to the fluid urged into or out of the inner fluid chamber to change an optical power of the accommodating intraocular lens.

In many embodiments, inner and outer bellows regions are in fluid communication with one another and the inner fluid chamber. One or more of the bellows regions can be annular, elliptical, and/or rotationally symmetric in shape.

In many embodiments, the outer fluid reservoir comprises a haptic structure to engage the lens capsule.

In many embodiments, changing one or more of the size or shape of the inner fluid chamber comprises changing a separation distance between portions of first and second optical components.

In many embodiments, changing one or more of the size or shape of the inner fluid chamber comprises changing a radius of curvature of one or more of the first or second optical components which define the inner fluid chamber.

In many embodiments, AIOLs comprise first and second optical components which define the inner fluid chamber, and one or more of the first or second optical components comprises a plano-convex member shaped to provide a minimum optical power to the accommodating intraocular lens. In other embodiments, at least one of the first and second optical components is a lens having an optical power comprising any suitable lens shape that produces an optical power.

In many embodiments, the inner fluid chamber contains a fluid therein such that the pressure of the fluid shapes the inner fluid chamber. The resulting shape of the fluid provides the optical power to the accommodating intraocular lens.

In many embodiments, increasing the varying compressive force urges fluid into the inner fluid chamber from the outer fluid reservoir.

Embodiments of the present disclosure provide improved AIOLs and methods for making and using AIOLs. Many embodiments of AIOLs in accordance with the present technology comprise an optical structure comprising a stiff member and a deflectable member (e.g., a deformable member) coupled to a haptic structure. The stiff member and the deflectable member can substantially define an inner fluid chamber of the AIOL. The inner fluid chamber of the AIOL can be filled with a fluid having an index of refraction greater than the aqueous humor of the eye such that the deflectable member defines a convexly curved surface of the volume of the fluid in order to provide a fluid lens having adjustable optical power. The deflectable member and stiff member may be coupled to the haptic structure in order to deflect the profile of the deflectable member to a convexly curved profile when the eye accommodates for near vision.

In many embodiments, the stiff member comprises a lens such as a plano-convex lens having an optical power configured to treat far vision of the patient. When the eye accommodates, the deflectable portion provides additional optical power for near vision. In many embodiments, the diameter of the lens of the stiff member corresponds to the diameter of the inner portion of the deflectable member, such that the diameter of the lens of the stiff member is sized smaller than the outer portion of the deflectable member, in order to decrease the thickness profile of the AIOL when inserted into the eye.

In many embodiments, an accommodating IOL comprises a first component and a second component each composed of a polymer, and an adhesive comprising the polymer. Alternatively, or in combination, the first component can be affixed to the second component with mechanical coupling such as interlocking joints, threads, mounts or fasteners. In many embodiments, the polymer can be hydrated and swells with hydration, such that the first component, the second component, and the adhesive swell together (e.g., at the same or substantially similar rate). By swelling together, stresses among the first component, the second component, and the adhesive can be inhibited substantially. Also, the hydratable adhesive allows the first and second components to be machined when they are less than fully hydrated and stiff (i.e., a stiff configuration) prior to adhering of the components together. The stiff configuration may comprise a less than fully hydrated polymer, such as a substantially dry polymer. The components can be bonded together in the substantially stiff configuration to facilitate handling during manufacturing, and subsequently hydrated such that the components bonded by the adhesive comprise a soft hydrated configuration for insertion into the eye. The adhesive comprising the polymer can bond the first and second lens components together with chemical bonds similar to the polymer material itself in order to provide increased strength. For example, the "chemical bonds" can be the same cross links as those of the polymer material.

In another aspect of the disclosure, an intraocular lens is provided. The intraocular lens may comprise an optical structure having an optical power and comprising a deflectable member, a stiff member, and a fluid chamber defined at least partially between the deflectable member and the stiff member. The intraocular lens may comprise a haptic structure coupled to a peripheral region of the stiff member and comprising an anterior element, a posterior element, and a fluid reservoir defined at least partially between the anterior element and the posterior element. The fluid reservoir may be in fluid communication with the fluid chamber with one or more channels. In many embodiments, a volume of the fluid chamber may increase in response to the decrease in the volume of the fluid reservoir to change the optical power. A shape of the fluid-filled chamber may change in response to the increase in the volume of the lens fluid chamber to change the optical power.

In another aspect of the disclosure, an intraocular lens comprises an optical structure comprising a posterior member, an anterior member, and a fluid-filled chamber between the posterior and anterior members. The intraocular lens may include a haptic structure interlocking peripheral regions of the posterior and anterior members to inhibit leakage of a fluid into and out of the fluid-filled haptic chamber. In many embodiments, the interlocking regions may comprise a fluid tight seal to inhibit leakage of the fluid. The haptic structure may have a first side having one or more male members and a second side having one or more female members. The one or more male members may pass through the peripheral regions of the posterior and anterior members to be received by the one or more female members to interlock the peripheral regions. The peripheral regions of the posterior and anterior members may have one or more apertures through which the one or more members pass through. The peripheral regions of one or more of the posterior or anterior members may have one or more male members to be received by one or more female members of the haptic structure to interlock the peripheral regions. The interlocking of the peripheral regions of the posterior and anterior members by the haptic structure may be maintained as the intraocular lens is deformed to change an optical power of the optical structure and/or folded or rolled into a delivery configuration.

In yet another aspect of the disclosure, an AIOL comprises an optical structure comprising a posterior member, an anterior member, and a fluid-filled chamber between the posterior and anterior members providing an optical power. The intraocular lens may comprise a haptic structure coupled to the optical structure. One or more of a shape or volume of the fluid-filled chamber may be configured to change in response to a radial force exerted on the haptic structure. The change of one or more of the shape or volume of the fluid-filled chamber may change the optical power of the fluid-filled chamber while leaving optical powers provided by the posterior and anterior members substantially unchanged.

In another aspect of the disclosure, a method of providing accommodation to an eye of the patient is provided. The method may comprise placing an AIOL within a lens capsule of the eye. One or more of a shape or volume of a fluid-filled chamber of the intraocular lens may be changed to change an optical power of the fluid-filled chamber while leaving optical powers provided by the posterior and anterior members substantially unchanged.

In many embodiments, the deflectable optical members as described herein have the advantage of deflecting while substantially maintaining a thickness of the optical member in order to inhibit optical aberrations when the member deflects.

An aspect of the disclosure provides an intraocular lens for implantation within a lens capsule of a patient's eye. The intraocular lens may comprise an optical structure and a haptic structure. The optical structure may have a peripheral portion and may comprise a planar member, a plano-convex member coupled to the planar member at the peripheral portion, and a fluid optical element defined between the planar member and the plano-convex member. The fluid optical element may comprise a fluid having a refractive index similar to either or both the materials comprising the planar member and the plano-convex member. For example, the refractive index of the fluid can be greater than the native aqueous fluid of the eye. The haptic structure may couple the planar member and the plano-convex member at the peripheral portion of the optical structure. The haptic structure may comprise a fluid reservoir in fluid communication with the fluid optical element and a peripheral structure for interfacing to the lens capsule. Shape changes of the lens capsule may cause one or more of volume or shape changes to the fluid optical element in correspondence to deformations of the planar member to modify the optical power of the fluid optical element. For example, shape changes of the lens capsule may cause the haptic structure to exert a mechanical force on the planar member to deform the member and correspondingly modify the optical power of the fluid optical element. Such deformations of the planar member may in some cases cause no change to the optical power of the planar member, the plano-convex member, or both (i.e., the change in optical power may solely be provided by one or more of the shape or volume changes to the fluid optical element and optionally changes to the anterior-posterior position of the intraocular lens within the lens capsule.)

A force imposed on the haptic fluid reservoir may deform the haptic fluid reservoir to modify the optical power of the fluid optical element. The force imposed on the haptic fluid reservoir may transfer fluid into or out of the fluid optical element from the haptic fluid reservoir to reversibly deform the haptic fluid reservoir.

In many embodiments, volume changes to the fluid optical element are provided by a fluid contained in the haptic fluid reservoir. In many embodiments, fluid transfer into or out of the fluid optical element leaves the plano-convex member un-deformed. The plano-convex member may comprise a stiff member and the planar member may comprise a deflectable member. In these embodiments, the fluid optical element may provide a majority of the optical power of the intraocular lens. Fluid within the fluid optical element and within the fluid reservoir of the haptic structure may have a refractive index of greater than or equal to 1.33.

The fluid within the fluid optical element and the fluid reservoir of the haptic structure may comprise oil such as a silicone oil or a solution such as a high molecular weight dextran. The fluid can be provided with a suitable index of refraction. For example, the high molecular weight dextran configured with a suitable index of refraction greater than 1.33 and an osmolality similar to the aqueous humor of the eye. The high molecular weight dextran may also have a mean molecular weight of at least 40 kDa, and the mean molecular weight can be within a range from about 40 kDa to about 2000 kDa, with intermediate ranges having upper and lower values defined with any of 40 kDa, 70 kDa, 100 kDa, 1000 kDa, or 2000 kDa. The high molecular weight dextran may comprise a distribution of molecular weights, and the distribution of molecular weights can be narrow or broad. As the index of refraction can be determined based on the weight of dextran per volume and the osmolality by the number of solute particles per volume, the mean molecular weight and amount of dextran can be used to configure the dextran solution with the appropriate index of refraction and osmolality.

In many embodiments, the haptic structure is configured to orient the intraocular lens in place within the lens capsule of the patient's eye. In many embodiments, the haptic structure comprises an anterior haptic structure and a posterior haptic structure that are coupled together to define the outer fluid reservoir therebetween. In many embodiments, the haptic structure comprises an annular structure coupled to the peripheral region of the optical structure. The haptic structure may comprise a plurality of tab structures coupled to and distributed over the peripheral portion of the optical structure.

The peripheral portion may comprise a plurality of apertures and the haptic structure may be coupled to the peripheral portion through the plurality of apertures. The plurality of apertures may be oriented substantially parallel to the optical axis of the intraocular lens. Alternatively, or in combination, the plurality of apertures may be oriented transverse to the optical axis of the intraocular lens. The haptic structure may comprise one or more posts or other structures for placement through the plurality of apertures of the peripheral portion of the optical structure to couple the haptic structure to the peripheral portion. Alternatively, or in combination, the optical structure may comprise posts for mating with structures such as apertures in the haptic structures.

The AIOLs may be sufficiently flexible to be folded into a reduced cross-section delivery configuration. The reduced cross-section delivery configuration of the AIOLs may be attained by folding or rolling the AIOLs around a delivery axis normal to an optical axis AIOLs. Alternatively, or in combination, the reduced cross-section delivery configuration of the AIOLs may be attained by advancing the intraocular lens through a delivery tube or aperture.

In many embodiments, the planar member is posterior of the plano-convex member when the AIOL is placed in the lens capsule.

Another aspect of the disclosure provides a method of providing accommodation in an eye of a patient. First, an AIOL is provided. The provided AIOL may comprise an optical structure and a haptic structure, and the optical structure can have a peripheral portion. The optical structure may comprise a first optical element (e.g., a planar member), a second optical element (e.g., a plano-convex member) coupled to the first optical element at the peripheral portion, and a fluid optical element defined between the first and second optical elements. The fluid optical element may comprise a fluid having a refractive index similar to either or both the materials of the first and second optical elements. The fluid optical element may have an optical power. The haptic structure may couple the first and second optical elements together at the peripheral portion of the optical structure. The haptic structure may comprise a fluid reservoir in fluid communication with the fluid optical element and a peripheral structure for interfacing to the lens capsule. Second, the AIOL may be folded into a reduced profile configuration. Third, the folded AIOL may be implanted into a lens capsule of the patient's eye. The folded AIOL reverts into a working configuration from the reduced profile configuration when implanted into the lens capsule. Fourth, one or more of the optical structure or the haptic structure may be actuated to cause one or more of volume or shape changes to the fluid optical element in correspondence to deformations in the planar member to modify the optical power of the fluid optical element.

One or more of the optical or haptic structure may be actuated by radially directing a force on the haptic structure to deform the planar member to modify the optical power of the fluid optical element. The haptic peripheral structure may be stiffly coupled to the substantially planar member of the optical structure. The change in optical power of the fluid optical element may be accompanied by a transfer of fluid into or out of the fluid optical element from the fluid reservoir of the haptic structure. Transfer of fluid into or out of the fluid optical element from the haptic fluid chamber may deflect the planar member while leaving the plano-convex member un-deflected. In alternative embodiments, transfer of fluid into or out of the fluid optical element from the haptic fluid chamber may deflect the planar member and optionally also the plano-convex member.

One or more of the optical structure and the haptic structure may be actuated by imposing a force on the haptic fluid reservoir to reversibly deform the haptic fluid reservoir to modify the optical power of the fluid optical element.

In many embodiments, the peripheral portion of the optical structure comprises a plurality of apertures and the haptic structure couples the posterior and anterior members together at the peripheral portion of the optical structure through the plurality of apertures. The haptic structure coupled to the plurality of apertures of the peripheral portion may maintain the substantially planar and plano-convex members coupled together as the intraocular lens is folded and during function or operation of the intraocular lens. The plurality of apertures may be oriented substantially parallel to the optical axis of the intraocular lens. The plurality of apertures may be oriented transverse to the optical axis of the intraocular lens. The haptic structure may comprise one or more posts for placement through the plurality of apertures to couple the haptic structure to the peripheral region. Alternatively, or in combination, the peripheral portion of the optical structure may have one or more apertures through which one or more posts of the haptic structure can pass through to couple the optical and haptic structures together.

The AIOLs may have reduced profile configuration by folding or rolling the AIOLs around a delivery axis normal to an optical axis of the lens. Alternatively, or in combination, the AIOLs may be folded into the reduced profile configuration by advancing the intraocular lens through a delivery tube or aperture.

The folded AIOLs may be implanted into the lens capsule by allowing the fluid within the lens fluid chamber to reach an osmotic equilibrium with fluid present in the lens capsule. One or more of the planar or plano-convex members may be water permeable to allow the osmotic equilibrium to be reached. In many embodiments, the porous posterior or anterior member is non-permeable to compounds having a molecular weight of greater than 40 kDa.

In many embodiments, one or more of the planar or plano-convex members has substantially no optical power.

In many embodiments, the planar member is posterior of the plano-convex member when the intraocular lens is placed in the lens capsule.

In another aspect, embodiments provide a method of manufacturing AIOLs by providing a first component comprising a polymer, and a second component comprising the same polymer. The first component is bonded to the second component with an adhesive. The adhesive may comprise a prepolymer of the polymer of the first and second components. For example, the prepolymer can be any individual species of the polymers comprising the first and second components, or any combination thereof, as monomers, short chain multimers, and/or partially polymerized.

In many embodiments, the prepolymer is cured to bond the first component to the second component with the polymer extending between the first component and the second component.

In many embodiments, the first component and the second component each comprise a stiff configuration when the first component is bonded to the second component with the polymer extending between the first component and the second component.

In many embodiments, the first component, the second component and the cured adhesive are hydrated to provide a hydrated, soft accommodating intraocular lens.

In many embodiments, hydrating the first component, the second component and the adhesive comprises fully hydrating the polymer of each of the first and second components and the adhesive to an amount of hydration corresponding to an amount of hydration of the polymer when implanted. In several embodiments, the adhesive is indistinguishable from the base polymer upon being cured.

In many embodiments, each of the first component, the second component and the cured adhesive each comprise a first configuration prior to hydration (e.g., stiff configuration) and second configuration when hydrated (e.g., soft configuration), and wherein each of the first component, the second component, and the cured adhesive expand a substantially similar amount from the first configuration to the second configuration in order to inhibit stress at interfaces between the adhesive and the first and second components.

Many embodiments further comprise providing the polymer material and shaping the first component and the second component from the polymer material.

In many embodiments, the first component and the second component are each turned on a lathe when stiff in order to shape the first component and the second component.

In many embodiments, the first component and the second component are molded.

In many embodiments, the prepolymer comprises one or more of a monomer, an oligomer, a partially cured monomer, particles, or nano-particles of the polymer.

In many embodiments, the first component comprises a disc shaped structure and the second component comprises a disc shaped structure and wherein the first component and the second component define a chamber with the disc shaped structures on opposite sides of the chamber when bonded together.

In many embodiments, one of the first component or the second component comprises a groove sized and shaped to receive the other of the first or second component and wherein the adhesive is placed on the groove.

In many embodiments, one or more of the first component or the second component comprises an annular structure extending between a first disc structure and a second disc structure in order to separate the first disc structure from the second disc structure and define a side wall of the chamber.

In another aspect, AIOLs comprise a first component, a second component, and an adhesive. The first component comprises a polymer material. The second component comprises the same polymer material. A cured adhesive comprises the polymer between at least a portion of the first component and the second component in order to bond the first component to the second component and define a chamber.

In many embodiments, the inner fluid chamber comprises an optical element. Many embodiments further comprise a fluid within the inner fluid chamber having an index of refraction greater than an index of refraction of an aqueous humor of an eye of about 1.336, and wherein one or more of the first component or the second component is configured to deform to increase an optical power of the accommodating intraocular lens.

Many embodiments further comprise one or more haptics to engage a wall of a capsular bag of the eye and increase curvature of one or more of the first component or the second component in response to the wall and/or the perimeter at the zonule attachment of the capsular bag contracting in order to increase optical power of the accommodating intraocular lens.

Many embodiments further comprise a fluid, the fluid comprising one or more of a solution, an oil, a silicone, oil, a solution of high molecular weight molecules, or high molecular weight dextran.

Many embodiments further comprise a seam comprising the adhesive, the seam extending circumferentially along at least a portion of the first component and the second component.

In many embodiments, the first component comprises a first disc shaped structure and the second component comprises a second disc shaped structure. An annular structure can extend between the first disc shaped structure and the second disc shaped structure to separate the first disc shaped structure from the second disc shaped structure and define the inner fluid chamber.

In many embodiments, the intraocular lens comprises a stiff configuration prior to implantation and a soft configuration when implanted.

In many embodiments, the first component comprises a first disc shaped optical structure comprising one or more of a lens, a meniscus, a meniscus lens, or a flat plate, and wherein the second component comprises a second disc shaped optical structure comprising one or more of a lens, a meniscus, a meniscus lens, or a flat plate.

Yet another aspect of the disclosure provides AIOLs for implantation within a lens capsule of a patient's eye. The AIOLs may comprise an optical structure and a haptic structure. The optical structure may have a peripheral portion and may comprise a posterior member, an anterior member coupled to the posterior member at the peripheral portion, and a fluid optical element defined between the posterior and anterior members. The fluid optical element may comprise a fluid having a refractive index similar to either or both the materials comprising the posterior member and the anterior member. The fluid optical element may have an optical power. The haptic structure may couple the posterior and anterior members at the peripheral portion of the optical structure. The haptic structure may comprise a fluid reservoir in fluid communication with the fluid optical element and a peripheral structure for interfacing to the lens capsule. Shape changes of the lens capsule may change the volume or shape of the fluid optical element in correspondence to deformations in one or more of the posterior or anterior members to modify the optical power of the fluid optical element. One or more of the posterior member or the anterior member of the optical structure may be permeable to water such that water present in the lens capsule of the patient's eye may be capable of transferring into or out of the fluid lens chamber there through to achieve an osmotic equilibrium with fluid present in the lens capsule when the AIOL is placed therein. The various features of the AIOLs may further be configured in many ways in accordance with the many embodiments disclosed herein.

In another aspect of the disclosure, an AIOL may comprise an optical structure having a fluid chamber and a material within the fluid chamber. The material may comprise a less than fully hydrated state. A portion of the optical structure may be configured to provide water to the fluid chamber and inhibit leakage of the material from the fluid chamber in order to fully hydrate the material and expand the fluid chamber when placed in the eye.

In yet another aspect of the disclosure, a method of implanting AIOLs within a lens capsule of a patient's eye is provided. The method may comprise advancing an AIOL comprising a less than fully hydrated configuration through an incision of the eye. Water from the lens capsule may pass through at least a portion of the optical structure to fully hydrate the AIOL. In many embodiments, material within a fluid chamber of an optical structure of intraocular lens may be inhibited from leakage from at least a portion of the optical structure while water from the lens capsule passes through to fully hydrate the material.

In several embodiments, the outer fluid reservoir and the inner fluid chamber are filled with a hydrophobic oil which inhibits or fully precludes the transfer of water into the inner fluid chamber. For example, the hydrophobic oils can be selected from any of the following: HYDROCARBON (HYDROBRITE 550), POLYDIMETHYLSILOXANE, POLYOCTYLMETHYLSILOXANE' POLY(2-PHENYL-PROPYL)METHYLSILOXANE, PHENYLMETHYLSILOXANE OLIGOMER, PHENYLMETHYLSILOXANE-DIMETHYLSILOXANE COPOLYMER, DIPHENYLSILOXANE-DIMETHYLSILOXANE COPOLYMERS, PHENYLMETHYLSILOXANE-DIMETHYLSILOXANE COPOLYMERS, 1,1,3,5,5-PENTAPHENYL-1,3,5. This fluid is applicable to any AIOL described herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Features of the present technology are set forth with particularity in the appended claims. A better understanding of the features and advantages of the present technology will be obtained by reference to the following detailed description that sets forth illustrative embodiments, in which the principles of the invention are utilized, and the accompanying drawings of which:

FIGS. 6A-6C illustrate AIOL 600 comprising three main parts, in accordance with embodiments; and FIGS. 7A-7B illustrate AIOL 700 comprising three main parts, in accordance with embodiments.

FIG. 8 depicts an AIOL lens system comprising multiple square-shaped annular regions.

FIGS. 13A-13J embody two different flow features, one defined by outer flow-throughs and the other defined by inner flow-throughs.

FIGS. 14A-14E present an alternate design for a fixed lens assembly.

FIGS. 15A-15D present an alternate design for a fixed lens assembly.

FIGS. 17A-17G illustrate three outer flow-throughs to provide enhanced access for a suction tool to remove OVD from the posterior space between the capsule and the posterior surfaces of the AIOL.

FIGS. 18A-18D illustrate accommodating intraocular lens 1800 incorporating features to enhance performance.

DETAILED DESCRIPTION

Figure 1:
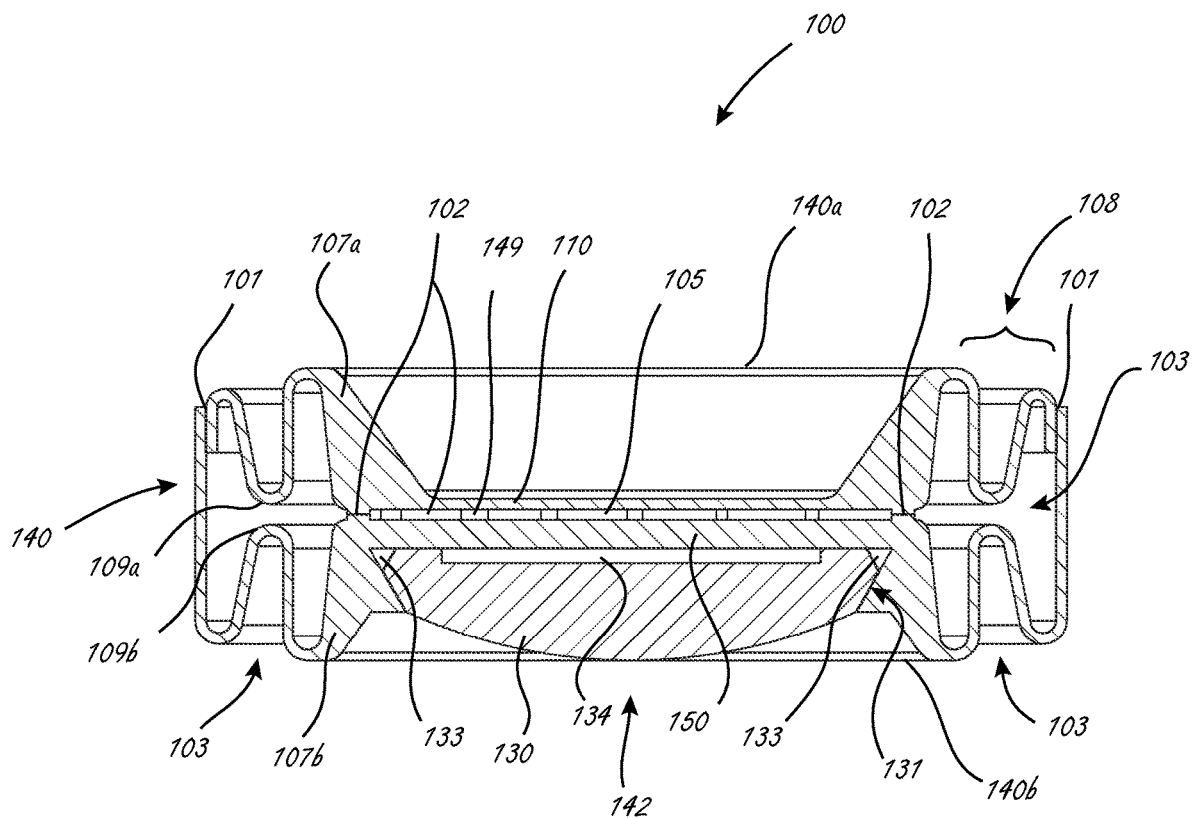
FIG. 1 shows a cross-sectional view of a fluid filled accommodating lens system comprising a bellows structure in accordance with embodiments.

Accommodating intraocular lenses (AIOLs) as described herein can be used to provide improved vision, and can be combined with one or more of many known surgical procedures and apparatus, such as cataract surgery and intraocular lens inserters. The optical structures of the AIOLs are well suited for use with commercially available IOL power calculations based on biometry of the eye, and can be used to provide improved vision. In many embodiments, a physician can insert an AIOL as described herein in a manner similar to prior non-accommodating IOLs such that the AIOLs as described herein can be readily used.

The present disclosure relates to devices, methods, and systems associated with AIOLs. Some embodiments will comprise a central optical structure comprised of at least one deformable optical component (e.g., an optical element) spaced apart along an optical axis, such as by a support structure concentric with the optical axis of the lenses. Several embodiments include a first optical component and a second optical component, and at least one of the first and second optical components can be deformable while the other of the first and second optical components can be deformable or rigid. The volume bounded by the first and second optical components, and optionally the lens support structure, may define a fluid chamber that can be filled with an ionic solution, such as saline, or non-ionic solutions such as dextran or silicone oil. The first and second optical components may instead be bounded by one or more haptic structures, and the haptic structures may define an outer fluid reservoir filled with a fluid and arranged in a plane normal to the optical axis of the first and second optical components. The fluid in the outer fluid reservoir of the haptic structures can be in fluid communication with the fluid in the inner fluid chamber bounded by the optical structure. The transfer of fluid between the haptic structures and the inner fluid chamber of the optical structure can change the accommodating power of the fluid within the inner fluid chamber by deforming one or both of the first and second optical components. The improved AIOL system may additionally comprise any combination of the features described herein.

The optical components and some of the support structures described herein will typically be fabricated from a hydrophilic material that is optically clear when hydrated, swells on hydration by more than 10%, and accommodates strain levels of greater than 100% when hydrated. The material can be purchased as small disks and rods. For example, the hydrophilic material may comprise a copolymer of hydroxyethyl methacrylate (HEMA) and methyl methacrylate (MMA) such as CI18, CI21, or CI26 produced by Contamac Ltd. of the UK. The material may alternately be comprised of a co-polymer of HEMA and EOEMA such as a poly(2-ethyloxyethyl methacrylate, which can be purchased as a BENZ IOL 25 or a BENZ IOL 25 UVX from Benz Research & Development, 6447 Parkland Dr., Sarasota, FL 34243 United States. These materials are also denoted as PMMA herein, and as used herein PMMA refers to a polymer comprising PMMA or a copolymer comprising PMMA, such as one or more of PMMA polymer (also referred to herein as "poly(methyl methacrylate)"), or a copolymer of HEMA and PMMA such as p(HEMA-co-MMA), for example. As used herein p(HEMA-co-MMA) refers to a copolymer of HEMA and PMMA and can also be referred to as p(HEMA-MMA The copolymer may comprise one or more of a block copolymer (PPPP-HHHH), alternating copolymer (PHPHPHPH), statistical or random copolymer (PHPPHPHH), a star copolymer, a brush copolymer, or a graft copolymer, for example, where "P" identifies "MMA" and "H" identifies "HEMA", for example.

In some embodiments, components of a hydrogel AIOL may be fabricated by 3D printing, including but not limited to any of the following common 3D printing processes: Stereolithography (SLA), Inkjet material jetting (IMJ), Digital Light Processing (DLP), Selective Laser Sintering (SLS), Fused Deposition Modeling, or Fused Filament Fabrication (FDM/FFF). Methods such as SLA, IMJ, and DLP may be particularly suited to the fabrication of AIOL elements comprised of hydrogels such as PMMAs and copolymers such as HEMA. In such embodiments, the starting material may be monomer or oligomer precursors, or combinations thereof, of the hydrogel polymer. One such polymer useful in the fabrication of AIOLs herein described may comprise pHEMA, in which the polymerization reaction can be photo initiated by a UV source of appropriate wavelength and duration. In some such embodiments, photo initiation may be further enhanced by the addition of a photoinitiator compound mixed with the monomers used for printing. Such photoinitiators can release additional free radicals on illumination thereby increasing the rate of the polymerization reactions. A selection of photoinitiators is listed below.

In some embodiments, a complete AIOL may be fabricated by a 3D printing process and the un-polymerized materials on the inside of the optical structure can be removed after completion of the build. Alternatively, or in combination, the un-polymerized materials within the optical structure may be treated such that reactive end groups are rendered nonreactive to prevent further polymerization. In other embodiments, the AIOL structures may be fabricated as subcomponents for later assembly as described elsewhere herein for machined parts.

As used herein, a positive curvature of an outer surface encompasses a convex curvature and a negative curvature of an outer surface encompasses a concave curvature.

As used herein, like reference numerals refer to like structures. In many embodiments as described herein, the reference numerals comprise three or four digits in which the first one or two digits refer to the number of the drawing and the last two digits refer to like structures among figures having different numbers. For example, the reference numerals 105 and 1205 refer to similar deflectable members of FIG. 1 and FIG. 12, respectively. A person of ordinary skill in the art will recognize that text describing a structure of one figure may apply to a similar structure of any other figure as provided herein.

In some embodiments, the intraocular lens, lens system and/or other components defining the fluid chamber of the optical structure are filled with a water-based clear fluid with a refractive index higher than water to increase the optical power of the system. The high refractive index of such fluids may be caused by the presence of solutes, such as large molecules incapable of crossing the chamber defining components. Examples of suitable large molecules include dextran, with exemplary molecular weights of <40 kD, <70 kD, <500 kD, and <1000 kD. Further examples of suitable solutes include sugar molecules. The solutes and water may compose a diluted solution having an osmolality that, for example, causes water to move into or out of the chamber to achieve an osmotic equilibrium volume. The osmotic equilibrium volume can be adequate to produce the appropriate optical power in the system to the desired power for the patient.

The soft material of the optical structures of the AIOL can be shaped in one or more of many ways, and may comprise machined components, molded components, or combinations thereof, for example.

AIOLs in accordance with the present technology can have a reduced delivery cross-section. The reduced delivery cross-section can be facilitated by an optical structure capable of translating from a delivery configuration to an operational configuration. The optical structure may have a small dimension along the optical axis in the delivery configuration and larger dimension along the optical axis in operational configuration. Also, a lens support structure can be configured to maintain the distance between the peripheries of the two optical components in the operational configuration and to allow fluid to pass between the haptic structures and the fluid volume bounded by the optical structure in either configuration.

The delivery cross-section may be attained by folding or rolling an AIOL around a delivery axis normal to the optical axis. The delivery cross-section may be measured as the largest dimension in the delivery configuration measured in a plane normal to the delivery axis. Delivery cross-sections attainable for several embodiments of the AIOLs disclosed herein may be less than 4.5 mm, and preferably less than 2.5 mm. In alternate embodiments, the delivery cross-section can be attained by forcing the AIOL through a tube or delivery aperture. Such a tube may be conical in cross-section such that the AIOL may be compressed as it progresses down the tube. The distal end may be sized to interface with an incision in the eye. Delivery may be facilitated by syringes or plungers.

The intraocular lens system may be comprised of at least two PMMA optical components where PMMA denotes a compound comprising one or more of poly(methyl methacrylate) (PMMA), poly(hydroxyethyl methacrylate) (PHEMA), (Hydroxyethyl)methacrylate (HEMA), or Methyl methacrylate (MMA), for example. The lens system may include other elements comprised of any or any combination of the following materials: NiTi, polyurethane, hydrophilic PMMA, photo-activated polymers, precursors to PMMA, Ethylene glycol dimethacrylate (EGDMA), silicones, silicone copolymers, among others.

One or more of the optical components, such as a substantially planar member or a plano-convex member, may comprise a polymeric material. The polymeric material may comprise a material, for example available from Contamac Ltd. of the UK or Vista Optics Ltd. of the UK. For example, the PMMA copolymer may be selected from the list comprising a Definitive 50 material, a Definitive 65 material, a Definitive 74 material, a Filcon V3 material, a Filcon V4 material, a Filcon V5 material, an Optimum Classic material, an Optimum Comfort material, an Optimum Extra material, an Optimum Extra 16 material, an Optimum Extra 18.25 mm material, an Optimum Extra 19 mm material, an Optimum Extra 21 mm material, an Optimum Extreme material, an F2 material, an F2 Low material, an F2 Mid material, an F2 High material, a Focon III 2 material, a Focon III 3 material, a Focon III 4 material, a Hybrid FS material, a Contaflex GM Advance material, a Contaflex GM Advance 49% material, a Contaflex GM Advance 58% material, a Filcon I 2 material, a Filcon II 2 material, a Contaflex GM3 49% material, a Contaflex GM3 58% material, a Contaflex material, a Contaflex 58% material, a Contaflex 67% material, a Contaflex 75% material, a Polymacon 38% material, a Hefilcon 45% material, a Methafilcon 55% material, a Filcon II material, a Filcon IV 2 material, an HI56 material, a PMMA material, a CI26 material, a CI26Y material, a CI18 material, and other variants available from Contamac Ltd. of the UK and a Vistaflex GL 59 material, a HEMA/GMA material, an Advantage+ 49 material, an Advantage+ 59 material, a Filcon I 1 material, a Filcon 12 material, a VSO nVP material, a nVP/MMA material, a VSO 60 material, a VSO 68 material, a VSO 75 material, a Filcon II 1 material, a Filcon II 2 material, a VSO pHEMA material, a pHEMA material, a HEMA material, a VSO 38 material, a VSO 42 material, a VSO 50 material, a Vistaflex 67 Clear UV material, a polysiloxy-acrylate material, an AddVALUE Silicone Acrylate material, an AddVALUE 18 material, an AddVALUE 35 material, a poly-fluoro-silicon-acrylate material, an AddVALUE Fluor Silicone Acrylate material, an AddVALUE 25 material, an AddVALUE 50 material, an AddVALUE 75 material, an AddVALUE 100 material, a Scleral Rigid Gas Permeable material, a hydrophobic intraocular lens material, a VOPhobic Clear Tg 16 material, a VOPhobic Yellow Tg 16 material, a hydrophilic intraocular lens material, a HEMA-MMA copolymer material, an IOSoft material, an IOSoft clear material, an IOSoft yellow material, a PMMA material, a Vistacryl CQ UV material, a Vistacryl XL blue material, a Vistacryl CQ material, and other variants available from Vista Optics Ltd. of the UK. Often, the polymeric material may be water permeable and/or hydrophilic. Water present in the lens capsule of the patient's eye may transfer into or out of the fluid optical element through the polymeric material to achieve an osmotic equilibrium with fluid present in the lens capsule when the intraocular lens is placed therein. The polymeric material may be non-permeable to silicone oil. The polymeric material may be non-permeable to compounds having molecular weights of greater than 40 kDa.

In some embodiments, an AIOL in accordance with the present technology is inserted into and interfaced with the natural capsule such that the interface zones create a seal which forms a semi toroidal region of capsule. In operation, fluid transfer between the semi toroidal region and the interior of the AIOL causes an accommodation change in the AIOL. In such embodiments, fluid such as saline may be injected into the semi toroidal region.

In some embodiments, the lens support structure and one optical component of an accommodating optical structure are machined or molded as a single structure and a fixed-power lens is affixed to the support structure by a bonding means. In many other embodiments, the accommodating optical structure and a fluid-based haptic structure of an AIOL are comprised of two halves that each incorporate an optical component of the accommodating optical structure and a portion of the haptic structure. The two halves are bonded together to form the optical structure and the haptic structure. In yet other embodiments, a second machining operation can be performed on the bonded structure. Alternate bonding means may include mechanical interfaces such as threading where the outer periphery of the lens is threaded and the inner surface of the support structure is threaded. In alternate embodiments, the interface can be a simple interference fit. In some embodiments, affixing comprises bonding the materials by treating the one or both of the separate bonding surfaces with a precursor monomer(s), short chain multimer(s) or partially prepolymerized base polymer(s), then assembling the structure, applying a load across the bonding surfaces, and heating the assembly for a period of time. Such a process may facilitate cross-linking between the material comprising both parts. In some instances, the precursor monomer may be mixed with small particles of the polymer. Other bonding agents may additionally include urethanes, silicones, epoxies, and acrylics among others.

In the devices of the present disclosure, the lenses may be compromised of a water and ion permeable material. In some embodiments, the AIOL can be allowed to self-fill after implantation, thereby minimizing the delivery cross-section.

In alternate embodiments, the AIOL is filled after implantation.

Embodiments of the Present Technology

FIG. 1 illustrates a cross section of a radially symmetric AIOL 100 comprising a fixed lens 130 and an accommodating structure 140. The embodiment of the accommodating structure 140 shown in FIG. 1 comprises a first component 140a and a second component 140b that together define an inner optical structure 142 and an outer fluid reservoir 103.

100 AIOL
101 joint
102 posts
103 outer fluid reservoir
105 fluid chamber
107a first annular stiff region
107b second annular stiff region
108 bellows
109a first fold
109b second fold
110 first optical component
130 fixed lens
131 interfacing feature
133 relief spaces
134 relief
140 accommodation structure
140a first component
140b second component
142 inner optical structure
150 second optical component Several embodiments of the AIOL 100 may have a base power associated with the power of the fixed lens 130 but no base power associated with the accommodating structure 140 when the accommodating structure 140 is in a relaxed condition (i.e., when no pressure is applied to the outer fluid reservoir 103). The first component 140a and the second component 140b may be affixed to one another at a seam or joint 101 using, for example, a bonding agent as described elsewhere herein. The first and second components 140a-b may optionally be affixed at the interface between protrusions 102 (also referred to herein as posts).

The protrusions 102 may be located on the inner surface of one or more of the first component 140a and the second component 140b. The protrusions 102 may for example separate the first and second components 140a, 140b as described elsewhere herein. The joint 101 may extend circumferentially around the outer perimeter of the first component 140a and the second component 140b.

The outer fluid reservoir 103 may have a bellows 108, and the inner optical structure 142 has an inner fluid chamber 105 in fluid communications with the outer fluid reservoir 103. The bellows 108 may be formed from an outer region of the first component 140a and an outer region of the second component 140b. The bellows 108 may comprise one or more compliant folds 109 (identified individually as 109a and 109b) extending continuously circumferentially around an optical axis of one or more of the first and second components 140a, 140b. The one or more folds 109a, 109b of the first and second components 140a, 140b, respectively, may for example extend towards each other to define an inner bellows region and an outer bellows region. As a result, the outer fluid reservoir 103 can have one or more folds 109a-b that defines a fold region, which in turn separates an inner bellows region from an outer bellows region. The bellows 108 may comprise a plurality of folds or pleats.

The inner fluid chamber 105 may be defined between an inner surface of an inner region of the first component 140a and an inner surface of an inner region of the second component 140b. More specifically, the first component 140a may have a first optical component 110 at its inner region, and the second component 140b may have a second optical component 150 at its inner region. The fluid chamber 105 shown in FIG. 1 can be defined, at least in part, by the first and second optical components 110 and 150. The bellows 108 may extend continuously circumferentially around the first and second optical components 110 and 150.

The protrusions 102 are disposed radially outward from the first and second optical components 110 and 150 (e.g., between the inner and the outer regions of the first and second components 140a, 140b). The spaces between the protrusions 102 can be fluid channels 149 or conduits between the outer fluid reservoir 103 and the inner fluid chamber 105. The outer fluid reservoir 103 and the inner fluid chamber 105 are accordingly in fluid communication with each other to provide optical power changes in response to shape changes of the lens capsule as previously described herein.

The first optical component 110 and/or the second optical component 150 may comprise a planar member. The first optical component 110 and/or the second optical component 150 may be membranes that have no optical power in an unbiased state and/or a biased state. The first optical component 110 may comprise a deflectable planar member configured to deflect in response to fluid transfer between the inner fluid chamber 105 and the outer fluid reservoir 103. For example, when the bellows 108 are compressed and fluid is forced into the inner fluid chamber 105, the first optical component 110 of the first component 140a may deflect along the optical path to impart an optical power to the inner optical structure 142. Deflection of the first optical component 110 may comprise changes in one or more of a dimension and shape of the inner fluid chamber 105 such as a change in the distance separating inner surfaces of the first and second optical components 110 and 150. The optical power of the inner optical structure 142 (shown in FIG. 10B as region YY) may, for example, be a factor of the optical power change of the AIOL 100. The second optical component 150 may be a planar member with a larger cross-section (i.e., thickness) than the first optical component 110, and thus the second optical component 150 may deform less than first optical component 110. Any such deformation of second optical component 150 may be accommodated by a relief 134 in the fixed lens 130. The relief 135, for example, can be defined by a recess in the fixed lens 130 such that the solid surfaces in the optical field do not touch even during accommodation.

One or more of the inner regions of the first and second components 140a and 140b may comprise a shell, such as a non-planar shell (not shown). The first component 140a may comprise an anterior component, and the second component 140b may comprise a posterior component. Though shown in the current embodiment as planar members, one or both of the optical components 110 and 150 may comprise a plano-convex member or another standard optical configuration that provides optical power. In any of the foregoing examples, at least one of the optical components is configured to deform as optical fluid is transferred into the optical portion of the fluid chamber 105. The first component 140a and the second component 140b may additionally comprise annularly-shaped stiff coupling regions 107a and 107b, respectively, to inhibit radial movement of the first and second optical components 110 and 150. The coupling regions 107a-b in combination with the fixation between the first and second components 104a-b at the protrusions 102 effectively isolate the first and second optical components 110 and 150 from being distorted (e.g., deformed) asymmetrically with respect to the optical axis of the accommodating structure 140.

The second component 140b may further comprise an interfacing feature 131 which can secure the fixed lens 130 to the second component 140b as illustrated. The fixed lens 130 may be configured to snap-fit onto the first or second component 140a, 140b. The fixed lens 130 may be snap-fit onto or otherwise coupled to the first or second component 140a, 140b in situ within an eye of a patient, such as within a lens capsule of the eye, for example. The fixed lens 130 may for example have an inner surface facing and adjacent to an outer surface of the first or second component 140a, 140b to which the fixed lens 130 is coupled. The fixed lens 130 may also have a peripheral relief 133. The interfacing feature 131 and the fixed lens 130 may be additionally configured such that interfacing channels exist between the fixed lens 130 and the second component 140b to allow body fluids to freely flow into any out of relief spaces 134 and 133. The fixed lens 130 may for example comprise a third component of the AIOL 100. The fixed lens 130 may have an optical power.

One or more of the first and second components 140a, 140b may comprise a polymeric material as previously described herein. The first and second components 140a, 140b may be sufficiently flexible to be folded into a reduced cross-section delivery configuration for delivery to the eye as previously described herein. The first and second components 140a, 140b may be bonded to each other as previously described herein. The first and second components 140a, 140b may be fabricated as previously described herein. The third component or fixed lens 130 may be sufficiently flexible to be folded into a reduced cross-section delivery configuration for delivery to the eye as well, and as described above the fixed lens 130 may be fixedly coupled to the first or second components 140a, 140b in situ.

The AIOL 100 may be filled with a fluid such as any of the fluids previously described herein. The fluid in the inner fluid chamber 105 may provide optical power to the accommodating structure 140.

The bellows 108 may comprise a continuous baffle structure disposed about a periphery of the inner fluid chamber 105. The continuous structure of the bellows 108 may be an annular, elliptical, and rotationally symmetric shape as previously elsewhere herein.

Figure 2:
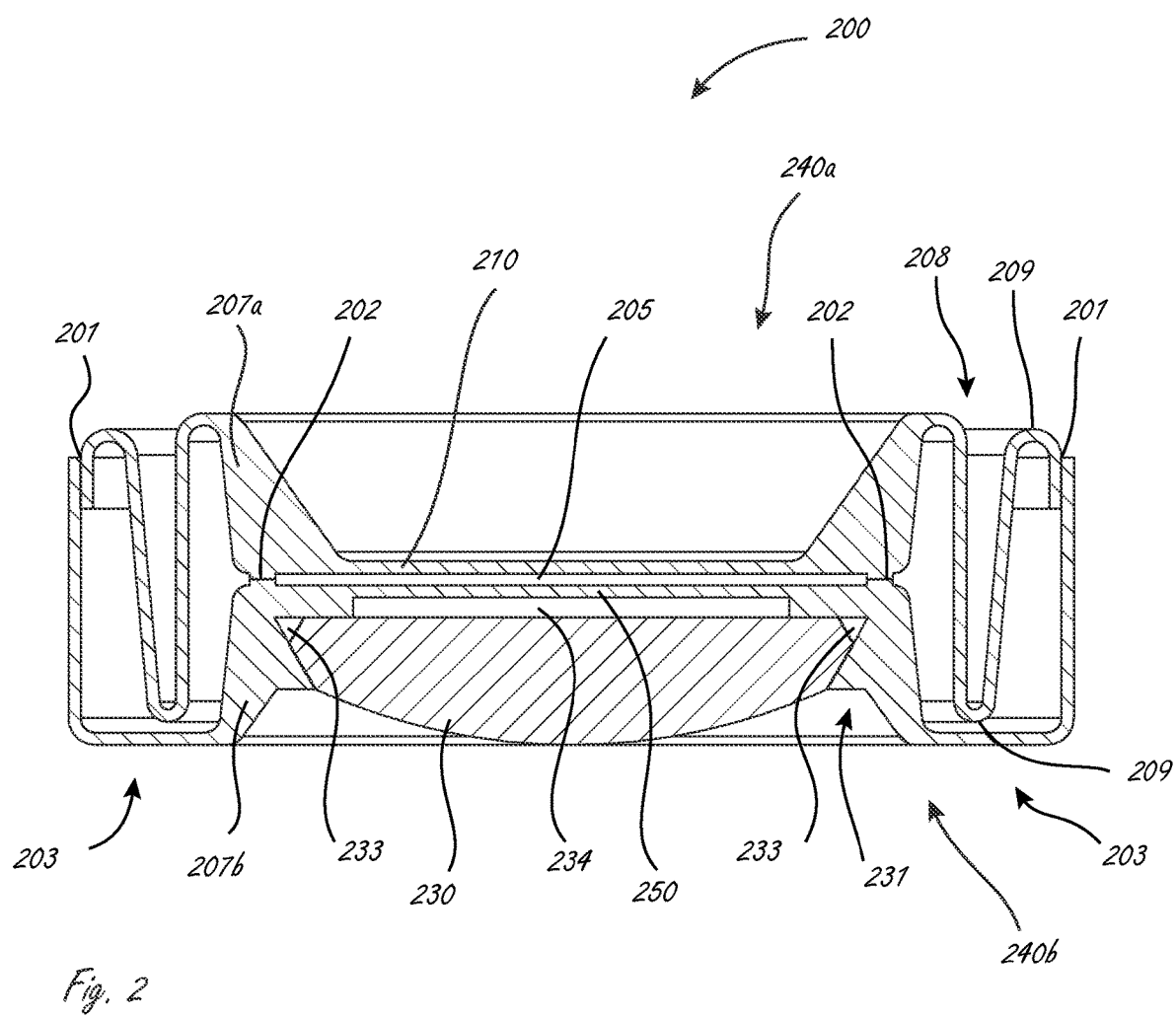
FIG. 2 shows a cross-sectional view of an alternate accommodating lens system in accordance with embodiments.

The dimensions and geometry of the accommodating lens systems described herein may be varied. For example, FIG. 2 illustrates an alternate AIOL 200.

200 AIOL
240a first component
240b second component
201 joint
202 posts
203 outer fluid reservoir
205 fluid chamber
207a first annular stiff region
207b second annular stiff region
208 bellows
210 first optical component
230 fixed lens
231 interfacing feature
233 relief space, lens attachment feature
234 relief space, deformation chamber
250 second optical component The AIOL 200 comprises structures similar to AIOL 100, and the last two digits of the reference numerals identify similar structures. The AIOL 200 can have a second component 240b with a second optical component 250 that is thinner than the second optical component 150. The second optical component 250 may therefore deform in a fashion which increases the accommodative optical power of the AIOL 200 compared to the AIOL 100. The additional deformation of the thin second optical component 250 may occur within a deformation relief 234 in the second optical component 250 instead of the fixed lens 130 in the AIOL 100. In another embodiment (not shown), the AIOL 200 can have the deformation relief 234 in the second optical component 150 and the deformation relief 134 of the fixed lens 130 of the AIOL 100 in the same device. The AIOL 200 can also include an outer fluid reservoir 203 comprising two folds in only the first component 140a of the AIOL 200. For example, the outer region of the first component 240a may define a bellows 208 having two folds 209, while the outer region of the second component 240b has none (e.g., a flat portion).

Figure 3:
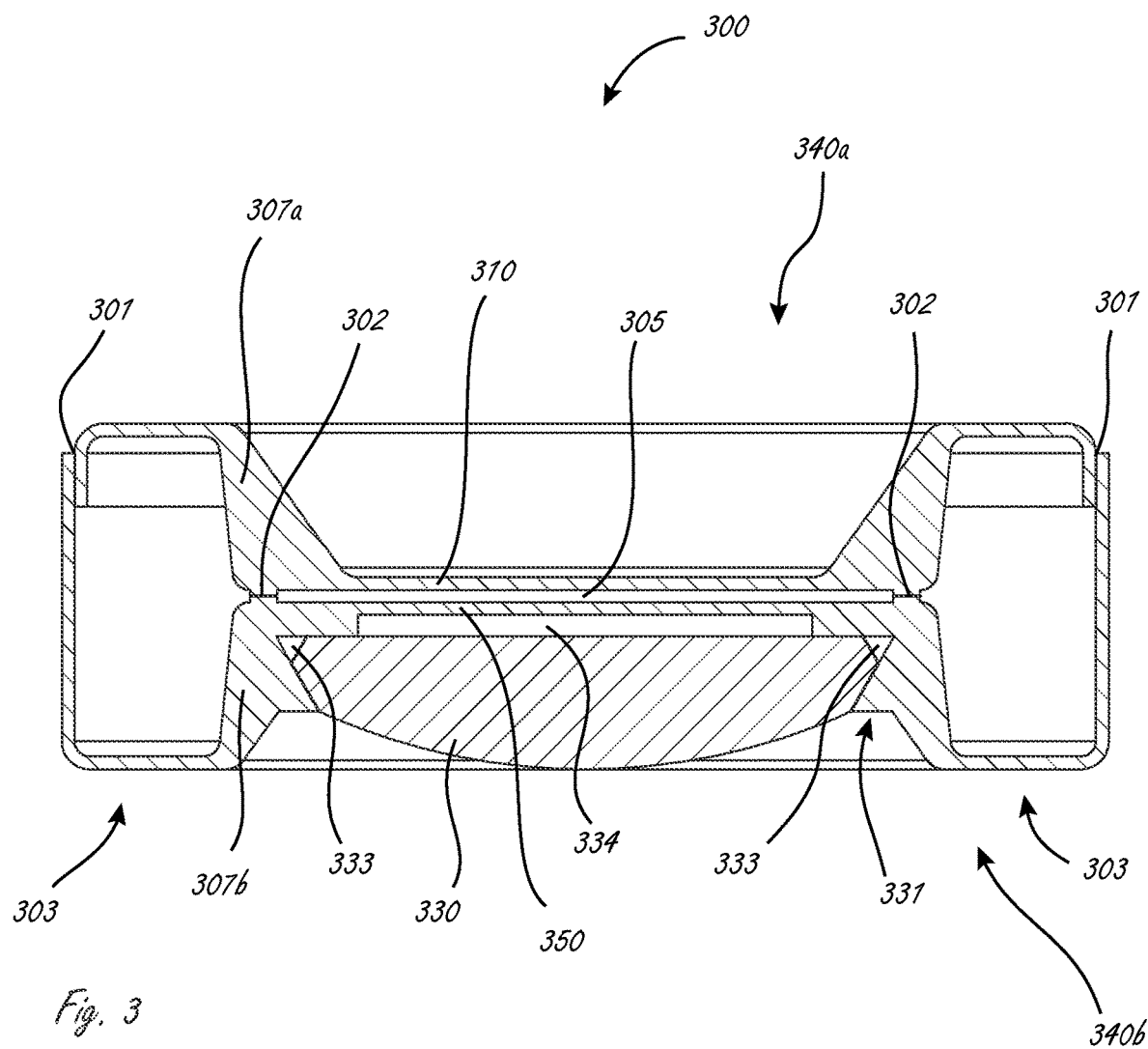
FIG. 3 shows a cross-sectional view of an alternate fluid filled accommodating lens system in accordance with embodiments.

In other examples, the geometry of the fluid chamber or the bellows or other fluid reservoir structure may be varied. For example, FIG. 3 illustrates an AIOL 300, which is similar in structure to the AIOL 200, in which the last two digits of the reference numerals identify similar structures. The AIOL 300 comprises an outer fluid reservoir 303 that extends continuous and circumferentially around an inner fluid chamber 305 and stiff annular regions 307a-b. The outer fluid reservoir 303 has a rectilinear cross-sectional shape. The AIOL 300 accordingly has a fold-less bellows 308 that drives fluid into or receives fluid from the inner fluid chamber 305.

- 300 AIOL
- 340a first component
- 340b second component
- 301 joint
- 302 posts
- 303 outer fluid reservoir
- 305 fluid chamber
- 307a annular stiff region—a
- 307b annular stiff region—b
- 308 bellows
- 310 first optical component
- 330 fixed lens
- 331 interfacing feature
- 333 relief space, lens attachment feature
- 334 relief space, deformation chamber
- 350 second optical component The various peripheral fluid-filled bellows 108, 208, 308 of AIOLs 100, 200, and 300, respectively, provide control of the stiffness of the outer fluid reservoir. This allows the AIOLs to provide the desired accommodation based on the forces applied by the eye on the structure and the resulting accommodation.

Figure 4A:
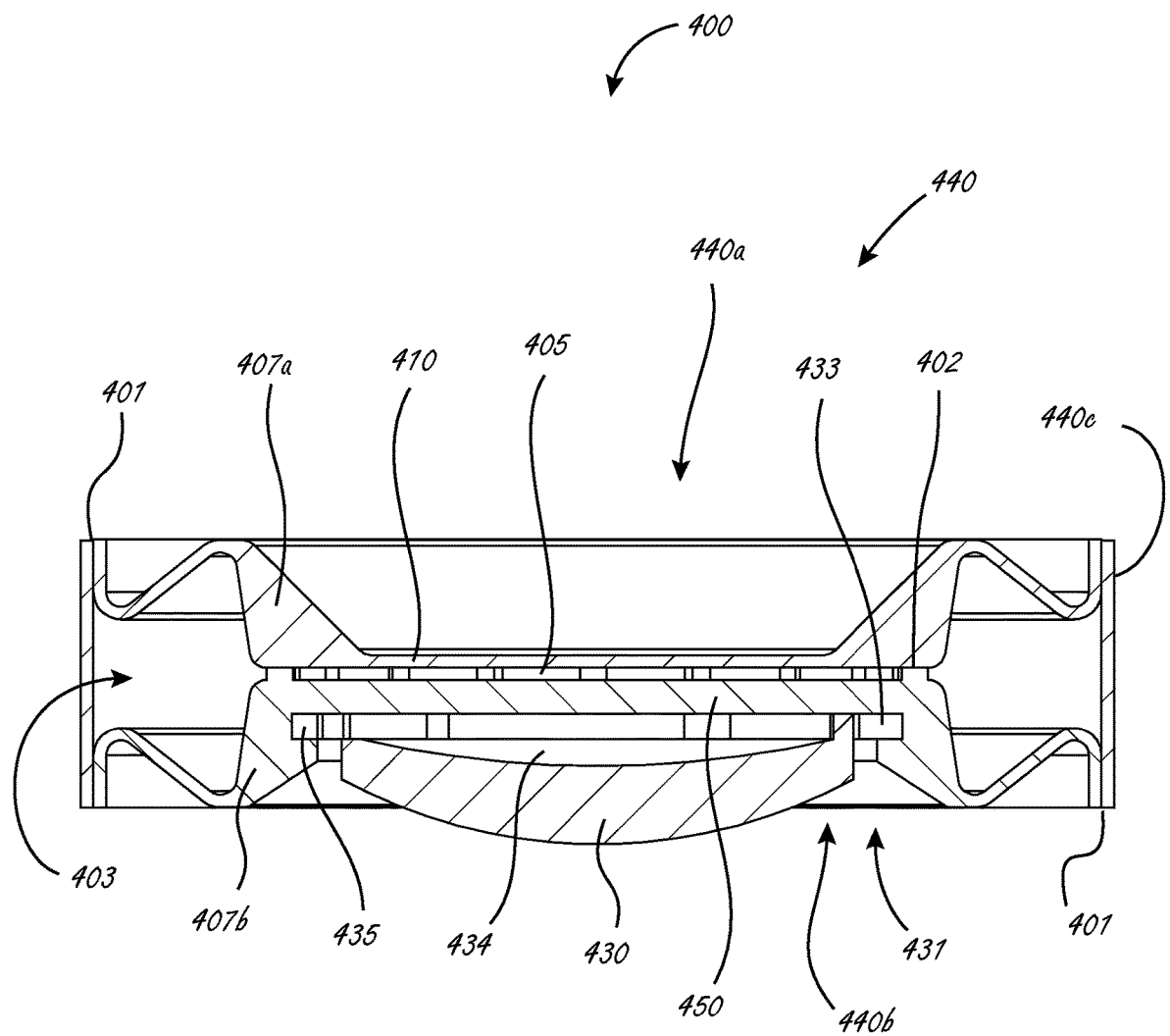
FIGS. 4A-4C illustrate AIOL assembly 400 comprising four main parts, in accordance with embodiments.
Figures 4B, 4C:
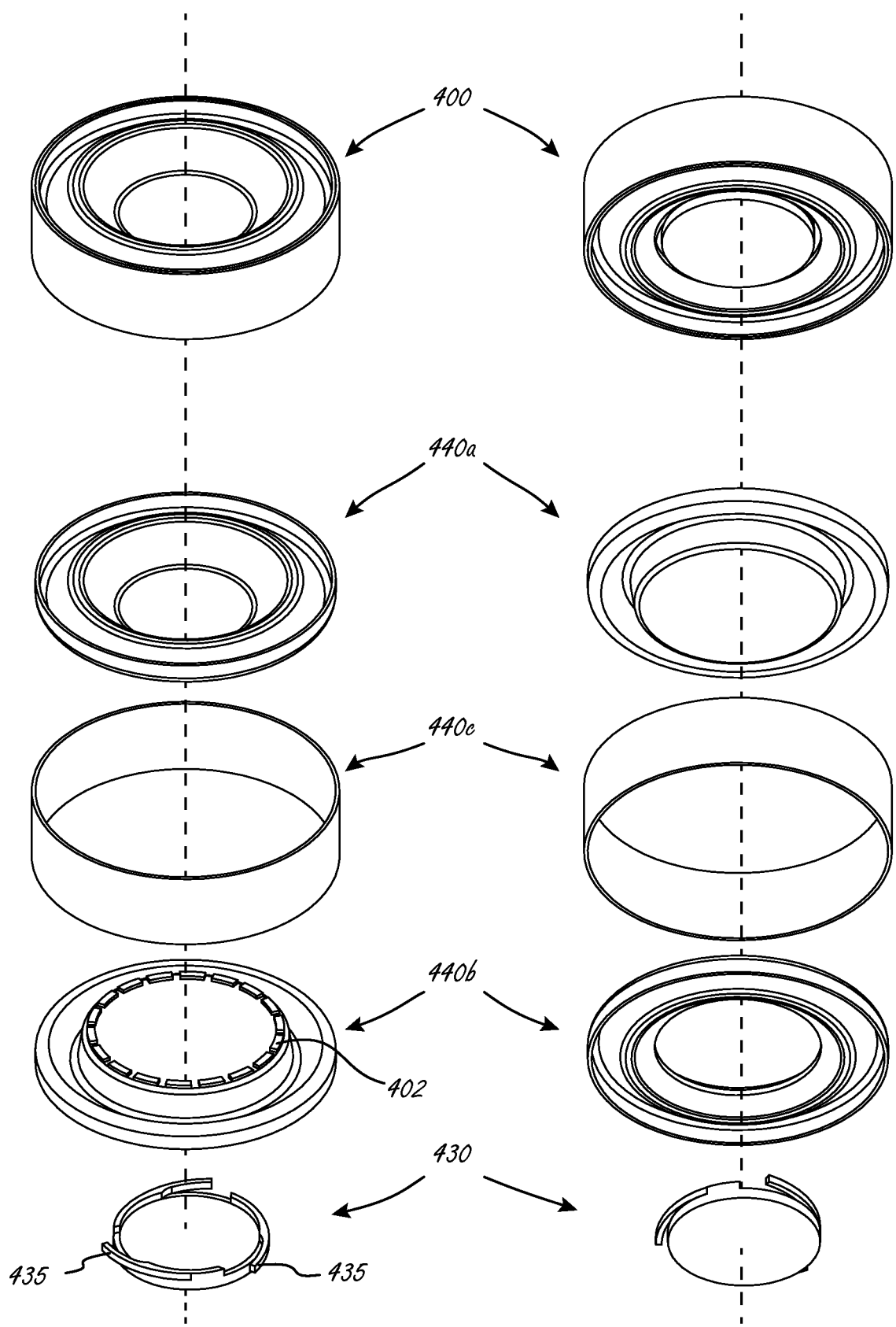

FIGS. 4A, 4B, and 4C illustrate an AIOL 400 similar to embodiments of the AIOLs 100, 200, and 300 above, in which the last two digits of the reference numerals identify similar structures.

- 400 AIOL
- 440a first component
- 440b second component element
- 440c outer ring element
- 401 joint
- 402 posts
- 403 outer fluid reservoir
- 405 fluid chamber
- 407a annular stiff region
- 407b annular stiff region
- 408 bellows
- 410 first optical component
- 430 fixed lens
- 431 interfacing feature
- 433 relief space
- 434 relief space
- 435 latching mechanism
- 450 second optical The AIOL 400 may have four primary parts including: a first component 440a; a second component 440b; a fixed lens 430 defining a third component; and an outer ring element 440c defining a fourth element (e.g., a thin-walled ring). The outer ring element 440c may be affixed to the first component 440a and the second component 440b at seams or joints 401 to couple the first and second components 440a, 440b to one another at their peripheries. The outer ring element 440c, the first component 440a, and the second component 440b may together define the outer fluid reservoir 403, which is in fluid communication with a fluid chamber 405 of an accommodating structure 440. The outer ring element 440c may be fabricated of a material with different material properties than the rest of the components of the structure. In some embodiments, the outer ring element 440c may be fabricated with a version of the polymer used to fabricate the first component 440a and second component 440b with a reduced modulus of elasticity. The outer ring element 440c may therefore be more easily fabricated and it may have a thinner cross-section than might otherwise be possible. Alternatively, or in combination, the outer ring element 440c can be spin cast or centripetally cast, thus allowing for structures even thinner than might be obtainable by machining.

The AIOL 400 may have a fixed lens 430 comprising a convex concave configuration. The fixed lens 430 may be attached to the second component 440b by a latching mechanism 435 that interlocks with an interface feature 431. The AIOL 400 may have a relief 434 created by offsetting the latching mechanism 435 and the convex surface of the fixed lens 430.

Figure 5:
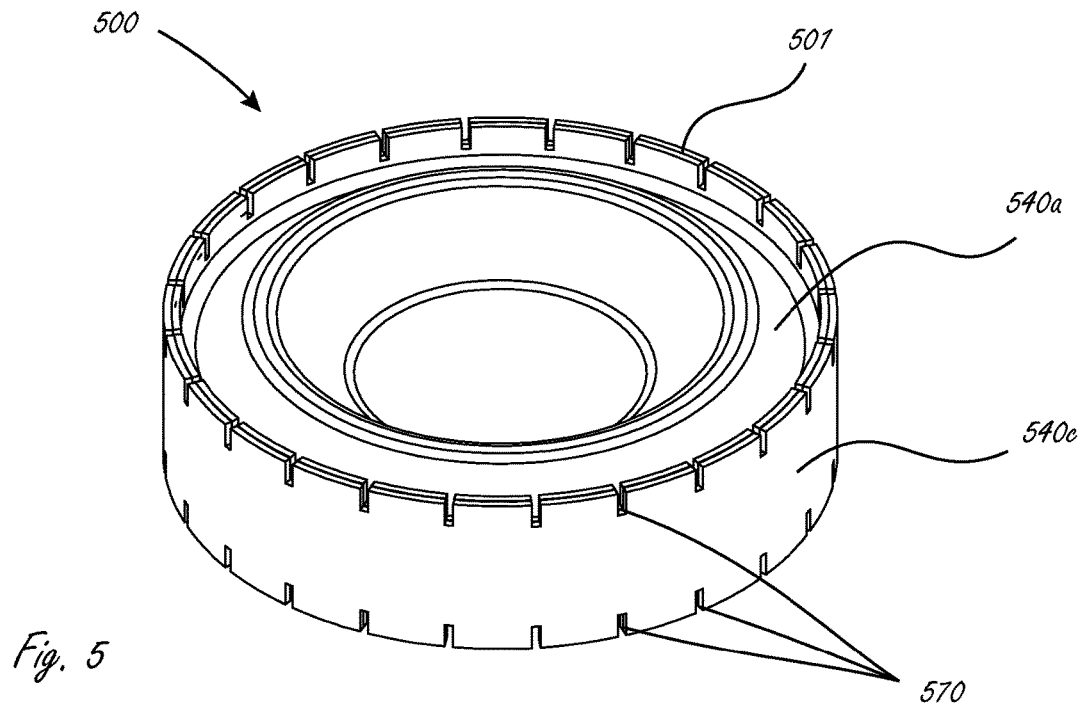
FIG. 5 is a completed AIOL assembly 500, an alternate embodiment to AIOL 400.

FIG. 5 illustrates an AIOL 500 which is a variation of the AIOL 400, and the last two digits of the reference numerals identify similar structures.

- 500 AIOL
- 501 joint
- 540 accommodating structure
- 540a first component
- 540b second component
- 540c outer ring
- 570 slot The AIOL 500 has first interface zones between the first component 540a and the outer ring 540c, and second interface zones between the second component 540b (not visible) and the outer ring 540c. The first and second interface zones may have slots 570 to increase the flexibility of the outer peripheral portion of the AIOL 500. The slots 570 may be fabricated in the structural components comprising AIOL 500 before or after the components have been assembled. Slots 570, when added after the structure has been assembled, may be created by one or more of mechanical cutting, laser cutting, and any other suitable means. The slots 570 may be created such that they extend partially down a seam so that a portion of the seam remains uncut and the seal between components of AIOL remains intact.

Figure 6A:
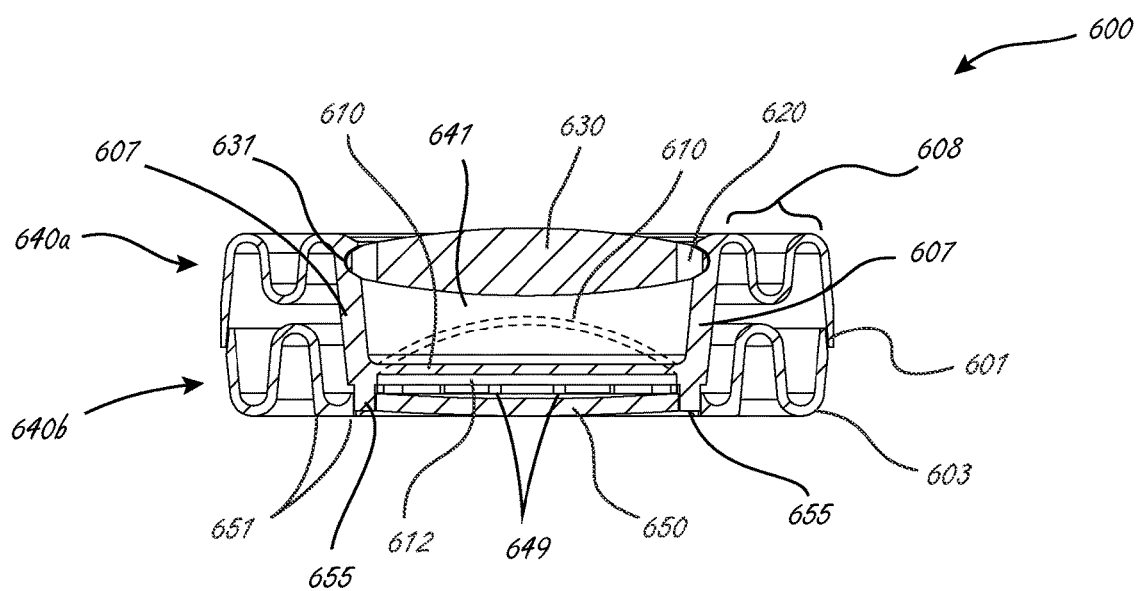

FIGS. 6A, 6B and 6C illustrate aspects of an AIOL 600, which is an additional embodiment of an AIOL similar to embodiments of the AIOLs 100, 200, 300, 400 and 500.

- 600 AIOL
- 640a first component
- 640b second component
- 601 joint
- 603 outer fluid reservoir
- 603a inner continuous bellows
- 603b outer continuous bellows
- 607 annular stiff region
- 608 bellows
- 610 first optical component or planar member
- 612 fluid accommodating Lens
- 620 through hole
- 630 fixed lens
- 631 interfacing feature or fixed lens receiver 640 accommodating structure
641 aqueous chamber
649 fluid channel
650 second optical component or optic membrane
651 square edge
653 side-B AIOL
654 fixed lens receiver
655 bonding pin
656 bonding pin receiver
657 stand off The AIOL 600 comprises three primary structures (FIG. 6B) including (a) a fixed lens 630, (b) a first component 640a, and (c) a second component 640b. The first and second components 640a and 640b are bonded together at a seam 601 to define an outer fluid reservoir 603 as shown in the cross-sectional view FIG. 6A.

The first component 640a has a fixed lens receiver 631 (FIG. 6C) and an aqueous chamber 641. The fixed lens 630 is attached to the first component 640a at a fixed lens receiver 631, and the fixed lens 630 can have at least one through hole 620 that allows aqueous fluid in the lens capsule to flow into and out of the aqueous chamber 641. The first component 640a can be the anterior portion of the AIOL 600, and the lens receiver 631 can be configured to enable the correct fixed lens power for the patient to be identified and provided at the time of the procedure after an accommodating portion 640 (i.e., the first and second components 640a and 640b) has been placed in the native eye capsule. The fixed lens 630 can be selected after the accommodating portion 640 has been implanted in the native eye capsule so that the optical power of the fixed lens 630 compensates for any optical power exhibited by the accommodating structure 640 when in the relaxed capsule. This aspect of AIOL 600, and several other AIOLs described herein, is possible because the first components 640a is the anterior portion of the AIOL 600.

The fixed lens 630 can also be selected to accommodate the refractive requirements of the patient after the accommodating structure 640 has been implanted. For example, the accommodating structure 640 can change the refractive requirements of the patient, and thus selecting the fixed lens 630 after implanting the accommodating structure 640 allows practitioners to meet the refractive requirements of the patients using the fixed lens 630.

Another feature of the AIOL 600 is the manner in which first component 640a is attached to second component 640b (FIG. 6C). The first component 640a comprises bonding pins 655 and the second component 640b comprises bonding pin receivers 656 configured to receive (e.g., mate) with the bonding pins 655. The first component 640a further comprises standoffs 657 (FIG. 6B) which form a fluid chamber 612 (FIG. 6A) between a first optical component 610 and a second optical component 650 when the first and second component 640a and 640b are attached together. When an optical fluid is in the fluid chamber 612, the optical fluid defines an accommodating lens bounded between the first optical component 610 and the second optical component 650. The fluid can flow into and out of the fluid chamber 612 through discrete fluid channels 649 defined by the spaces between standoffs 657 and bonding pins 655 when the first and second components 640a and 640b are assembled.

An additional feature of the AIOL 600 is the distance between the fixed lens 630 and the first optical component 610 that defines the depth of the aqueous chamber 641 (FIG. 6A). The fixed lens 630 is spaced apart from the first optical component 610 such that the first optical component 610 can deflect anteriorly (shown by broken lines) by a sufficient amount to provide the desired accommodation. The distance between the first optical component 610 in an unbiased planar state (shown in solid lines) and the fixed lens 630 can be 1 µm to 4000 µm, or in some applications 4 µm to 800 µm.

The first and second optical components 610 and 650 may be planar members, such as optical membranes, and they may be situated upon mating first and second components 640a and 640b, as shown in FIG. 6C. The AIOL 600 can further include a square-shaped annular region 651 that provides a barrier to cell migration from the periphery of the patient's capsule to the optical field of view of AIOL 600. As shown in FIG. 6A, the square-shaped annular region 651 can define a sharp corner at the posterior most region of the lens to inhibit cell migration that could cause post-surgery opacification of the optical system.

FIGS. 7A and 7B illustrate an embodiment of a second component 740b that can be used in the AIOL 600 illustrated in FIGS. 6A-6C. More specifically, the second component 640b of the AIOL 600 may be replaced with the second component 740b as illustrated in FIGS. 7A and 7B.

703 outer fluid reservoir
740b second component
750 second optical component
756 receivers
757 standoff
760 thickened feature An additional feature of the AIOL 600 is the distance between the fixed lens 630 and the first optical component 610 that defines the depth of the aqueous chamber 641 (FIG. 6a). The fixed lens 630 is spaced apart from the first optical component 610 such that the first optical component 610 can deflect anteriorly (shown in broken lines) by a sufficient amount to provide the desired accommodation. The distance between the first optical component 610 in an unbiased planar state (shown in solid lines) and the fixed lens 630 can be 0.2 mm-2.0 mm, or in some applications 0.4 mm-0.8 mm.

FIGS. 7A and 7B illustrate a top view and sectional side view, respectively, of the second component 740b. The second component 740b comprises a thickened feature 760 that defines a portion of the outer fluid reservoir 703b. The thickened feature 760 provides for a longer material path for use in accessing the interior of the completed assembly via a needle or tubular member to inject a fluid into the interior of the assembly. The longer path of the needle through the bulk material of thickened feature 760 provides for more surface area to seal the path when the needle is removed. This possibly eliminates the need for additional sealing measures after removing the needle. As illustrated, the second component 740b also comprises an alternate bonding pin receiving feature 756 which is comprised of a recess as opposed to a hole as embodied in the bonding pin receiver 656 of AIOL 600.

FIG. 8 illustrates an embodiment of an AIOL 800 that is similar to the embodiments of the AIOLs and components shown in FIG. 6 and FIG. 7. In FIG. 8 various structures are identified by various reference numerals and the last two digits of the reference numerals identify similar structures to those described in embodiments of the AIOls 600 and 700.

800 AIOL system
801 seam
803 outer fluid reservoir
810 first optical component
812 fluid chamber, fluid accommodating lens
830 fixed lens
831 fixed lens receiver
840 accommodating structure
840a first component 840b second component
850 second optical component
851 multiple annular regions
855 standoffs
856 continuous receiver ring
860 thickened features The AIOL 800 includes multiple square-shaped annular regions 851. For example, the AIOL 800 can have 4 circular, square-edged regions 851 incorporated in the posterior (P) and anterior (A) regions of the outer fluid reservoir 803. The square-shaped regions 855 can further inhibit cell migration associated with posterior capsule opacification. The embodiment of the AIOL 800 shown in FIG. 8 additionally incorporates two thickened features 860 in the second component 840b to allow for fluid inflow and fluid outflow during the filling procedure. These thickened features 860 are shown in cross section and subtend circumferential angles similar to that of the thickened feature 760 (FIG. 7). In another variation on the embodiments of the AIOLs 600 and 700, the first component 840a includes standoffs 855 and the second component 840b includes a continuous receiver ring 856 that interfaces with the standoffs 855.

FIGS. 9A-C and 10A-C illustrate embodiments of AIOLs 900 and 1000, respectively, similar to the embodiments AIOLs 600, 700, 800, in which additional features have been incorporated to enhance performance. Various structures are identified by reference numerals in FIGS. 9A-C and 10A-C, and the last two digits of such reference numbers identify similar structures to those described above with reference to FIGS. 6A-8.

900 AIOL
903 outer fluid reservoir
920 passages
930 fixed lens
940 accommodating structure
940a first component
940b second component
955 bonding pin
956 bonding pin receiver
960 thickened features
966 capsular rotation constraint
967 receiver
968 key
969 toric indexing mark
970 toric indexing feature
1000 AIOL
1003 outer fluid reservoir
1030 toric fixed lens
1040 accommodating structure
1040a first component
1040b second component
1055 standoff
1056 receiver ring
1060 thickened feature
1066 capsular rotation constraint
1067 receiver
1068 key
1070 toric indexing feature The embodiments of the AIOLs 900 and 1000 comprise capsular rotation constraint features 966 and 1066, respectively, which enhance performance when the AIOLs 900 and 1000 have a toric lens. The toric lens may be in either the accommodating portion or the fixed portion of the AIOL. The capsular rotation constraint features 966 and 1066 inhibit relative rotation between the optical components themselves and/or with respect to the capsule into which they have been implanted. As illustrated here, the fixed lenses 930 and 1030 are toric lenses. The capsular rotation constraints 966 (FIGS. 9A and 9C) and 1066 (FIGS. 10A and 100) are located on the outer periphery of the device to engage the lens capsule of the eye and inhibit rotation of the AIOL system within the native lens capsule. The capsular rotation constraints 966 and 1066 can be thickened portions of the first and/or second component 940a/1040a or 940b/1040b on the outer periphery of the AIOLs 900 and 1000, respectively. Alternate embodiments for the capsular rotation constraints can include any feature that engages the native capsule more securely than other surfaces on the periphery of the AIOL to inhibit rotation of the AIOL with respect to the native eye capsule. Alternatively, the AIOLs 900 or 1000 can have only single capsular rotation constraint 966 or 1066 or more than two capsular rotation constraints 966 or 1066.

Figure 10A:
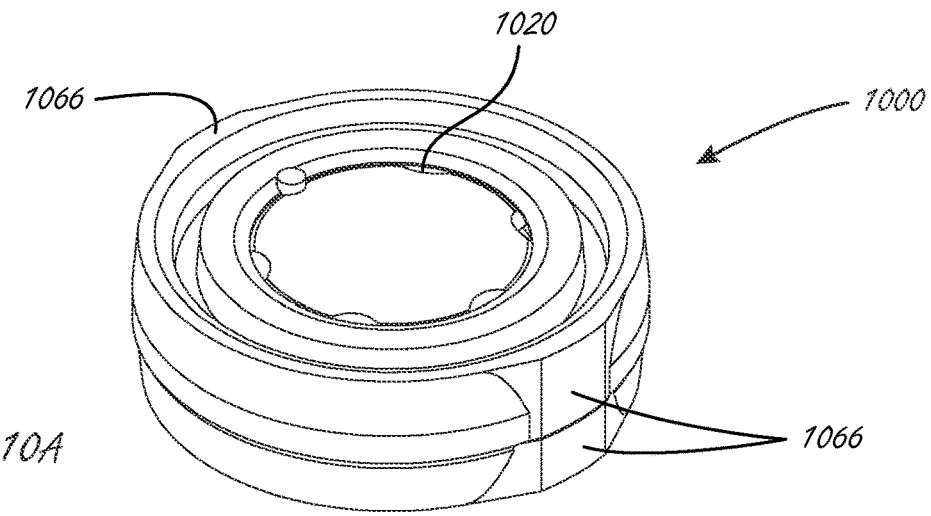
FIGS. 10A-10C illustrate accommodating intraocular lens systems 1000 incorporating additional features to enhance performance.
Figure 10B:
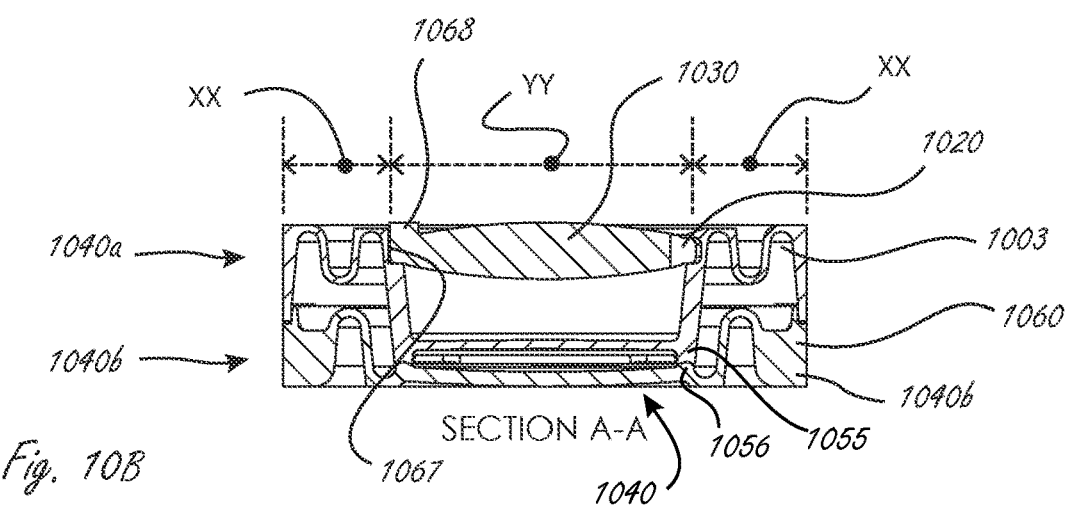
Figure 10C:
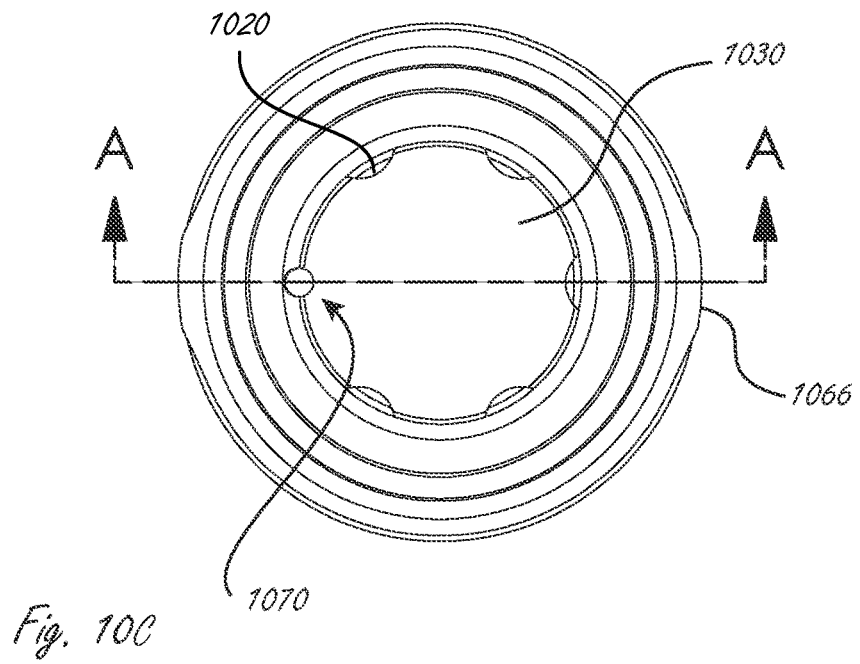

In addition to the capsular rotation constraints 966 and 1066, the AIOLs 900 and 1000 can also include features that maintain the rotational orientation of the fixed lens 930/1030 relative to the accommodating structures 940/1040 of the AIOLs 900/1000. The capsular rotation constraints 966/1066 can define toric indexing features of the AIOLs 900 and 1000 that reference the rotational orientation of the fixed lens 930/1030 relative to the accommodating structures 940/1040. The fixed lens 930 of the AIOL 900 can also have a plurality of passages 920 defined by cutouts or holes along the perimeter of the fixed lens 930, and one of the passages 920 defines a receiver 967 at a location to guide the proper orientation of the fixed lens 930 with respect to the first component 940a. The first component 940a comprises a key 968 at a corresponding radial location to align the toric fixed lens 930. The receiver 967 and the key 968 together define a toric indexing feature 970. The fixed lens 930 can further include a toric indexing mark 969 on, or in, the fixed lens 930 that identifies which passage 920 defines the receiver 967 that is to be aligned with the key 968. Alternatively, instead of having the toric indexing mark 969, the key/receiver associated with the correct alignment can have a different shape (e.g., triangular) than the other passages 920 in the lens (e.g., curved). FIG. 10B illustrates an alternate embodiment in which the receiver 1067 is a cutout or recess in the inner perimeter of the first component 1040a, and the toric fixed lens 1030 comprises a key 1068 configured to mate with the receiver 1067.

Figure 11:
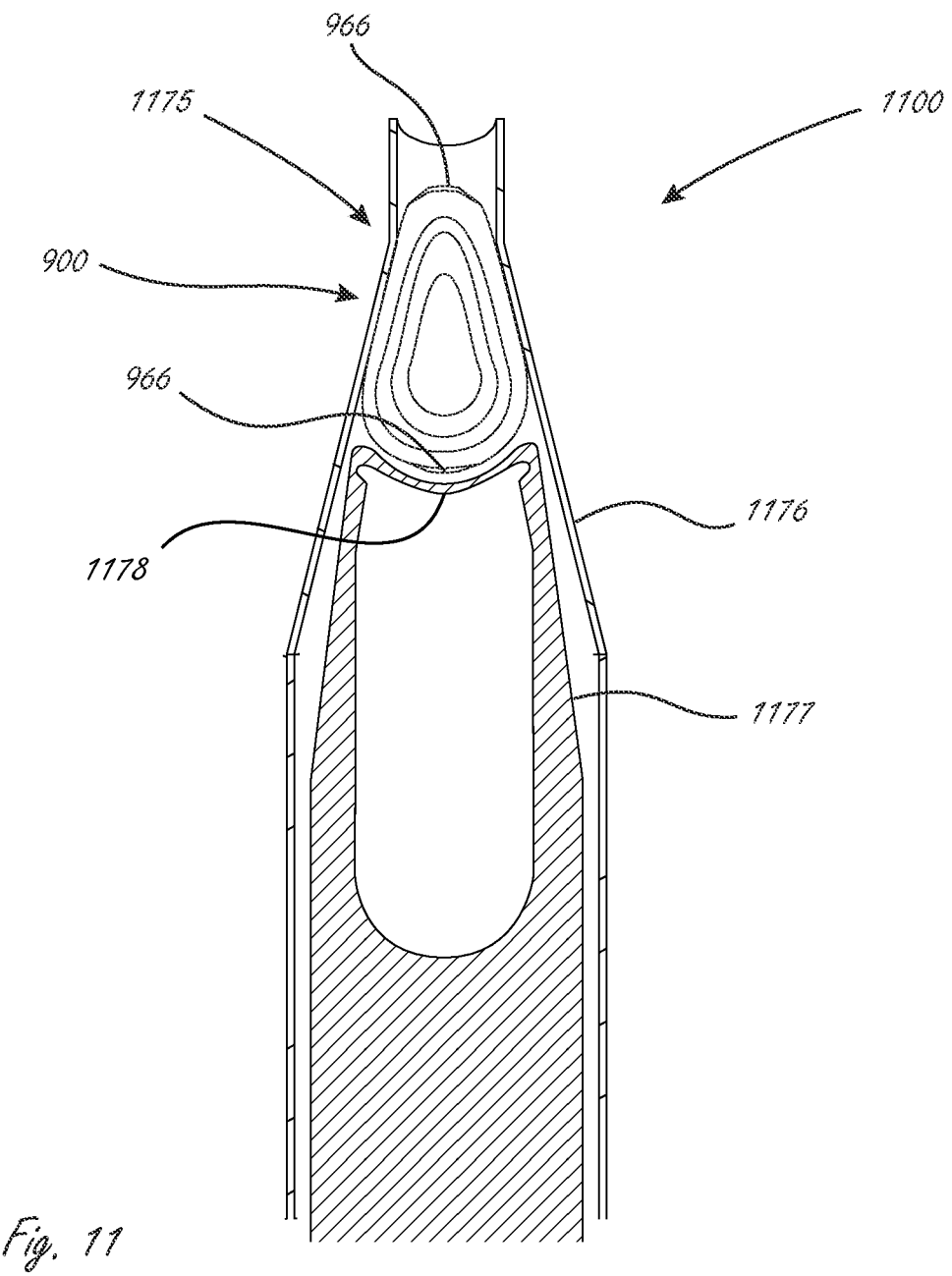
FIG. 11 depicts AIOL delivery device 1100 with a properly oriented lens system entering the injector tip for delivery.

The thickened regions of the capsular rotation constraints 966 and 1066 of the AIOLs 900 and 1000 further provide a more robust leading edge for use when delivering the AIOLs 900 and 1000 through a narrow bore constriction or tube of an AIOL delivery device as described with respect to FIG. 11. One of the thickened rotation constraints 966 and 1066 can be positioned to be a leading edge of the AIOL systems 900 and 1000 and the other a trailing edge as they are passed through the narrow bore or tube of a delivery device. By having the thickened rotation constraints 966, 1066 define a leading edge during delivery, the leading portion of the AIOLs 900, 1000 can sustain larger pressures as the leading section of the AIOLs 900, 1000 compresses during the delivery process when the most distal portion has entered the constricted zone of the delivery tool. More specifically, fluid trapped in the AIOLs 900 and 1000 can rupture the material as the leading edge is compressed. Thus, increasing the thickness of the material at the leading edge enables the AIOLs 900 and 1000 to withstand the compression forces during delivery. In some embodiments, the AIOLs 900 and 1000 have only a single rotation constraint 966/1066.

FIG. 11 schematically illustrates how one of the thickened rotational constraints 966 of the AIOL system 900 operates in a distal tip of a delivery device 1100 during delivery. Various structures are identified by reference numerals in FIG. 11, and the last two digits of such reference numbers identify similar structures to those described above with reference to FIGS. 6A-10C.

- 1100 AIOL delivery device
- 900 AIOL
- 966 capsular rotation constraint
- 1175 injector tip
- 1176 insertion funnel
- 1177 plunger
- 1178 flexible distal end The AIOL 900 is shown properly oriented relative to the capsular rotation constraints 966 and entering the injector tip 1175 for delivery. The AIOL 900 conforms to the delivery tool constrictions while being pushed through an insertion funnel 1176 by a flexible distal end 1178 of a plunger 1177. It will be appreciated that the internal pressure of the fluid in the AIOL 900 increases as it is compressed in the insertion funnel 1176, and the thickened rotation constraint 966 at the leading edge provides more material to withstand the increase in pressure and protect the front end from rupturing during delivery.

Figure 12A:
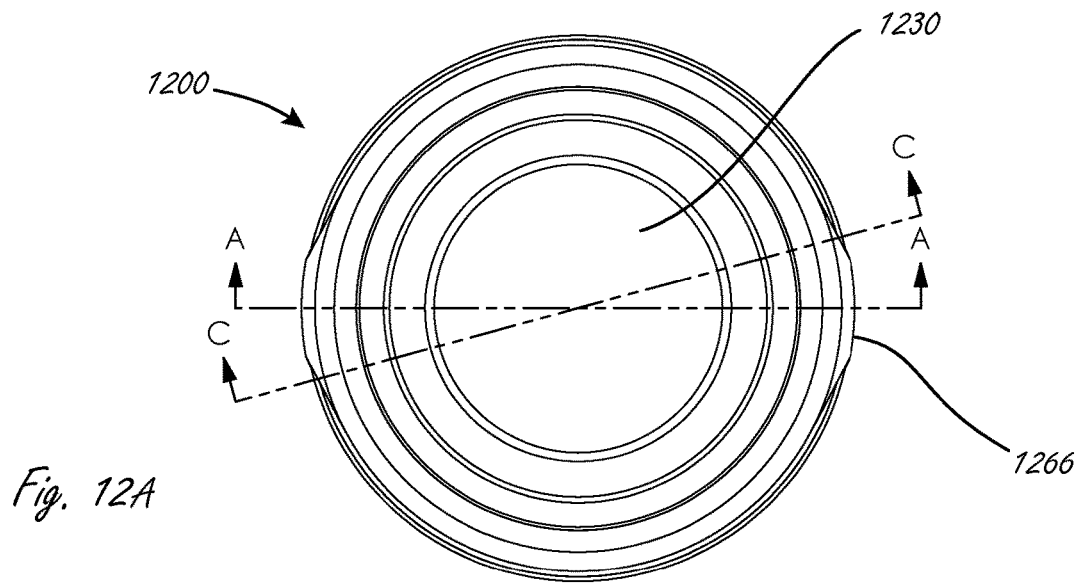
FIGS. 12A-12C present an AIOL embodiment comprising a mid-bellows stabilizing feature.
Figure 12B:
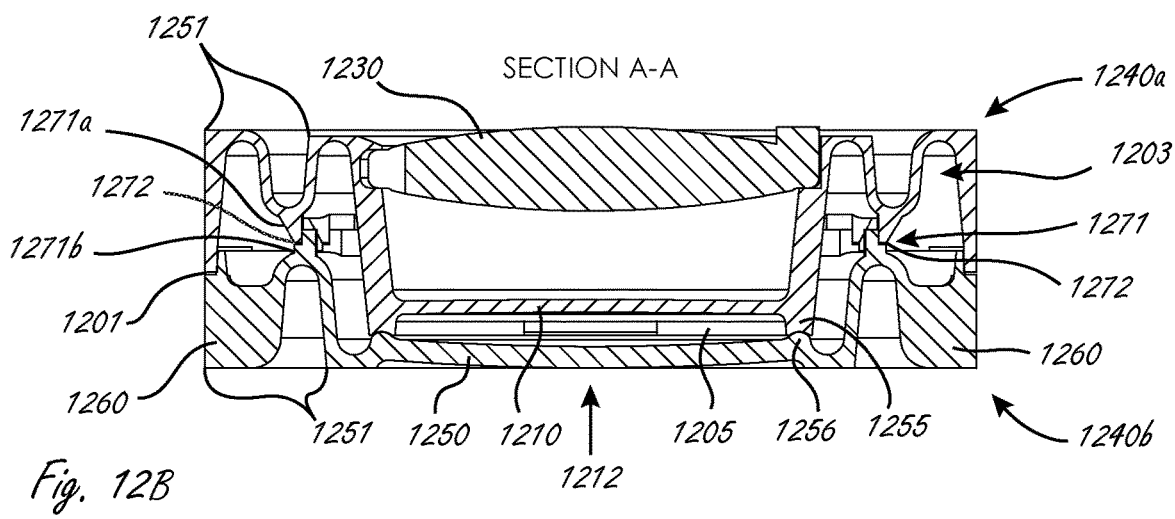
Figure 12C:
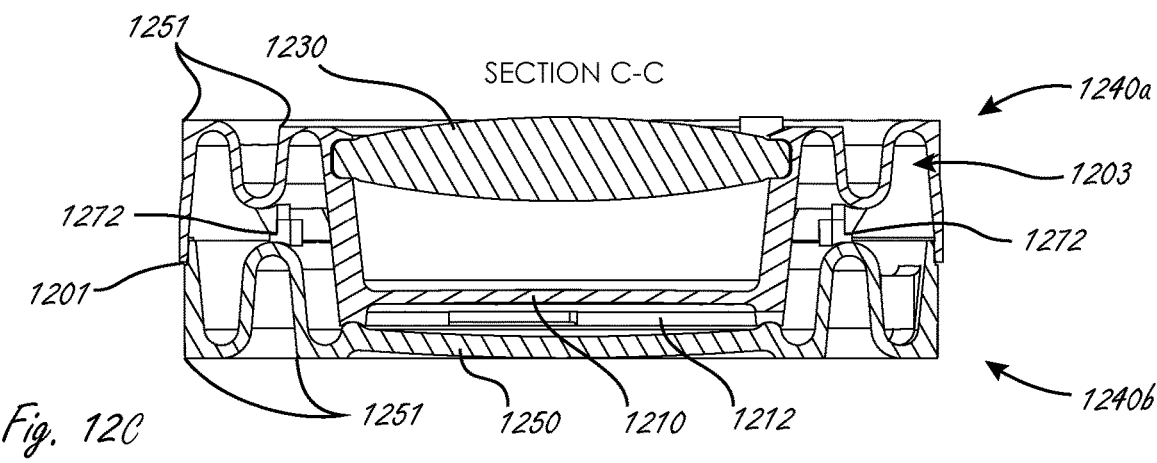

FIGS. 12A-12C illustrate an alternative AIOL 1200 comprising at least one mid-bellows attachment feature 1271 (shown in the cross-sectional views of in FIGS. 12B-12C). Various structures are identified by reference numerals in FIG. 12, and the last two digits of such reference numbers identify similar structures to those described above with reference to FIGS. 6A-10C.

- 1200 AIOL
- 1201 seam
- 1203 outer fluid reservoir
- 1205 fluid chamber
- 1210 first optical component
- 1212 fluid accommodating lens
- 1230 fixed lens
- 1240*a* first component
- 1240*b* second component
- 1250 second optical component
- 1251 square-shaped annular edge
- 1255 standoff
- 1256 receiver ring
- 1260 thickened feature
- 1266 capsular rotation constraint
- 1271 mid-bellows attachment feature
- 1271*a* first mating element
- 1271*b* second mating element
- 1272 mating region The AIOL 1200 is similar to the embodiment of the AIOL 1000 described herein. For example, the illustrated embodiment of the AIOL 1200 comprises first and second components 1240*a* and 1240*b*, respectively, that are bonded together at a seam 1201 to define an outer fluid reservoir 1203. The AIOL 1200 further comprises a fixed lens 1230, a first optical component 1210, a second optical component 1250, and a fluid chamber 1205 between the first and second optical components 1210 and 1250. At least one of the first and second optical components 1210 and 1250 is deformable (e.g., able to flex anteriorly and/or posteriorly), and in several embodiments the first optical component 1210 is more deformable than the second optical component 1250. For example, the first optical component 1210 can be a thin flexible member, while the second optical component 1250 is at least substantially rigid (e.g., does not flex in a manner that changes the optical power). The first optical component 1210 and/or the second optical component 1250 in combination with an optical fluid in the fluid chamber 1205 define a fluid accommodating lens 1212. The AIOL 1200 also includes (a) thickened features 1260 that facilitate fluid delivery during the filling procedure as described herein with respect to features 760, and (b) a square-shaped annular edge 1251 that provides a barrier to inhibit cell migration from the periphery of the patient's capsule to portions of the AIOL 1200 within the optical path.

The AIOL 1200 includes mid-bellows attachment features 1271 that each comprise first and second mating elements 1271*a* and 1271*b* integrated into the first and second components 1240*a* and 1240*b*, respectively. The first and second mating elements 1271*a* and 1271*b* are joined together at a mating region 1272. The mid-bellows attachment features 1271 may be distributed circumferentially around the midsection of the outer fluid reservoir 1203 at a plurality of discrete locations that are spaced apart from each other. For example, in the embodiment of the AIOL 1200 shown in FIGS. 12A-12C, the mid-bellows attachment features 1271 are evenly distributed at eight locations (not all are shown) spaced apart around the midsection of the outer fluid reservoir 1203, however the mid-bellows attachment features 1271 are not limited to a specific quantity.

The mid-bellows attachment features 1271 provide a more efficient transfer of fluid from the outer fluid reservoir 1203 to the fluid chamber 1205 of the AIOL 1200. More specifically, without the mid-bellows attachment features 1271, the apexes of the periphery of the first and second components 1204*a* and 1204*b* can separate from each other as pressure increases in the outer fluid reservoir 1203 during accommodation. The mid-bellows attachment features 1271 may limit such undesirable or excessive expansion in the midsection of the outer fluid reservoir 1203 during accommodation by inhibiting separation of the apexes of the periphery of the first and second components 1204*a* and 1204*b*. Conversely, the mid-bellows attachment features 1271 can support the midsection of the outer fluid reservoir 1203 to inhibit it from collapsing and trapping fluid in the outer fluid reservoir 1203. The mid-bellows attachment features 1271 accordingly stabilize the volume of the midsection of the outer fluid reservoir 1203 as pressure increases in the outer fluid reservoir 1203 such that more of the fluid flows from the outer fluid reservoir 1203 and into the fluid chamber 1205 than without the mid-bellows attachment features 1271. This provides for a more efficient transfer of the accommodating fluid from the outer fluid reservoir 1203 to the fluid chamber 1205 of the fluid accommodating lens 1212. FIG. 12B illustrates a section through the AIOL 1200 which passes through two of the mid-bellows attachment features 1271, and FIG. 12C illustrates a section of the AIOL 1200 that passes through two spaces between mid-bellows attachment features 1271 that allow fluid to pass from the outer fluid reservoir 1203 to the fluid chamber 1205.

The mid-bellows attachment features 1271 are not limited to use in the embodiments of the AIOL 1200 described above with reference to FIGS. 12A-12C, but rather may be incorporated into any appropriate embodiment of an AIOL with an outer fluid reservoir and a fluid chamber disclosed herein.

Additional embodiments of AIOLs 1300, 1400, 1500, and 1600, are illustrated in FIGS. 13A through 16B, and each of the AIOLs 1300, 1400, 1500 and 1600 comprise flow features which facilitate the flow of materials from the posterior side of the AIOL to the anterior side of the AIOL. These flow features may reduce or eliminate the trapping or stagnation of materials between the capsule and the posterior aspect of the AIOL. In particular, these flow features may enhance the rate and ease with which Ophthalmic Viscosurgical Devices (OVDs) used during the implantation of AIOLs can be removed from the natural lens capsule.

The AIOL 1300 illustrated in FIGS. 13A through 13J comprises two different flow features: a first flow feature is defined by outer flow-throughs 1381 and a second flow feature is defined by inner flow-throughs 1382.

1300 AIOL
1301 seam
1302 protrusions
1303 outer fluid reservoir
1303a first bellows structure
1303b second bellows structure
1310 first optical component
1305 fluid chamber
1330 fixed lens
1331 fixed lens receiver
1340a first component
1340b second component
1349 fluid channel
1351 square-shaped annular edge
1355 standoff
1356 bonding pin receiver
1360 thickened features
1371 mid-bellows attachment feature
1371a first mating element
1371b second mating element
1373 mid-bellows channels
1381 outer flow-through, recess
1382 inner flow-through, hole The outer flow-through feature 1381 can be detents, such as a recess, at regions around the perimeter of the device. The inner flow-through feature 1382 can be a mid-bellows through hole that passes through portions of two of the mid-bellows attachment features 1371 between mid-bellows channels. As illustrated, the inner flow-throughs 1382 comprise circular holes, but in alternate embodiments the inner flow-throughs 1382 may be slots. Although only two inner flow-throughs 1382 are illustrated, the AIOL 1300 may comprise more than two. In general, there can be as many inner flow-throughs 1382 as there are mid-bellows attachment features 1371. In some embodiments, the inner flow-throughs 1382 may be added after fabricating the AIOL 1300 by laser cutting or drilling, or in other embodiments the inner flow-throughs 1382 can be formed in the parts prior to assembly (e.g., molded or cut into the parts before assembly). Although two outer flow-throughs 1381 are illustrated, other embodiments of the AIOL 1300 may comprise fewer or more than two flow-throughs. The outer flow-throughs 1381 additionally provide rotational constraint as described above with regard to the embodiment of the AIOL 1000.

FIGS. 14 and 15 present AIOL embodiments 1400 and 1500, respectively, with the following feature references:

1400 AIOL
1403 outer fluid reservoir
1420 passages
1430 fixed lens
1432 skirt
1436 optical portion
1440a first component
1473 mid-bellows channels
1500 AIOL
1520 passages
1530 fixed lens
1531 engagement feature
1532 skirt
1536 optical portion
1540a first component The embodiments of AIOLs 1400 and 1500 have fixed lens assemblies 1430 and 1530, respectively, that (a) allow fluid to flow through the fixed lens assemblies, (b) center the fixed lens assemblies 1430 and 1530 in the device, and (c) enhance the structural stiffness at the inner area of the outer fluid reservoir 1403. The fixed lens assembly 1430 illustrated in FIG. 14C includes an optical portion 1436, a skirt 1432 extending from the optical portion 1436, and passages 1420. The optical portion 1436 has a fixed power as explained above, and the passages 1420 are holes, slots, orifices, etc., that pass through the skirt 1432 and extend into a perimeter region of the optical portion 1436. The fixed lens assembly 1530 shown in FIG. 15A can similarly include an optical portion 1536, a skirt 1532 extending from the optical portion 1536, and passages 1520 through the skirt and into a perimeter region of the optical portion 1536. In these embodiments, the passages 1420 and 1520 provide for fluid transfer as previously described with respect to, e.g., through hole 620 described herein with reference to AIOL 600. The passages 1420 and 1520 also reduce the volume of the fixed lens allowing them to be delivered through a smaller delivery tool.

Referring to FIGS. 14D and 14E, the skirt 1432 of the fixed lens assembly 1430 diverges radially outward from the anterior side A to the posterior side P of the AIOL 1400 (i.e., in the posterior direction the skirt 1432 is inclined outwardly to slope away from the optical axis of the optical portion 1436). This allows the inner wall of the first component 1440a to retain the fixed lens assembly 1430. The AIOL 1400 also can include a mid-bellows channel 1473 (illustrated in FIGS. 14D and 14E) that allows fluid to flow from the outer portion to an inner portion of the outer fluid reservoir 1403 (FIG. 14E).

Referring to FIGS. 15C and 15D, the skirt 1532 of the fixed lens 1530 converges radially inward from the anterior side A to the posterior side P of the AIOL 1500 (i.e., in the posterior direction the skirt 1532 is inclined inwardly to slope toward the optical axis of the optical portion). The AIOL 1500 further includes a lip 1531 around the anterior region of the fixed lens assembly 1530 to retain the fixed lens assembly 1530 in the desired position.

During implantation, when the folded fixed lens is delivered into the eye after the accommodating portion has been delivered, the skirt centers the fixed lens as it unfolds and securely holds the fixed lens within the accommodating portion when fully expanded. More specifically, either skirt 1432 or 1532 will automatically position the optical portion 1436 and 1536, respectively, at the desired position relative to the optical axes of the devices as the skirts 1432 and 1532 engage the first components 1440a and 1540a. Additionally, the height/depth of the skirts 1432 and 1532 will also space the optical portion 1436 and 1536, respectively, at a desired distance from the first optical components 1410 and 1510 of the accommodating lenses. This will allow a practitioner to press the fixed lens assemblies 1430 and 1530 into place without risking pushing the optical portions 1436 and 1536 too far into the first structural elements 1440a and 1540a.

Figure 16A:
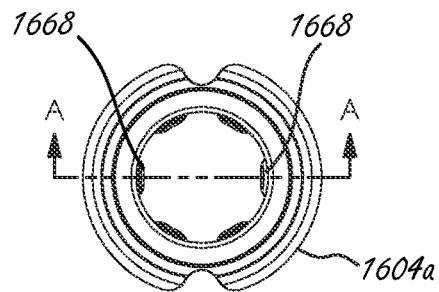
FIGS. 16A-16B illustrate a structural element comprising one or more thickened portions on an inner wall, shaped to interface with one or more passages.
Figure 16B:
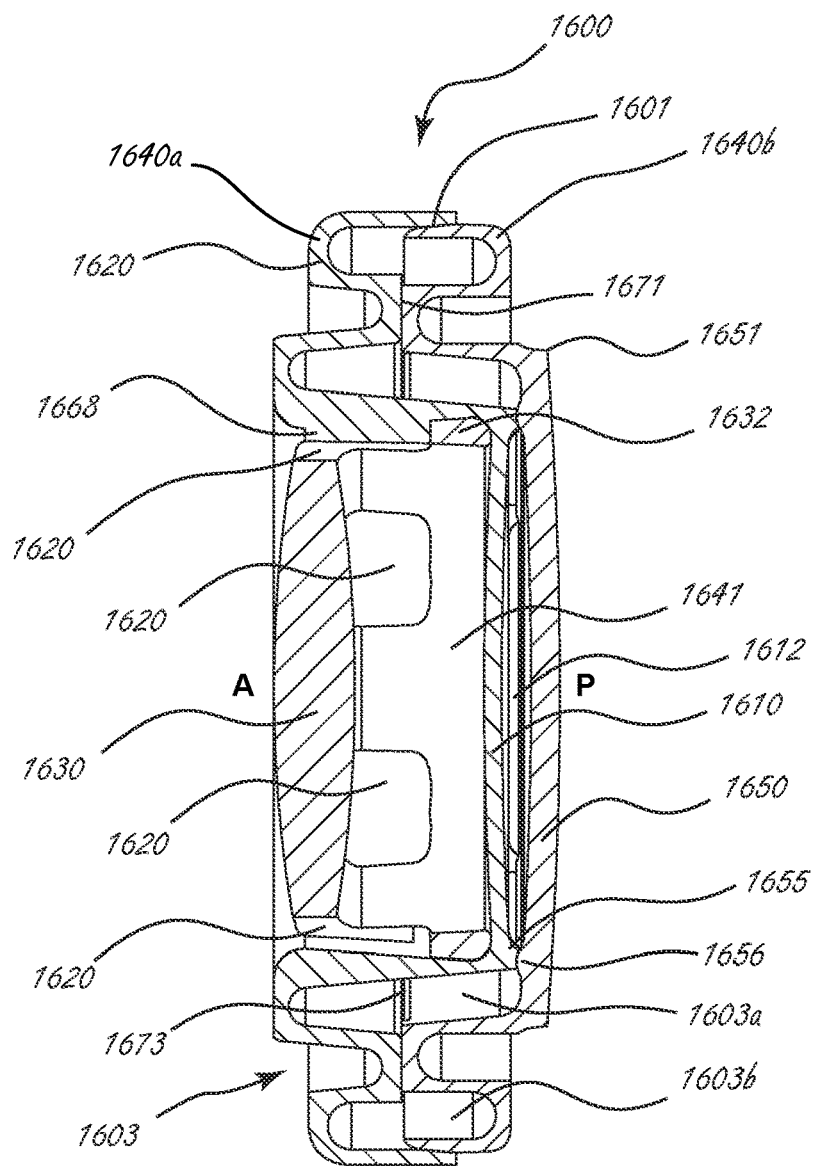

FIGS. 16A and 16B illustrate an AIOL 1600 similar to the embodiment of the AIOL 1400. The AIOL 1600 has a first component 1640a comprising at least one thickened portion 1668 on the inner wall that is shaped to interface with one or more of the passages 1620 in the fixed lens assembly 1630.

1600 AIOL system
1601 seam
1603 outer fluid reservoir 1603a first bellows structure
1603b second bellows structure
1610 first optical component
1620 passages
1630 fixed lens
1632 skirt
1636 optical portion
1640 accommodating structure
1640a first component
1640b second component
1641 chamber
1650 second optical component
1651 multiple annular region
1655 standoff
1656 receiver ring
1668 thickened portions
1671 mid-bellows attachment feature
1673 mid-bellows channel The interface between the thickened portions 1668 and the respective passage 1620 securely fixes the fixed lens 1630 in place and provides for proper alignment of the fixed lens 1630 when the fixed lens 1630 comprises a toric configuration. In such an embodiment, the fixed lens 1630 may comprise any of the orientation markings described elsewhere herein.

FIGS. 17A-17G have the following features.
1700 AIOL
1701 seam
1703 outer fluid reservoir
1703a first bellows structure
1703b second bellows structure
1705 fluid chamber
1708 bellows
1710 first optical component
1712 space
1720 passages
1730 fixed lens
1731 engagement feature
1732 skirt
1736 optical portion
1740 accommodating structure
1740a first component
1740b second component
1741 chamber
1749 fluid channel
1750 second optical component
1751 square-shaped annular edge
1755 standoff
1756 receiver ring
1760 fluid fill thickened section
1768 lens engagement thickened region
1771 mid-bellows attachment feature
1773 mid-bellows channel
1781 outer flow-through features FIGS. 17A and 17B illustrate an embodiment of an AIOL 1700 that includes enhanced flow-through features 1781 to facilitate the flow of materials from the posterior side of the AIOL 1700 to the anterior side of the AIOL 1700. In particular, the flow-through features 1781 may enhance the rate and ease with which Ophthalmic Viscosurgical Devices (OVDs) used during the implantation of AIOLs can be removed from the natural lens capsule. The embodiment of the AIOL 1700 illustrated in FIGS. 17A-17E comprises three outer flow-through features 1781. The outer flow-through features 1781 can be detents, such as a recess, distributed circumferentially along the perimeter of the outer fluid reservoir 1703. In the illustrated embodiment, the flow-through features 1781 are formed in regions of the first and second components 1740a and 1740b. Although three outer flow-through features 1781 are illustrated, other embodiments may comprise less or more than illustrated. The outer flow-through features may additionally provide rotational constraint as described herein with regard to the AIOL of embodiment 1000.

The embodiment of the AIOL 1700 additionally comprises an alternate design for a fixed lens assembly 1730. The fixed lens assembly 1730 illustrated in FIG. 17C includes an optical portion 1736, a skirt 1732 extending from the optical portion 1736, and passages 1720. The optical portion 1736 has a fixed power which may comprise an asymmetrically powered lens or other lens as explained herein, and the passages 1720 are holes, slots, orifices, etc., that pass through the skirt 1732 and extend into a perimeter region but not the optical portion 1736.

Referring to FIG. 17C, the fixed lens assembly 1730 has an engagement feature 1731, such as an annular groove, that extends around the skirt 1732, and the first component 1740a of the accommodating structure 1740 has a thickened region 1768, such as an annular protrusion (e.g., a ledge) that extends radially inwardly. The fixed lens assembly 1730 can be attached to the accommodating structure 1740 by engaging the continuous thickened region 1768 of the first component 1740a with the engagement feature 1731 of the fixed lens 1730. In other embodiments (not shown), the thickened region 1768 and the engagement feature 1731 may be discontinuous features (e.g., segmented or other recesses or protrusions that extend around less than the full circumference of the fixed lens assembly 1730 and the accommodating structure 1740). Such discontinuous thickened region 1768 and engagement feature 1731 are desirable to maintain a particular radial alignment between the fixed lens assembly 1730 and the accommodating structure 1740, such as when the fixed lens 1730 comprises a toric lens or other asymmetrical lens. Alternatively, the groove may be in the fixed lens 1730 and the protrusion on the accommodating structure 1740.

The AIOL 1700 has a fluid accommodating lens 1712 defined by a fluid chamber 1705 (FIGS. 17D and 17E) bounded between a first optical component 1710 and a second optical component 1750. The fluid chamber 1705 is in fluid communication with the outer reservoir 1703 via discrete fluid channels 1749 between standoffs 1756 when the first and second components 1740a and 1740b are assembled. The first and second optical components 1710 and 1750 may be planar members (e.g., optical membranes) of the first and second components 1740a and 1740b, respectively, as shown in FIG. 17E. The first and second optical components 1710 and 1750, for example, can be integrally formed as optical membranes with the other portions of the first and second components 1740a and 1740b. In alternate embodiments, either or both of the membranes of the first and second optical components 1710 and 1750 may be a lens (i.e., have an optical power).

The AIOL 1700 can further include a square-shaped annular region 1751 that inhibits cell migration from the periphery of the patient's capsule to the optical part of AIOL 1700 (shown in FIG. 17D at the posterior most region of the lens). Such cell migration could cause post-surgery opacification of the optical system.

The peripheral portions of the first component 1740a and the second component 1740b define the outer fluid reservoir 1703, and the inner portions of the first and second components 1740a and 1740b define the accommodating structural element 1740. The first and second components 1740a and

1740*b* can be bonded together at a seam 1701 by means as described elsewhere herein. The first and second components 1740*a* and 1740*b* can also be bonded at other areas, such as at the standoffs 1755. The standoffs 1755 are separated by spaces that define fluid channels 1749 between the outer fluid reservoir 1703 and the inner fluid chamber 1705. The outer fluid reservoir 1703 can be a bellows 1708 having an outer bellows region 1703*a* and an inner bellows region 1703*b*.

The outer fluid reservoir 1703 has less volume that the outer fluid reservoirs of other AIOLs described herein, and in particular the volume of the inner bellows region 1703*b* is less than the outer bellows region 1703*a*. By reducing the volume of the inner bellows region 1703*b*, additional space surrounding the optical region of the AIOL allows the optical aperture of the fixed lens 1730 to be larger compared to embodiments with larger inner bellows regions. Additionally, the passages 1720 of the fixed lens 1730, which allow aqueous fluid to freely flow in and out of the chamber 1741, are configured to pass through only the outer skirt 1732 and not the top optical portion 1736. This is expected to reduce unwanted scattered light from internal reflections which may pass through the optical system and reach the retina.

The first component 1740*a* may also comprise one or more thickened regions 1760 for use as described above with respect to, for instance, the thickened region 1760 of the AIOL 700 for use in filling the AIOL with an optical fluid. The thickened region 1760 allows for a longer path for a needle used to fill the accommodating structure with optical fluid while a second needle in a different region is used to remove the gases the fluid is replacing. As illustrated, the fluid fill thickened region 1760 is located adjacent one or more of the outer fluid flow-throughs 1781.

Referring to FIG. 17E, the outer fluid reservoir 1703 of the AIOL 1700 can comprise (a) a first bellows structure 1703*a* with an anterior portion 1704*a* and a posterior portion 1704*b*, (b) a second bellows structure 1703*b* radially inward of the first bellows structure 1704*a*, and (c) a mid-bellows channel structure 1773 defining a horizontal passageway between the first and second bellows structures 1703*a* and 1703*b*. During operation as the capsule contracts, a mid-portion of the first bellows structure 1703*a* is constrained by the mid-bellows channel 1773 while the anterior and posterior portions 1704*a* and 1704*b* of the first bellows structure 1703*a* move radially inward with respect to the mid-bellows channel 1773. The anterior and posterior portions 1704*a* and 1704*b* of the first bellows structure 1703*a* will accordingly flex radially inward to a greater extent than some other outer reservoir structures described above (e.g., outer fluid reservoir 103 shown in FIG. 1) in response to the same amount of movement of the native capsule. This causes more fluid to flow from the outer fluid reservoir 1703 to the inner fluid chamber 1705 and thereby provides more accommodation because anterior-posterior collapse of the outer fluid reservoir 1703 is less efficient than radial compression of the outer fluid reservoir 1703.

Figure 13G:
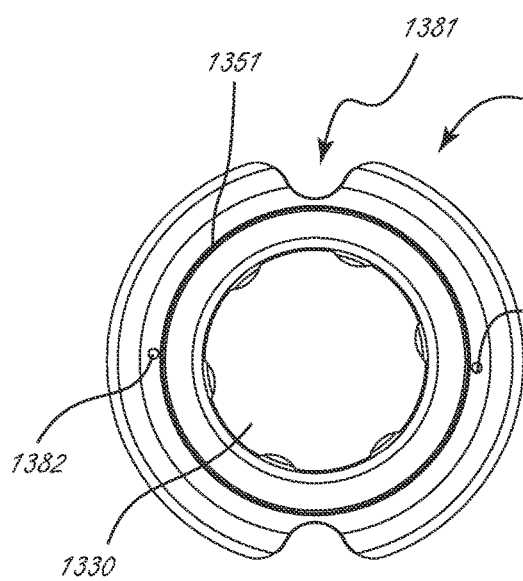
Figure 13H:
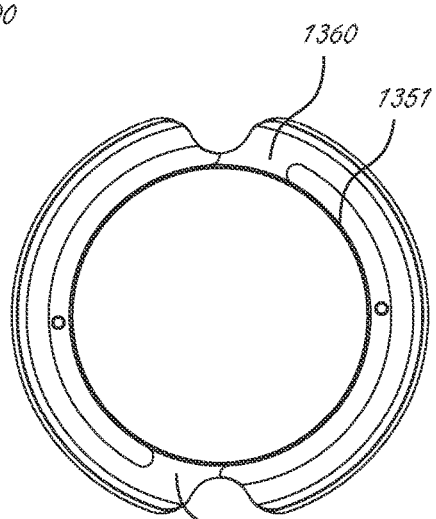
Figure 13I:
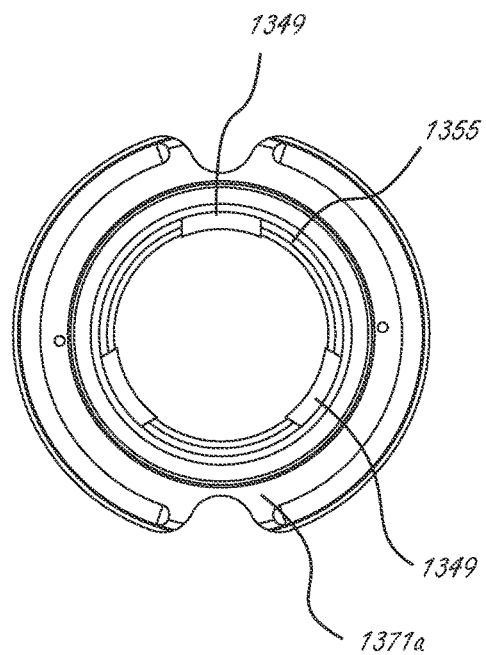
Figure 13J:
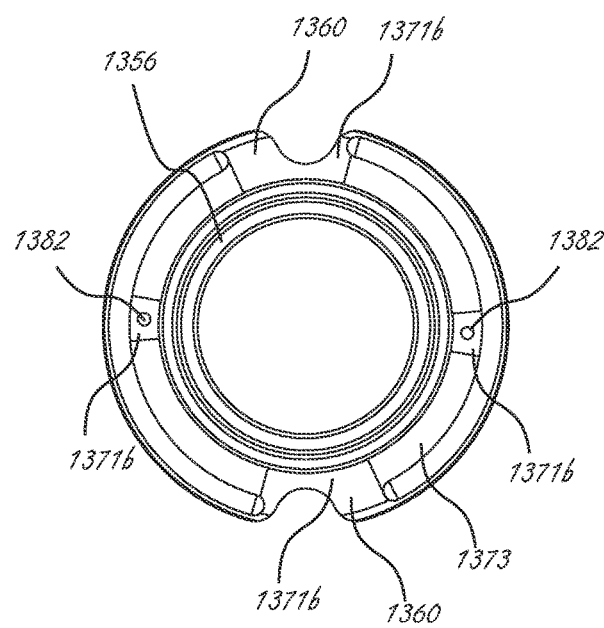

FIGS. 17F and 17G show channels 1744 that extend around the perimeter of the first and second components 1740*a* and 1740*b* to narrow the space for the thickened portions 1760 compared to, e.g., the thickened portions 1360 shown in FIGS. 13I and 13J. The narrower thickened portions 1760 are more flexible than the thickened portions 1360, which enhances the amount of fluid transport between the outer fluid reservoir 1703 and the inner fluid chamber 1705 in response to the same amount of movement of the native capsule.

Although not shown, in some embodiments, a portion of the outer structure of the accommodating structure 1740, between two of the outer flow-through features 1781, may comprise a thickened section providing for the improved delivery function described above with respect to the thickened feature 1668.

In some embodiments, the standoffs 1755 may be bonded to the second component 1740*b*, in alternate embodiments the standoffs 1755 may not be bonded to another component. In either case, the interaction of the skirt 1732 with the perimeter of the second optical component 1750 will minimize non-uniform deformations in one or both of the first and second optical components 1710 and 1750 originating at their outer periphery and thereby reduce optical aberrations.

In some embodiments not shown the inner surfaces of the bellows region 1708 of 1740*a* and or 1740*b* may comprise standoffs which constrain portions of the bellows from collapsing and forming a seal on compression.

FIGS. 18A-18D illustrate an embodiment of an AIOL 1800 in accordance with an embodiment of the present technology. FIGS. 18A-18D have the following features.

1800 AIOL
1801 seam
1803 outer fluid reservoir
1803*a* first bellows structure
1803*b* second bellows structure
1805 fluid chamber
1808 bellows
1810 first optical component
1812 fluid accommodating lens
1820 passages
1830 fixed lens
1831 engagement feature
1832 skirt
1836 optical portion
1840 accommodating structure
1840*a* first component
1840*b* second component
1841 chamber
1850 second optical component
1851 square-shaped annular edge
1855 standoff
1857 recesses
1858 wall
1860 fluid fill thickened section
1868 lens engagement thickened region
1871 mid-bellows attachment feature
1873 mid-bellows channel
1881 outer flow-through features FIGS. 18A-D illustrate an embodiment of an AIOL 1800 that includes different channels for fluid to flow from the outer fluid reservoir to the inner fluid chamber. Referring to FIG. 18B, the AIOL 1800 has an accommodating structure 1840 having a first component 1840*a* and the second component 1840*b*. As described above, the first and second components 1840*a* and 1840*b* are assembled to form an outer fluid reservoir 1803, a mid-bellows channel 1873, and an inner fluid chamber 1805. The first component 1840*a* of the accommodating structure 1840 can have an inner portion with a first optical component 1810, standoffs 1855, and recesses 1857 between the standoffs 1855. The standoffs 1855 project radially outward from the recesses 1857. The second component 1840*b* of the accommodating structure 1840 can have an inner portion with a second optical component 1850 and a wall 1858. Referring to FIGS. 18C and 18D, which are cross-sectional views taken along lines A-A and B-B of FIG. 18A, respectively, the standoffs 1855 contact the wall 1858 (FIG. 18D) such that the recesses 1857 (FIG. 18B) define channels for fluid to flow from the mid-bellows channel 1873 to the fluid chamber 1805.

The interface between the standoffs 1855 and the wall 1858 of the accommodating structure 1840 are different than the interface between the standoffs 1755 and the second optical component 1750 described above with reference to the AIOL 1700. More specifically, the standoffs 1855 project radially outward to engage the wall 1858, whereas the standoffs 1755 are within the optical region of the device and project posteriorly. The standoffs 1855 of the AIOL 1800 accordingly do not extend into the optical region of the AIOL, which increases the field of view of the AIOL 1800 compared to the AIOL 1700.

As with the AIOL 1700 described above, the AIOL 1800 includes flow-through features 1881 that enhance the rate and ease with which Ophthalmic Viscosurgical Devices (OVDs) used during the implantation of AIOLs can be removed from the natural lens capsule. The embodiment of the AIOL 1800 illustrated in FIGS. 18A-18D comprises three outer flow-through features 1881. The outer flow-through features 1881 can be detents, such as a recess, distributed circumferentially along the perimeter of the outer fluid reservoir 1803. In the illustrated embodiment, the flow-through features 1881 are formed in regions of the first and second components 1840a and 1840b. Although three outer flow-through features 1881 are illustrated, other embodiments may comprise less or more than illustrated. The outer flow-through features may additionally provide rotational constraint as described herein with regard to the AIOL of embodiment 1000.

The embodiment of the AIOL 1800 additionally comprises a fixed lens assembly 1830. The fixed lens assembly 1830 illustrated in FIGS. 18C-D includes an optical portion 1836, a skirt 1832 extending from the optical portion 1836, and passages 1820. The optical portion 1836 has a fixed power which may comprise an asymmetrically powered lens or other lens as explained herein, and the passages 1820 are holes, slots, orifices, etc., that pass through the skirt 1832 and extend into a perimeter region but not the optical portion 1836.

Referring to FIG. 18C, the fixed lens assembly 1830 has an engagement feature 1831, such as an annular groove, that extends around the skirt 1832, and the first component 1840a of the accommodating structure 1840 has a thickened region 1868, such as an annular protrusion (e.g., a ledge) that extends radially inwardly. The fixed lens assembly 1830 can be attached to the accommodating structure 1840 by engaging the continuous thickened region 1868 of the first component 1840a with the engagement feature 1831 of the fixed lens 1830. In other embodiments (not shown), the thickened region 1868 and the engagement feature 1831 may be discontinuous features (e.g., segmented or other recesses or protrusions that extend around less than the full circumference of the fixed lens assembly 1830 and the accommodating structure 1840). Such a discontinuous thickened region 1868 and engagement feature 1831 are desirable to maintain a particular radial alignment between the fixed lens assembly 1830 and the accommodating structure 1840, such as when the fixed lens 1830 comprises a toric lens or other asymmetrical lens. Alternatively, the groove may be in the fixed lens 1830 and the protrusion on the accommodating structure 1840.

The AIOL 1800 has a fluid accommodating lens 1812 defined by a fluid chamber 1805 (FIGS. 18C and 18D) bounded between a first optical component 1810 and a second optical component 1850. The fluid chamber 1805 is in fluid communication with the outer reservoir 1803 via discrete fluid channels 1849 between standoffs 1855 when the first and second components 1840a and 1840b are assembled. The first and second optical components 1810 and 1850 may be planar members (e.g., optical membranes) of the first and second components 1840a and 1840b, respectively. The first and second optical components 1810 and 1850, for example, can be integrally formed as optical membranes with the other portions of the first and second components 1840a and 1840b. In alternate embodiments, either or both of the membranes of the first and second optical components 1810 and 1850 may be a lens (i.e., have an optical power).

The AIOL 1800 can further include a square-shaped annular region 1851 that inhibits cell migration from the periphery of the patient's capsule to the optical part of AIOL 1800 (shown in FIGS. 18C-D at the posterior most region of the lens). Such cell migration could cause post-surgery opacification of the optical system.

The peripheral portions of the first component 1840a and the second component 1840b define the outer fluid reservoir 1803, and the inner portions of the first and second components 1840a and 1840b define the accommodating structural element 1840. The first and second components 1840a and 1840b can be bonded together at a seam 1801 by means as described elsewhere herein. The first and second components 1840a and 1840b can also be bonded at other areas, such as at the standoffs 1855. The standoffs 1855 are separated by spaces that define fluid channels between the outer fluid reservoir 1803 and the inner fluid chamber 1805. The outer fluid reservoir 1803 can be a bellows 1808 having an outer bellows region 1803a and an inner bellows region 1803b, and the inner bellows region 1803b can be defined by the channels between the standoffs 1855.

The outer fluid reservoir 1803 has less volume than the outer fluid reservoirs of other AIOLs described herein, and in particular the volume of the inner bellows region 1803b is less than the outer bellows region 1803a. By reducing the volume of the inner bellows region 1803b, additional space surrounding the optical region of the AIOL allows the optical aperture of the fixed lens 1830 to be larger compared to embodiments with larger inner bellows regions. Additionally, the passages 1820 of the fixed lens 1830, which allow aqueous fluid to freely flow in and out of the chamber 1841, are configured to pass through only the outer skirt 1832 and not the top optical portion 1836. This is expected to reduce unwanted scattered light from internal reflections which may pass through the optical system and reach the retina.

The first component 1840a may also comprise one or more thickened regions 1860 for use as described above with respect to, for instance, the thickened region 1860 of the AIOL 700 for use in filling the AIOL with an optical fluid. The thickened region 1860 allows for a longer path for a needle used to fill the accommodating structure with optical fluid while a second needle in a different region is used to remove the gases the fluid is replacing. As illustrated, the fluid fill thickened region 1860 is located adjacent one or more of the outer fluid flow-throughs 1881.

Figure 9A:
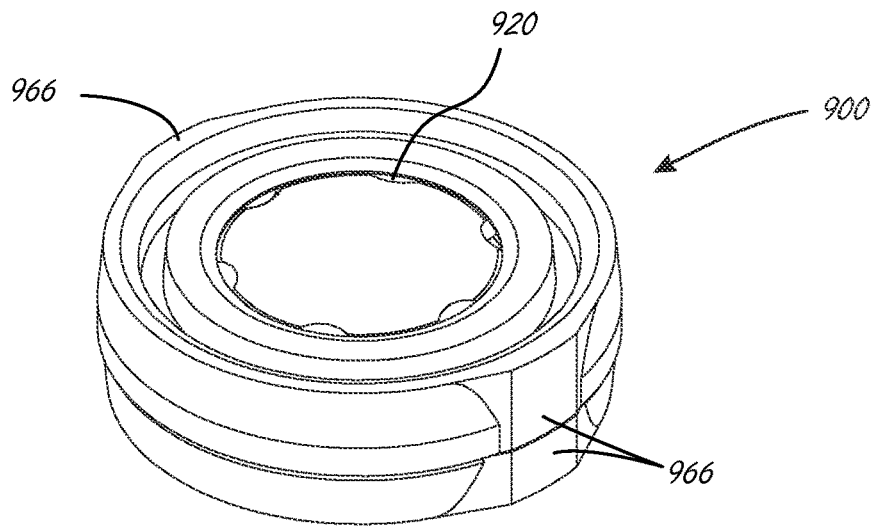
FIGS. 9A-9C illustrate accommodating intraocular lens systems 900 incorporating additional features to enhance performance.
Figure 9B:
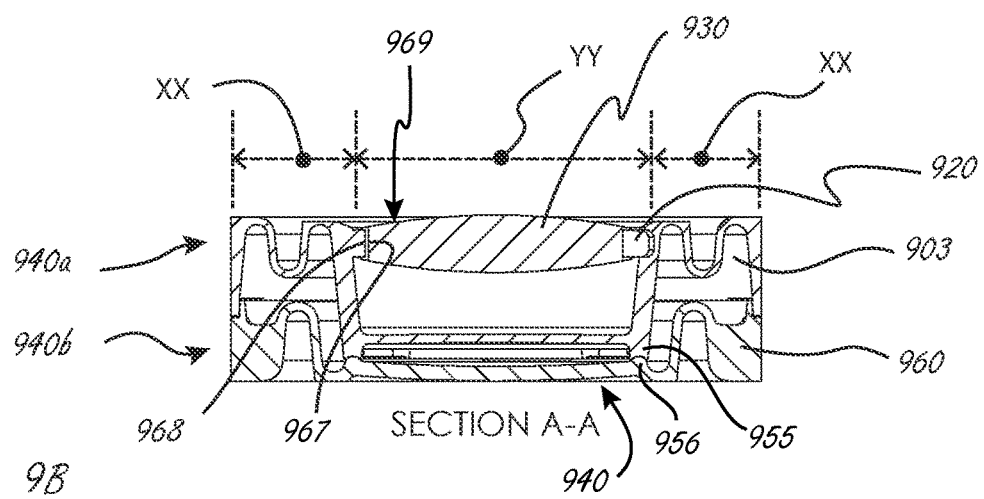
Figure 9C:
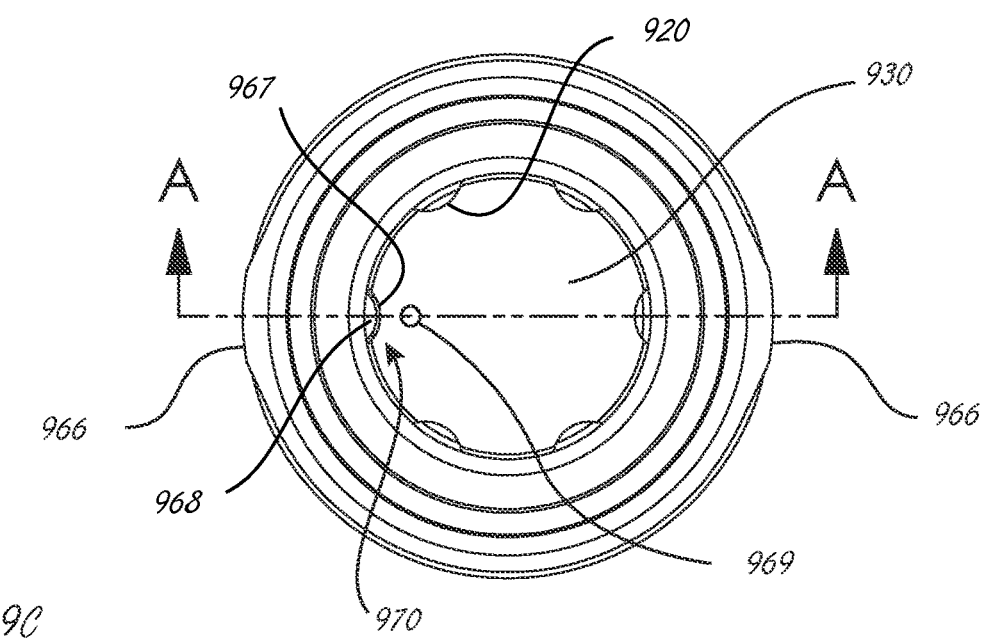

Referring to FIG. 18D, the outer fluid reservoir 1803 of the AIOL 1800 can comprise (a) a first bellows structure 1803a with an anterior portion 1804a and a posterior portion 1804b, (b) a second bellows structure 1803b radially inward of the first bellows structure 1804a, and (c) the mid-bellows channel structure 1873 defining a horizontal passageway between the first and second bellows structures 1803a and 1803b. During operation as the capsule contracts, a mid-portion of the first bellows structure 1803a is constrained by the mid-bellows channel 1873 while the anterior and posterior portions 1804a and 1804b of the first bellows structure 1803a move radially inward with respect to the mid-bellows channel 1873. The anterior and posterior portions 1804a and 1804b of the first bellows structure 1803a will accordingly flex radially inward to a greater extent than some other outer reservoir structures described above (e.g., outer fluid reservoir 103 shown in FIG. 1) in response to the same amount of movement of the native capsule. This causes more fluid to flow from the outer fluid reservoir 1803 to the inner fluid chamber 1805 and thereby provides more accommodation because anterior-posterior collapse of the outer fluid reservoir 1803 is less efficient than radial compression of the outer fluid reservoir 1803. Embodiments such as but not limited to any of those illustrated herein may be constructed from parts in which some or all of the portions not in the optical path XX have been dyed or treated to reduce light throughout to limit the ability of stray light entering portions outside the optical path from scattering into the optical path YY as indicated in FIG. 9B.

The fixed lens described in any of the embodiments described herein may be of spheric, aspheric, toric, or any other known lens configuration. Alternatively, or in combination, the fixed solid lens may be plano-convex, convex-concave, or convex-convex. The fixed lens may be configured to have positive or have negative fixed power.

The fluid lenses described herein may be configured such as to have one or more accommodating surfaces, for example two accommodating surfaces.

In some embodiments, the optical fluid may be comprised of a high refractive index poly vinyl alcohol.

In some embodiments, instead of membranes without a power, the accommodating structure can include one or more deformable lenses that deflect based upon fluid pressure within the inner fluid chamber. The deformable lenses can each or both have a fixed power that can be positive or negative.

The multipart AIOL devices described herein may be implanted by preparing the eye and removing the native lens from the capsule in any appropriate manner. The fluid-filled structure may then be placed in the capsule of the eye. The patient may then be evaluated for a base optical power and/or astigmatic correction, and a fixed lens is selected to provide the desired based power or astigmatic correction for the fluid-filled structure in the implanted state in the capsule of the eye. The specific fixed lens to provide the post-implant base power or astigmatic correction is then inserted into the previously implanted fluid-filled structure of the AIOL. The chosen fixed lens may then be coupled to the fluid-filled structure within the eye capsule. This is possible in the AIOLs of the present technology because the fixed lenses are attached to the anterior first component of the AIOLs. As described above, one or more of the fluid-filled accommodating structure or fixed lens may each be flexible such that they may be reconfigured (e.g., folded) to a reduced-profile delivery configuration for delivery into the lens capsule. In some instances, it may be required to make a further correction to the fixed portion after the time of the surgery. Such instance may occur anywhere from days to years after the surgery. At such times, the patient may return to the physician and the fixed lens may be replaced with a new fixed lens having a different optical power or other prescription. In such instances, the new prescription may be characterized prior to or after removal of the original fixed lens. In some instances, the new fixed lens may be fabricated and implanted at the time of the examination, in others the patient may return for implantation of the fixed lens sometime after the examination.

Several embodiments of the present technology are directed to a kit having an accommodating structure and a first fixed lens that has no optical base power. The kit can further include one or more second fixed lenses having various based powers or other optical properties. In practice, the accommodating structure can be implanted into the native eye capsule, and then the first fixed lens can be coupled to the accommodating structure. The optical properties of the implanted accommodating structure can then be assessed in situ with the first fixed lens in place to determine the desired optical properties of the fixed lens. If the optical properties of the assembled accommodating structure and first fixed lens without a base power are appropriate, then the system can remain implanted without additional changes. However, if a different base power or some other optical property is desired (e.g., toric or other asymmetrical optics), then the first fixed lens without a base power can be replaced with a second fixed lens having the desired optical properties based on the optical properties of the implanted accommodating portion with a fixed lens attached.

In some embodiments, the fixed portion of the AIOL may be fabricated from materials different from the accommodating portion. Such materials include hydrophilic or hydrophobic methacrylate or silicones and any other materials traditionally used in non-accommodating IOLs. The fixed lens may be fabricated from materials harder than those used for the accommodating portion.

Any of the features of the intraocular lens systems described herein may be combined with any of the features of the other intraocular lenses described herein and vice versa. Additionally, several specific examples of embodiments in accordance with the present technology are set forth below in the following examples.

EXAMPLES

1. An accommodating intraocular lens system, comprising:
   an accommodating structure including a first optical component, a second optical component posterior of the first optical component, an inner fluid chamber between the first and second optical components, and an outer fluid reservoir fluidically coupled to the inner fluid chamber, wherein the outer fluid reservoir is around at least a portion of the inner fluid chamber and configured to interface with a native eye capsule such that fluid flows between the outer fluid reservoir and the inner fluid chamber to move the first optical element for providing accommodation; and
   a fixed lens configured to be detachably coupled to the accommodating structure such that the fixed lens is anterior of the first optical component, wherein the fixed lens has a fixed optical power.

2. The accommodating intraocular lens system of example 1 wherein the fixed lens comprises an optical portion and skirt projecting from the optical portion.

3. The accommodating intraocular lens system of example 2 wherein the skirt comprises an annular wall projecting posteriorly from the optical portion.

4. The accommodating intraocular lens system of example 3 wherein the skirt flares radially outward posteriorly from the optical portion.

5. The accommodating intraocular lens system of any of examples 3-4 wherein the fixed lens further comprises a passage through the skirt.

6. The accommodating intraocular lens system of any of examples 3-5 wherein the fixed lens further comprises a passage extending laterally through the skirt, and wherein the passage does not extend through the optical portion.

7. The accommodating intraocular lens system of any of examples 3-6 wherein the fixed lens comprises a passage.

8. The accommodating intraocular lens system of any of examples 1-7 wherein the fixed lens has a positive optical power.

9. The accommodating intraocular lens system of any of examples 1-7, wherein the fixed lens has a negative optical power.

10. The accommodating intraocular lens system of any of examples 1-7 wherein the optical power of the fixed lens is zero.

11. The accommodating intraocular lens system of any of examples 1-10 wherein the fixed lens comprises an asymmetric lens.

12. The accommodating intraocular lens system of any of examples 1-11 wherein the optical structure has an anterior component and a posterior component, the anterior component including the first optical component and a first peripheral region around the first optical component, the posterior component including the second optical component and a second peripheral region around the second optical component, and wherein the first peripheral region is attached to the second peripheral region along a seam such that the first and second peripheral regions define the outer fluid reservoir.

13. The accommodating intraocular lens system of example 12 wherein the outer fluid reservoir comprises a first bellows structure, a second bellows structure radially inward of the first bellows structure, and a mid-bellows channel structure between the first and second bellows structures, and wherein the mid-bellows channel structure includes a transverse portion and the first bellows structure has an anterior portion projecting anteriorly from the transverse portion and a posterior portion projecting posteriorly from the transverse portion.

14. The accommodating intraocular lens system of example 13 wherein the anterior and posterior portions of the first bellows structure are configured to flex radially inwardly with respect to an outer-most section of the transverse portion in operation.

15. The accommodating structure of any of examples 12-14 wherein at least one of the anterior portion or the posterior portion comprises standoffs between the inner fluid chamber and the outer fluid reservoir, the standoffs defining channels therebetween for fluid to flow between the inner fluid chamber and the outer fluid reservoir.

16. The accommodating structure of example 15 wherein at least a portion of the standoffs are bonded to the other of the anterior portion or the posterior portion.

17. The accommodating intraocular lens system of any of examples 1-16, further comprising a cell dam posterior of a posterior-most portion of the outer fluid reservoir.

18. The accommodating intraocular lens system of any of examples 1-11 wherein the outer fluid reservoir comprises a first bellows structure having an anterior portion and a posterior portion, a second bellows structure radially inward of the first bellows structure, and a mid-bellows channel structure defined by a horizontal passageway between the first and second bellows structures, and wherein a mid-portion of the first bellows structure is constrained by the mid-bellows channel structure such that the anterior and posterior portions of the first bellows structure move radially inward with respect to the mid-bellows channel in operation.

19. The accommodating intraocular lens system of any of examples 1-18 wherein the outer fluid reservoir has radial inward recesses that define outer flow through features.

20. The accommodating intraocular lens system of any of examples 1-19, further comprising at least one thickened portion defining a path for a needle used to fill the accommodating structure with optical fluid.

21. An accommodating intraocular lens system, comprising:
an accommodating structure having an anterior portion and a posterior portion relative to a reference frame of a native eye, the anterior portion and posterior portion defining (a) an optical structure having inner fluid chamber and (b) an outer fluid reservoir, wherein the outer fluid reservoir is configured to interface with a native eye capsule such that fluid flows between the outer fluid reservoir and the inner fluid chamber to change the shape of the optical structure; and
a fixed lens having a fixed optical power, wherein the fixed lens is configured to be coupled to and detached from the anterior portion of the accommodating structure while the accommodating structure is implanted in a native eye capsule.

22. The accommodating intraocular lens system of example 21 wherein the fixed lens comprises an optical portion and skirt projecting from the optical portion.

23. The accommodating intraocular lens system of example 22 wherein the skirt comprises an annular wall projecting posteriorly from the optical portion.

24. The accommodating intraocular lens system of example 23 wherein the skirt flares radially outward posteriorly from the optical portion.

25. The accommodating intraocular lens system of any of examples 22-24 wherein the fixed lens further comprises a passage through the skirt.

26. The accommodating intraocular lens system of any of examples 22-24 wherein the fixed lens further comprises a passage extending laterally through the skirt, and wherein the passage does not extend through the optical portion.

27. The accommodating intraocular lens system of any of examples 22-24 wherein the fixed lens comprises a passage.

28. The accommodating intraocular lens system of any of examples 21-27 wherein the fixed lens has a positive optical power.

29. The accommodating intraocular lens system of any of examples 21-27, wherein the fixed lens has a negative optical power.

30. The accommodating intraocular lens system of any of examples 21-27 wherein the optical power of the fixed lens is zero.

31. The accommodating intraocular lens system of any of examples 21-30 wherein the fixed lens comprises an asymmetric lens.

32. The accommodating intraocular lens system of any of examples 21-31 wherein:
the anterior portion of the accommodating structure includes a first optical component and a first peripheral region around the first optical component;
the posterior portion of the accommodating structure includes a second optical component and a second peripheral region around the second optical component; and the first peripheral region is attached to the second peripheral region along a seam such that the first and second peripheral regions define the outer fluid reservoir.

33. The accommodating intraocular lens system of example 32 wherein the outer fluid reservoir comprises a first bellows structure, a second bellows structure radially inward of the first bellows structure, and a mid-bellows channel structure between the first and second bellows structures, and wherein the mid-bellows channel structure includes a transverse portion and the first bellows structure has (a) an anterior portion projecting anteriorly from the transverse portion and (b) a posterior portion projecting posteriorly from the transverse portion.

34. The accommodating intraocular lens system of example 33 wherein the anterior and posterior portions of the first bellows structure are configured to flex radially inwardly with respect to an outer-most section of the transverse portion in operation.

35. The accommodating structure of example 32 wherein at least one of the anterior portion or the posterior portion of the accommodating structure comprises standoffs between the inner fluid chamber and the outer fluid reservoir, the standoffs defining channels therebetween for fluid to flow between the inner fluid chamber and the outer fluid reservoir.

36. The accommodating structure of example 35 wherein at least a portion of the standoffs are bonded to the other of the anterior portion or the posterior portion of the accommodating structure.

37. The accommodating intraocular lens system of any of examples 21-36, further comprising a cell dam posterior of a posterior-most portion of the outer fluid reservoir.

38. The accommodating intraocular lens system of any of examples 21-31 wherein the outer fluid reservoir comprises a first bellows structure having an anterior portion and a posterior portion, a second bellows structure radially inward of the first bellows structure, and a mid-bellows channel structure defined by a horizontal passageway between the first and second bellows structures, and wherein a mid-portion of the first bellows structure is constrained by the mid-bellows channel structure such that the anterior and posterior portions of the first bellows structure move radially inward with respect to the mid-bellows channel in operation.

39. The accommodating intraocular lens system of any of examples 21-38 wherein the outer fluid reservoir has radial inward recesses that define outer flow through features.

40. The accommodating intraocular lens system of any of examples 21-39, further comprising at least one thickened portion defining a path for a needle used to fill the accommodating structure with optical fluid.

41. An accommodating intraocular lens system, comprising:
   a kit including—
      an accommodating structure including a first optical component, a second optical component posterior of the first optical component, an inner fluid chamber between the first and second optical components, and an outer fluid reservoir fluidically coupled to the inner fluid chamber, wherein the outer fluid reservoir is around at least a portion of the inner fluid chamber and configured to interface with a native eye capsule such that fluid flows between the outer fluid reservoir and the inner fluid chamber to move the first optical element for providing accommodation; and
      a first fixed lens configured to be detachably coupled to the accommodating structure such that the first fixed lens is anterior of the first optical component, wherein the first fixed lens has no optical power; and
      a second fixed lens configured to be detachably coupled to the accommodating structure instead of the first fixed lens such that the second fixed lens is anterior of the first optical element, wherein the second fixed lens has an optical power.

42. The system of example 41 wherein the each of the first fixed lens and the second fixed lens comprises an optical portion and skirt projecting from the optical portion.

43. The system of example 42 wherein the skirt comprises an annular wall projecting posteriorly from the optical portion.

44. The system of example 43 wherein the skirt flares radially outward posteriorly from the optical portion.

45. The system of any of examples 42-44 wherein each of the first fixed lens and the second fixed lens further comprises a passage extending laterally through the skirt, and wherein the passage does not extend through the optical portion.

46. The system of any of examples 41-45 wherein at least one of the first fixed lens or the second fixed lens comprises an asymmetric lens.

47. The system of any of examples 41-46 wherein the optical structure has an anterior component and a posterior component, the anterior component including the first optical component and a first peripheral region around the first optical component, the posterior component including the second optical component and a second peripheral region around the second optical component, and wherein the first peripheral region is attached to the second peripheral region along a seam such that the first and second peripheral regions define the outer fluid reservoir.

48. The system of example 47 wherein the outer fluid reservoir comprises a first bellows structure, a second bellows structure radially inward of the first bellows structure, and a mid-bellows channel structure between the first and second bellows structures, and wherein the mid-bellows channel structure includes a transverse portion and the first bellows structure has an anterior portion projecting anteriorly from the transverse portion and a posterior portion projecting posteriorly from the transverse portion.

49. The system of example 48 wherein the anterior and posterior portions of the first bellows structure are configured to flex radially inwardly with respect to an outer-most section of the transverse portion in operation.

50. The system of example 47 wherein at least one of the anterior portion or the posterior portion comprises standoffs between the inner fluid chamber and the outer fluid reservoir, the standoffs defining channels therebetween for fluid to flow between the inner fluid chamber and the outer fluid reservoir.

51. The system of example 50 wherein at least a portion of the standoffs are bonded to the other of the anterior portion or the posterior portion.

52. The accommodating intraocular lens system of any of examples 41-51, further comprising a cell dam posterior of a posterior-most portion of the outer fluid reservoir.

53. The system of any of examples 41-46 wherein the outer fluid reservoir comprises a first bellows structure having an anterior portion and a posterior portion, a second bellows structure radially inward of the first bellows structure, and a mid-bellows channel structure defined by a horizontal passageway between the first and second bellows structures, and wherein a mid-portion of the first bellows structure is constrained by the mid-bellows channel structure such that the anterior and posterior portions of the first bellows structure move radially inward with respect to the mid-bellows channel in operation.

54. The system of any of examples 41-53 wherein the outer fluid reservoir has radial inward recesses that define outer flow through features.

55. The system of any of examples 41-54, further comprising at least one thickened portion defining a path for a needle used to fill the accommodating structure with optical fluid.

56. A method of implementing an accommodating intraocular lens system, comprising:
implanting an accommodating structure into a native eye capsule, wherein the accommodating structure has a first optical component, a second optical component posterior of the first optical component, an inner fluid chamber between the first and second optical components, and an outer fluid reservoir fluidically coupled to the inner fluid chamber;
coupling a fixed lens to the accommodating structure after implanting the accommodating structure in the native eye capsule.

57. The method of example 56 wherein the fixed lens comprises a first fixed lens, and the method further comprises (a) detaching the first fixed lens from the accommodating structure and (b) attaching a second fixed lens to the accommodating structure, and wherein the second fixed lens has a different optical power than the first fixed lens.

58. The method of any of examples 56-57 wherein the fixed lens comprises an optical portion and a skirt projecting posteriorly from the optical portion such that an aqueous chamber is formed between the optical portion of the fixed lens and the first optical component of the accommodating structure when the fixed lens is coupled to the accommodating structure.

59. The method of any of examples 56-58 wherein the first optical component is part of an anterior component and the second optical component is part of a posterior component, and the method comprises coupling and fluidically sealing the anterior and posterior components together before implanting the accommodating structure.

60. The method of example 59 wherein the anterior and posterior components are coupled and fluidically sealed together in a dry state, and further comprising hydrating the coupled and fluidically sealed anterior and posterior components before implanting the accommodating structure.

61. The method of any of examples 56-60 wherein the accommodating structure has an index mark and the method further comprises rotating the fixed lens based on the index mark on the accommodating structure.

62. The method of example 61 wherein the fixed lens has physical feature and the process of rotating the fixed lens comprises registering the physical feature of the fixed lens with respect to the index mark on the accommodating structure.

63. The method of example 56 wherein the fixed lens comprises a first fixed lens, and wherein the method further comprises:
assessing whether the implanted accommodating structure with the first fixed lens coupled to the accommodating structure in the eye provides a desired accommodation; and
replacing the first fixed lens with a second fixed lens having a different base power when the assessed accommodation is different than the desired accommodation.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the disclosure.

What is claimed is:

1. An accommodating intraocular lens (AIOL) comprising:
a first component having—
a first optical portion having an optical axis;
a first haptic portion surrounding the first optical portion; and
a first annular wall connecting the first optical portion to the first haptic portion; and
a second component having—
a second annular wall connected to the first annular wall;
a second optical portion aligned with the first optical portion along the optical axis to form an optic chamber between the first optical portion and the second optical portion, the optic chamber having an adjustable optical power;
a second haptic portion connected to (i) the second optical portion via the second annular wall and (ii) the first haptic portion to form a haptic reservoir between the first haptic portion and the second haptic portion;
wherein—
one or both of the first annular wall and the second annular wall includes standoffs extending from the first or second annular walls;
spaces between the standoffs form passages through which fluid can flow between the haptic reservoir and the optic chamber; and
the optical power of the optic chamber is configured to increase when radial compressive force is applied to the first and/or second haptic portions.

2. The AIOL of claim 1 wherein the AIOL is configured to be releasably coupled with a lens having a fixed optical power.

3. The AIOL of claim 1, further comprising one or more indentations or projections on a radially-inward portion of the first annular wall, the one or more indentations or projections being configured to releasably couple with a lens having a fixed optical power.

4. The AIOL of claim 1 wherein at least portions of both the first optical portion and the second optical portion extend past the second haptic portion in a direction parallel to the optical axis and opposite the first haptic portion.

5. The AIOL of claim 1 wherein the first component and the second component comprise a silicone material.

6. The AIOL of claim 1 wherein the second optical portion is positioned past the second haptic portion in a direction parallel to the optical axis and opposite the first optical portion.

7. The AIOL of claim 1 wherein:
the first haptic portion has a first radially-outward wall forming a first outer perimeter of the first haptic portion; and
the second haptic portion has a second radially-outward wall forming a second outer perimeter of the second haptic portion and connected to the first radially-outward wall.

8. The AIOL of claim 7 wherein the first radially-outward wall overlaps the second radially-outward wall with respect to the optical axis.

9. The AIOL of claim 1 wherein the first annular wall includes the standoffs, and wherein one or more of the standoffs extend radially-outward from the first annular wall with respect to the optical axis.

10. The AIOL of claim 1 wherein the second annular wall includes the standoffs, and wherein one or more of the standoffs extend away from the second optical portion in a direction parallel to the optical axis.

11. The AIOL of claim 1 wherein the first and the second haptic portions each have a radially-outermost wall, and wherein the radially-outermost wall of each of the first and the second haptic portions include radial indentations.

12. An accommodating intraocular lens (AIOL) comprising:
- a lens portion having—
  - an optical axis;
  - an anterior lens;
  - a posterior lens positioned posterior to the anterior lens along the optical axis; and
  - an optic chamber between the anterior lens and the posterior lens, the optic chamber containing a fluid;
- an annular haptic portion having—
  - an anterior wall surrounding the anterior lens;
  - a posterior wall connected to the anterior wall and surrounding the posterior lens; and
  - a haptic reservoir between the anterior wall and the posterior wall;
- a first annular wall connecting the lens portion to the annular haptic portion; and
- a second annular wall connecting the lens portion to the annular haptic portion;

wherein—
- one or both of the first annular wall and the second annular wall includes standoffs extending from the first or second annular walls; and
- spaces between the standoffs form passages through which the fluid can flow between the haptic reservoir and the optic chamber.

13. The AIOL of claim 12 wherein an optical power of the optic chamber is configured to increase when a radial compressive force is applied to the annular haptic portion.

14. The AIOL of claim 12 wherein the first annular wall is configured to releasably couple with a fixed optical power lens.

15. The AIOL of claim 12 wherein an anterior-most surface of the anterior wall of the annular haptic portion is annular and lies on a plane perpendicular to the optical axis.

16. The AIOL of claim 15 wherein the anterior-most surface of the anterior wall is circular.

17. The AIOL of claim 12 wherein a thickness of the anterior wall, as measured parallel to the optical axis, varies around a perimeter of the annular haptic portion.

18. The AIOL of claim 12 wherein a depth of the haptic reservoir, as measured parallel to the optical axis, varies around a perimeter of the annular haptic portion.

19. The AIOL of claim 12 wherein a portion of the anterior wall of the annular haptic portion overlaps a portion of the posterior wall of the annular haptic portion in a direction parallel to the optical axis.

20. The AIOL of claim 12 wherein the first annular wall includes one or more indentations in a radially-inward surface of the first annular wall.

* * * * *